(12) United States Patent
Drescher et al.

(10) Patent No.: US 8,232,426 B2
(45) Date of Patent: Jul. 31, 2012

(54) AMINOETHYLAROMATIC COMPOUNDS SUITABLE FOR TREATING DISORDERS THAT RESPOND TO MODULATION OF THE DOPAMINE D3 RECEPTOR

(75) Inventors: Karla Drescher, Dossenheim (DE); Andreas Haupt, Schwetzingen (DE); Liliane Unger, Ludwigshafen (DE); Sean C. Turner, Mannheim (DE); Wilfried Braje, Mannheim (DE); Roland Grandel, Dossenheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 1048 days.

(21) Appl. No.: 11/665,288

(22) PCT Filed: Oct. 14, 2005

(86) PCT No.: PCT/EP2005/011092
§ 371 (c)(1),
(2), (4) Date: Nov. 23, 2007

(87) PCT Pub. No.: WO2006/040179
PCT Pub. Date: Apr. 20, 2006

(65) Prior Publication Data
US 2008/0096934 A1  Apr. 24, 2008

Related U.S. Application Data

(60) Provisional application No. 60/618,880, filed on Oct. 14, 2004.

(51) Int. Cl.
*C07C 303/00* (2006.01)
*A61K 31/18* (2006.01)
(52) U.S. Cl. .................................... 564/80; 514/601
(58) Field of Classification Search .................. 564/80; 514/601
See application file for complete search history.

(56) References Cited

FOREIGN PATENT DOCUMENTS
WO  WO 99/58499  11/1999
WO  WO 03/095428  11/2003

OTHER PUBLICATIONS

Narasimha et al Journal of the Indian Chemical Society, 1941, 18, 316-320.*
Baxter et al Tetrahedron Letters 1998, 39, 979-982.*
J.C. Schwartz et al., The Dopamine D₃ Receptor as a Target for Antipsychotics, in Novel Antipsychotic Drugs, H.Y. Meltzer, Ed. Raven Press, New York, 1992, pp. 135-144.
M. Dooley et al., Drugs and Aging 1998, 12, 495-514.
J. N. Joyce, Pharmacology and Therapeutics 2001, 90, pp. 231-259 "The Dopamine D₃ Receptor as a Therapeutic Target for Antipsychotic and Antiparkinsonian Drugs".
P. Sokoloff et al., Localization and Function of the D₃ Dopamine Receptor, Arzneim. Frosch./Drug Res. 42(1), 224 (1992).
P. Sokoloff et al., Molecular Cloning and Characterization of a Novel Dopamine Receptor (D₃) as a Target for Neuroleptics, Nature, 347, 146 (1990).
Rudmann, D.G., et al., "Epididymal and systemic phospholipidosis in rats and dogs treated with the dopamine D3 selective antagonist PNU-177864," Toxicologic Pathology, (2004), 32(3), pp. 326-332.
Vonderfecht, S.L., "Myopathy related to administration of a cationic amphiphilic drug and the use of multidose drug distribution analysis to predict its occurrence," Toxicologic Pathology, (2004), 32(3), pp. 318-325.

* cited by examiner

*Primary Examiner* — Janet Andres
*Assistant Examiner* — John Mabry
(74) *Attorney, Agent, or Firm* — Lisa V. Mueller; Michael Best & Friedrich LLP

(57) ABSTRACT

The present invention relates to aromatic compounds of the formula I

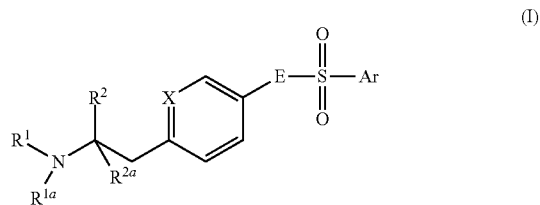

(I)

wherein Ar is phenyl or an aromatic 5- or 6-membered C-bound heteroaromatic radical, wherein Ar may carry 1 radical $R^a$ and wherein Ar may also carry 1 or 2 radicals $R^b$;
X is N or CH;
E is $CR^6R^7$ or $NR^3$;
$R_1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;
$R^{1a}$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, or $R^{1a}$ and $R^2$ together are $(CH_2)_n$ with n being 2, 3 or 4, or $R^{1a}$ and $R^{2a}$ together are $(CH_2)_n$ with n being 2, 3 or 4;
$R^2$ and $R^{2a}$ are are independently of each other H, $C_1$-$C_4$-alkyl or fluorinated $C_1$-$C_4$-alkyl or $R^{2a}$ and $R^2$ together are $(CH_2)_m$ with m being 1, 2, 3, 4 or 5;
$R^3$ is H or $C_1$-$C_4$-alkyl;
$R^6$, $R^7$ independently of each other are selected from H, fluorine, $C_1$-$C_4$-alkyl and fluorinated $C_1$-$C_4$-alkyl or together form a moiety $(CH_2)_p$ with p being 2, 3, 4 or 5;
and the physiologically tolerated acid addition salts thereof. The invention also relates to the use of a compound of the formula I or a pharmaceutically acceptable salt thereof for preparing a pharmaceutical composition for the treatment of a medical disorder susceptible to treatment with a dopamine D3 receptor ligand.

19 Claims, No Drawings

AMINOETHYLAROMATIC COMPOUNDS SUITABLE FOR TREATING DISORDERS THAT RESPOND TO MODULATION OF THE DOPAMINE D3 RECEPTOR

BACKGROUND OF THE INVENTION

The present invention relates to novel aminoethylaromatic compounds. The compounds possess valuable therapeutic properties and are suitable, in particular, for treating diseases that respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disorders in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression; $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, Arzneim. Forsch./Drug Res. 42(1), 224 (1992); P. Sokoloff et al. Molecular Cloning and Characterization of a Novel Dopamine Receptor ($D_3$) as a Target for Neuroleptics, Nature, 347, 146 (1990)).

WO 99/58499 discloses phenylsulfonamide substituted phenethylamines having an affinity for the dopamine $D_3$ receptor. The phenyl ring of the phenylsulfonamide moiety preferably carries a radical selected from $C_1$-$C_3$-alkyl, halogen, $OCH_3$, $OCF_3$, $CF_3$, CN, $SCH_3$ or $NHCOCH_3$. These compounds are selective for the Dopamine $D_3$ receptor and possess only modest affinities for the dopamine $D_2$ receptor. They have therefore been proposed as being suitable for treating diseases of the central nervous system. Unfortunately their affinity for the $D_3$ receptor or their pharmacological profile are not satisfactory. Consequently there is an ongoing need to provide new compounds, which either have an high affinity and an improved selectivity. The compounds should also have good pharmacological profile, e.g. a high brain plasma ratio, a high bioavailability, metabolic stability or a decreased inhibition of the mitochondrial respiration.

SUMMARY OF THE INVENTION

The invention is based on the object of providing compounds which act as highly selective dopamine $D_3$ receptor ligands. This object is surprisingly achieved by means of aminoethylaromatic compounds of the formula I

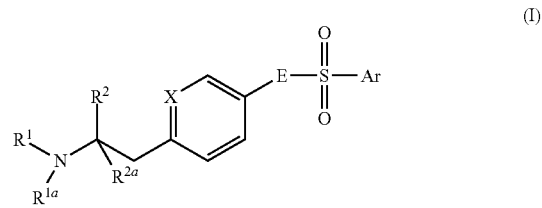

wherein

Ar is phenyl or an aromatic 5- or 6-membered C-bound heteroaromatic radical, wherein Ar may carry 1 radical $R^a$ and wherein Ar may also carry 1 or 2 radicals $R^b$;

$R^a$ being selected from the group consisting of $C_1$-$C_6$-alkyl, $C_2$-$C_6$-alkenyl, fluorinated $C_2$-$C_6$-alkenyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenyl, phenoxy, benzyloxy and a 3- to 7-membered heterocyclic radical, wherein the five last mentioned radicals may carry 1, 2, 3 or 4 radicals selected from halogen, cyano, OH, oxo, CN, and the radicals $R^a$, $R^b$ being, independently from each other, selected from halogen, cyano, nitro, OH, methyl, methoxy, fluoromethyl, difluoromethyl, trifluoromethyl, fluoromethoxy, difluoromethoxy and trifluoromethoxy, the radical $R^a$ and one radical $R^b$, if present and bound to two adjacent carbon atoms of phenyl, may form a 5- or 6-membered heterocyclic or carbocyclic ring which is fused to the phenyl ring and which is unsubstituted or which may carry 1, 2 or 3 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl, X is N or CH;

E is $CR^6R^7$ or $NR^3$;

$R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H, $C_1$-$C_4$-alkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, or $R^{1a}$ and $R^2$ together are $(CH_2)_n$ with n being 2, 3 or 4, or $R^{1a}$ and $R^{2a}$ together are $(CH_2)_n$ with n being 2, 3 or 4;

$R^2$ and $R^{2a}$ are independently of each other H, $C_1$-$C_4$-alkyl or fluorinated $C_1$-$C_4$-alkyl or $R^{2a}$ and $R^2$ together are $(CH_2)_m$ with m being 2, 3, 4 or 5;

$R^3$ is H or $C_1$-$C_4$-alkyl;

$R^4$, $R^5$ independently of each other are selected from H, $C_1$-$C_3$-alkyl, $C_1$-$C_3$-alkoxy and fluorinated $C_1$-$C_3$-alkyl;

$R^6$, $R^7$ independently of each other are selected from H, fluorine, $C_1$-$C_4$-alkyl and fluorinated $C_1$-$C_4$-alkyl or together form a moiety $(CH_2)_p$ with p being 2, 3, 4 or 5;

provided that for $R^1$ being $C_1$-$C_4$-alkyl, $R^2$=$R^{2a}$ being H, E being NH, X being CH and Ar=substituted phenyl Ar carries at least one substituent $R^a$ which is different from linear $C_1$-$C_3$-alkyl, $OCH_3$, $OCF_3$, $CF_3$, $SCH_3$ or $NHC(O)CH_3$, and which is preferably selected from secondary $C_3$-$C_6$-alkyl, fluorinated $C_2$-$C_6$-alkyl, fluorinated $C_3$-$C_6$-cycloalkyl, fluorinated $C_2$-$C_6$-alkoxy, $CHF_2$, $CF_2$, $OCHF_2$, $OCF_2$, $NR^4R^5$, 1-aziridinyl, azetidin-1-yl, pyrrolidin-1-yl or piperidin-1-yl, wherein the last for mentioned radicals may be fluorinated or may carry 1 or 2 radicals selected from OH, oxo, $C_1$-$C_2$-alkyl, fluorinated $C_1$-$C_2$-alkyl or $C_1$-$C_2$-alkoxy, a phenyl group and an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 radicals selected from halogen, $NO_2$, OH, CN, and the radicals $R^a$ such as $NH_2$, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl;

and the physiologically tolerated acid addition salts of these compounds.

The present invention therefore relates to aminoethylaromatic compounds of the general formula I and to their physiologically tolerated acid addition salts.

The present invention also relates to a pharmaceutical composition which comprises at least one aminoethylaromatic compound of the formula I and/or at least one physiologically tolerated acid addition salt of 1, where appropriate together with physiologically acceptable carriers and/or auxiliary substances.

The present invention also relates to a method for treating disorders which respond to influencing by dopamine $D_3$ receptor antagonists or dopamine $D_3$ agonists, said method comprising administering an effective amount of at least one aminoethylaromatic compound of the formula I and/or at least one physiologically tolerated acid addition salt of I to a subject in need thereof.

DETAILED DESCRIPTION OF THE INVENTION

The diseases which respond to the influence of dopamine $D_3$ receptor antagonists or agonists include, in particular, disorders and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, poly-substituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids; such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte-der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$—$C_m$ indicates in each case the possible number of carbon atoms in the group.

The term halogen denotes in each case fluorine, bromine, chlorine or iodine, in particular fluorine or chlorine.

$C_1$-$C_4$ Alkyl (and likewise in $C_1$-$C_4$ hydroxyalkyl, $C_1$-$C_6$ alkoxy-$C_1$-$C_4$-alkyl, $C_1$-$C_4$ alkylcarbonyl, $C_1$-$C_4$ alkylcarbonylamino, $C_1$-$C_4$ alkylcarbonyloxy, $C_1$-$C_4$ alkylthio, $C_1$-$C_4$ alkylsulfinyl, $C_1$-$C_4$ alkylsulfonyl etc.) is a straight-chain or branched alkyl group having from 1 to 4 carbon atoms. Examples of an alkyl group are methyl, ethyl, n-propyl, isopropyl, n-butyl, 2-butyl, iso-butyl or tert-butyl.

$C_1$-$C_6$ Alkyl (and likewise in $C_1$-$C_6$ hydroxyalkyl, $C_1$-$C_6$ alkoxy-$C_1$-$C_4$-alkyl, $C_1$-$C_6$ alkylcarbonyl, $C_1$-$C_6$ alkylcarbonylamino, $C_1$-$C_6$ alkylcarbonyloxy, $C_1$-$C_6$ alkylthio, $C_1$-$C_6$ alkylsulfinyl, $C_1$-$C_6$ alkylsulfonyl etc.) is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Fluorinated $C_1$-$C_6$ alkyl (and likewise in fluorinated $C_1$-$C_6$ alkylcarbonyl, fluorinated $C_1$-$C_6$ alkylcarbonylamino, fluorinated $C_1$-$C_6$ alkylcarbonyloxy, fluorinated $C_1$-$C_6$ alkylthio, fluorinated $C_1$-$C_6$ alkylsulfinyl, fluorinated $C_1$-$C_6$ alkylsulfonyl etc.) is a straight-chain or branched alkyl group having from 1 to 6, in particular 1 to 4 carbon atoms, more preferably 1 to 3 carbon atoms, wherein at least one, e.g. 1, 2, 3, 4 or all of the hydrogen atoms are replaced by a fluorine atoms such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, etc.;

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl 1-methyl-1-ethylpropyl.

$C_1$-$C_6$ Alkoxy (and likewise in $C_1$-$C_6$ alkoxycarbonyl, $C_1$-$C_6$ alkoxy-$C_1$-$C_4$ alkyl, $C_1$-$C_6$ alkoxy-$C_1$-$C_4$ alkoxy and $C_1$-$C_6$ hydroxyalkoxy) is a straight-chain or branched alkyl group having from 1 to 6, in particular 1 to 4 carbon atoms, which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy;

Fluorinated $C_1$-$C_6$ alkyoxy (and likewise in fluorinated $C_1$-$C_6$alkoxycarbonyl) is a straight-chain or branched alkoxy group having from 1 to 6, in particular 1 to 4 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.;

$C_3$-$C_6$ Cycloalkyl is a cycloaliphatic radical having from 3 to 6 C atoms, such as cyclopropyl, cyclobutyl and cyclopentyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl and cyclopentyl, wherein at least one, e.g. 1, 2, 3, 4 or all of the hydrogen atoms are replaced by a fluorine atoms such as in 1-fluorocyclopropyl, 2-fluorocyclopropyl, 2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_6$ Cycloalkylmethyl is methyl which carries a cycloaliphatic radical having from 3 to 6 C atoms as mentioned above Fluorinated $C_3$-$C_6$ cycloalkylmethyl is methyl which carries a cycloaliphatic radical having from 3 to 6 C atoms, wherein at least one, e.g. 1, 2, 3, 4 or all of the hydrogen atoms are replaced by a fluorine atoms.

$C_2$-$C_6$-Alkenyl is a singly unsaturated hydrocarbon radical having 2, 3, 4, 5 or 6 C-atoms, e.g. vinyl, allyl(2-propen-1-yl), 1-propen-1-yl, 2-propen-2-yl, methallyl(2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_1$-$C_6$-hydroxyalkyl is an alkyl radical having from 1 to 6 carbon atoms as defined above, wherein one hydrogen atom is replaced by hydroxy. Examples comprise hydroxymethyl, 2-hydroxyethyl, 1-hydroxyethyl, 3-hydroxypropyl, 2-hydroxypropyl, 1-methyl-1-hydroxyethyl and the like.

$C_1$-$C_6$ hydroxyalkoxy is an alkoxy radical having from 1 to 6, preferably from 2 to 4 carbon atoms as defined above, wherein one hydrogen atom is replaced by hydroxy. Examples comprise 2-hydroxyethyl, 3-hydroxypropyl, 2-hydroxypropyl, 1-methyl-2-hydroxyethyl and the like.

$C_1$-$C_6$ alkoxy-$C_1$-$C_4$-alkyl is an alkyl radical having from 1 to 4 carbon atoms as defined above, wherein one hydrogen atom is replaced by $C_1$-$C_6$ alkoxy. Examples comprise methoxymethyl, 2-methoxyethyl, 1-methoxyethyl, 3-methoxypropyl, 2-methoxypropyl, 1-methyl-1-methoxyethyl, ethoxymethyl, 2-ethoxyethyl, 1-ethoxyethyl, 3-ethoxypropyl, 2-ethoxypropyl, 1-methyl-1-ethoxyethyl and the like.

$C_1$-$C_6$ alkoxy-$C_1$-$C_4$-alkoxy is an alkoxy radical having from 1 to 4 carbon atoms as defined above, wherein one hydrogen atom is replaced by $C_1$-$C_6$ alkoxy. Examples comprise methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

$C_1$-$C_6$ alkylcarbonyl is a radical of the formula R—C(O)—, wherein R is an alkyl radical having from 1 to 6 carbon atoms as defined above. Examples comprise acetyl, propionyl, n-butyryl, 2-methylpropionyl, pivaloyl and the like.

$C_1$-$C_6$ alkylcarbonylamino is a radical of the formula R—C(O)—NH—, wherein R is an alkyl radical having from 1 to 6 carbon atoms as defined above. Examples comprise acetamido, propionamido, n-butyramido, 2-methylpropionamido, 2,2-dimethylpropionamido and the like.

$C_1$-$C_6$ alkylcarbonyloxy is a radical of the formula R—C(O)—O—, wherein R is an alkyl radical having from 1 to 6 carbon atoms as defined above. Examples comprise acetyloxy, propionyloxy, n-butyryloxy, 2-methylpropionyloxy, 2,2-dimethylpropionyloxy and the like.

$C_1$-$C_6$ alkylthio is a radical of the formula R—S—, wherein R is an alkyl radical having from 1 to 6 carbon atoms as defined above. Examples comprise methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl;

$C_1$-$C_6$ alkylsulfinyl is a radical of the formula R—S(O)—, wherein R is an alkyl radical having from 1 to 6 carbon atoms as defined above. Examples comprise methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl;

$C_1$-$C_6$ alkylsulfonyl is a radical of the formula R—S(O)$_2$—, wherein R is an alkyl radical having from 1 to 6 carbon atoms as defined above. Examples comprise methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl;

fluorinated $C_1$-$C_6$ alkylcarbonyl is a radical of the formula R—C(O)—, wherein R is a fluorinated alkyl radical having from 1 to 6 carbon atoms as defined above. Examples comprise fluoroacetyl, difluoroacetyl, trifluoroacetyl, (R)-1-fluoroethylcarbonyl, (S)-1-fluoroethylcarbonyl, 2-fluoroethylcarbonyl, 1,1-difluoroethylcarbonyl, 2,2-difluoroethylcarbonyl, 2,2,2-trifluoroethylcarbonyl, (R)-1-fluoropropylcarbonyl, (S)-1-fluoropropylcarbonyl, 2-fluoropropylcarbonyl, 3-fluoropropylcarbonyl, 1,1-difluoropropylcarbonyl, 2,2-difluoropropylcarbonyl, 3,3-difluoropropylcarbonyl, 3,3,3-trifluoropropylcarbonyl, (R)-2-fluoro-1-methylethylcarbonyl, (S)-2-fluoro-1-methylethylcarbonyl, (R)-2,2-difluoro-1-methylethylcarbonyl, (S)-2,2-difluoro-1-methylethylcarbonyl, (R)-1,2-difluoro-1-methylethylcarbonyl, (S)-1,2-difluoro-1-methylethylcarbonyl, (R)-2,2,2-trifluoro-1-methylethylcarbonyl, (S)-2,2,2-trifluoro-1-methylethylcarbonyl, 2-fluoro-1-(fluoromethyl)ethylcarbonyl, 1-(difluoromethyl)-2,2-difluoroethylcarbonyl, (R)-1-fluorobutylcarbonyl, (S)-1-fluorobutylcarbonyl, 2-fluorobutylcarbonyl, 3-fluorobutylcarbonyl, 4-fluorobutylcarbonyl, 1,1-difluorobutylcarbonyl, 2,2-difluorobutylcarbonyl, 3,3-difluorobutylcarbonyl, 4,4-difluorobutylcarbonyl, 4,4,4-trifluorobutylcarbonyl, etc.;

fluorinated $C_1$-$C_6$ alkylcarbonylamino is a radical of the formula R—C(O)—NH—, wherein R is a fluorinated alkyl radical having from 1 to 6 carbon atoms as defined above. Examples comprise fluoroacetamido, difluoroacetamido, trifluoroacetamido, (R)-1-fluoroethylcarbonylamino, (S)-1-fluoroethylcarbonylamino, 2-fluoroethylcarbonylamino, 1,1-difluoroethylcarbonylamino, 2,2-difluoroethylcarbonylamino, 2,2,2-trifluoroethylcarbonylamino, (R)-1-fluoropropylcarbonylamino, (S)-1-fluoropropylcarbonylamino, 2-fluoropropylcarbonylamino, 3-fluoropropylcarbonylamino, 1,1-difluoropropylcarbonylamino, 2,2-difluoropropylcarbonylamino, 3,3-difluoropropylcarbonylamino, 3,3,3-trifluoropropylcarbonylamino, (R)-2-fluoro-1-methylethylcarbonylamino, (S)-2-fluoro-1-methylethylcarbonylamino, (R)-2,2-difluoro-1-methylethylcarbonylamino, (S)-2,2-difluoro-1-methylethylcarbonylamino, (R)-1,2-difluoro-1-methylethylcarbonylamino, (S)-1,2-difluoro-1-methylethylcarbonylamino, (R)-2,2,2-trifluoro-1-methylethylcarbonylamino, (S)-2,2,2-trifluoro-1-methylethylcarbonylamino, 2-fluoro-1-(fluoromethyl)ethylcarbonylamino, 1-(difluoromethyl)-2,2-difluoroethylcarbonylamino, (R)-1-fluorobutylcarbonylamino, (S)-1-fluorobutylcarbonylamino, 2-fluorobutylcarbonylamino, 3-fluorobutylcarbonylamino, 4-fluorobutylcarbonylamino, 1,1-difluorobutylcarbonylamino, 2,2-difluorobutylcarbonylamino, 3,3-difluorobutylcarbonylamino, 4,4-difluorobutylcarbonylamino, 4,4,4-trifluorobutylcarbonylamino, etc., fluorinated $C_1$-$C_6$ alkylcarbonyloxy is a radical of the formula R—C(O)—O—, wherein R is a fluorinated alkyl radical having from 1 to 6 carbon atoms as defined above fluoroacetyl, difluoroacetyl, trifluoroacetyl, (R)-1-fluoroethylcarbonyloxy, (S)-1-fluoroethylcarbonyloxy, 2-fluoroethylcarbonyloxy, 1,1-difluoroethylcarbonyloxy, 2,2-difluoroethylcarbonyloxy, 2,2,2-trifluoroethylcarbonyloxy, (R)-1-fluoropropylcarbonyloxy, (S)-1-fluoropropylcarbonyloxy, 2-fluoropropylcarbonyloxy, 3-fluoropropylcarbonyloxy, 1,1-difluoropropylcarbonyloxy, 2,2-difluoropropylcarbonyloxy, 3,3-difluoropropylcarbonyloxy, 3,3,3-trifluoropropylcarbonyloxy, (R)-2-fluoro-1-methylethylcarbonyloxy, (S)-2-fluoro-1-methylethylcarbonyloxy, (R)-2,2-difluoro-1-methylethylcarbonyloxy, (S)-2,2-difluoro-1-methylethylcarbonyloxy, (R)-1,2-difluoro-1-methylethylcarbonyloxy, (S)-1,2-difluoro-1-methylethylcarbonyloxy, (R)-2,2,2-trifluoro-1-methylethylcarbonyloxy, (S)-2,2,2-trifluoro-1-methylethylcarbonyloxy, 2-fluoro-1-(fluoromethyl)ethylcarbonyloxy, 1-(difluoromethyl)-2,2-difluoroethylcarbonyloxy, (R)-1-fluorobutylcarbonyloxy, (S)-1-fluorobutylcarbonyloxy, 2-fluorobutylcarbonyloxy, 3-fluorobutylcarbonyloxy, 4-fluorobutylcarbonyloxy, 1,1-difluorobutylcarbonyloxy, 2,2-difluorobutylcarbonyloxy, 3,3-difluorobutylcarbonyloxy, 4,4-difluorobutylcarbonyloxy, 4,4,4-trifluorobutylcarbonyloxy, etc.;

fluorinated $C_1$-$C_6$ alkylthio is a radical of the formula R—S—, wherein R is a fluorinated alkyl radical having from 1 to 6 carbon atoms as defined above. Examples comprise fluoromethylthio, difluoromethylthio, trifluoromethylthio, (R)-1-fluoroethylthio, (S)-1-fluoroethylthio, 2-fluoroethylthio, 1,1-difluoroethylthio, 2,2-difluoroethylthio, 2,2,2-trifluoroethylthio, (R)-1-fluoropropylthio, (S)-1-fluoropropylthio, 2-fluoropropylthio, 3-fluoropropylthio, 1,1-difluoropropylthio, 2,2-difluoropropylthio, 3,3-difluoropropylthio, 3,3,3-trifluoropropylthio, (R)-2-fluoro-1-methylethylthio, (S)-2-fluoro-1-methylethylthio, (R)-2,2-difluoro-1-methylethylthio, (S)-2,2-difluoro-1-methylethylthio, (R)-1,2-difluoro-1-methylethylthio, (S)-1,2-difluoro-1-methylethylthio, (R)-2,2,2-trifluoro-1-methylethylthio, (S)-2,2,2-trifluoro-1-methylethylthio, 2-fluoro-1-(fluoromethyl)ethylthio, 1-(difluoromethyl)-2,2-difluoroethylthio, (R)-1-fluorobutylthio, (S)-1-fluorobutylthio, 2-fluorobutylthio, 3-fluorobutylthio, 4-fluorobutylthio, 1,1-difluorobutylthio, 2,2-difluorobutylthio, 3,3-difluorobutylthio, 4,4-difluorobutylthio, 4,4,4-trifluorobutylthio, etc.;

fluorinated $C_1$-$C_6$ alkylsulfinyl is a radical of the formula R—S(O)—, wherein R is a fluorinated alkyl radical having from 1 to 6 carbon atoms as defined above. Examples comprise fluoromethylsulfinyl, difluoromethylsulfinyl, trifluoromethylsulfinyl, (R)-1-fluoroethylsulfinyl, (S)-1-fluoroethylsulfinyl, 2-fluoroethylsulfinyl, 1,1-difluoroethylsulfinyl, 2,2-difluoroethylsulfinyl, 2,2,2-trifluoroethylsulfinyl, (R)-1-fluoropropylsulfinyl, (S)-1-fluoropropylsulfinyl, 2-fluoropropylsulfinyl, 3-fluoropropylsulfinyl, 1,1-difluoropropylsulfinyl, 2,2-difluoropropylsulfinyl, 3,3-difluoropropylsulfinyl, 3,3,3-trifluoropropylsulfinyl, (R)-2-fluoro-1-methylethylsulfinyl, (S)-2-fluoro-1-methylethylsulfinyl, (R)-2,2-difluoro-1-methylethylsulfinyl, (S)-2,2-difluoro-1-methylethylsulfinyl, (R)-1,2-difluoro-1-methylethylsulfinyl, (S)-1,2-difluoro-1-methylethylsulfinyl, (R)-2,2,2-trifluoro-1-methylethylsulfinyl, (S)-2,2,2-trifluoro-1-methylethylsulfinyl, 2-fluoro-1-(fluoromethyl)ethylsulfinyl, 1-(difluoromethyl)-2,2-difluoroethylsulfinyl, (R)-1-fluorobutylsulfinyl, (S)-1-fluorobutylsulfinyl, 2-fluorobutylsulfinyl, 3-fluorobutylsulfinyl, 4-fluorobutylsulfinyl, 1,1-difluorobutylsulfinyl, 2,2-difluorobutylsulfinyl, 3,3-difluorobutylsulfinyl, 4,4-difluorobutylsulfinyl, 4,4,4-trifluorobutylsulfinyl, etc.;

fluorinated $C_1$-$C_6$ alkylsulfonyl is a radical of the formula R—S(O)$_2$—, wherein R is a fluorinated alkyl radical having from 1 to 6 carbon atoms as defined above. Examples comprise fluoromethylsulfonyl, difluoromethylsulfinyl, trifluoromethylsulfonyl, (R)-1-fluoromethylsulfonyl, (S)-1-fluoromethylsulfonyl, 2-fluoromethylsulfonyl, 1,1-difluoroethylsulfonyl, 2,2-difluoroethylsulfonyl, 2,2,2-trifluoroethylsulfonyl, (R)-1-fluoropropylsulfonyl, (S)-1-fluoropropylsulfonyl, 2-fluoropropylsulfonyl, 3-fluoropropylsulfonyl, 1,1-difluoropropylsulfonyl, 2,2-difluoropropylsulfonyl, 3,3-difluoropropylsulfonyl, 3,3,3-trifluoropropylsulfonyl, (R)-2-fluoro-1-methylethylsulfonyl, (S)-2-fluoro-1-methylethylsulfonyl, (R)-2,2-difluoro-1-methylethylsulfonyl, (S)-2,2-difluoro-1-methylethylsulfonyl, (R)-1,2-difluoro-1-methylethylsulfonyl, (S)-1,2-difluoro-1-methylethylsulfonyl, (R)-2,2,2-trifluoro-1-methylethylsulfonyl, (S)-2,2,2-trifluoro-1-methylethylsulfonyl, 2-fluoro-1-(fluoromethyl)ethylsulfonyl, 1-(difluoromethyl)-2,2-difluoroethylsulfonyl, (R)-1-fluorobutylsulfonyl, (S)-1-fluorobutylsulfonyl, 2-fluorobutylsulfonyl, 3-fluorobutylsulfonyl, 4-fluorobutylsulfonyl, 1,1-difluorobutylsulfonyl, 2,2-difluorobutylsulfonyl, 3,3-difluorobutylsulfonyl, 4,4-difluorobutylsulfonyl, 4,4,4-trifluorobutylsulfonyl, etc.

3- to 7-membered heterocyclic radicals comprise saturated heterocyclic radicals, which generally have 3-, 4-, 5-, 6- or 7 ring forming atoms (ring members), unsaturated non-aromatic heterocyclic radicals, which generally have 5-, 6- or 7 ring forming atoms, and heteroaromatic radicals, which generally have 5-, 6- or 7 ring forming atoms. The heterocyclic radicals may be bound via a carbon atom (C-bound) or an nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of 3- to 7-membered, saturated heterocyclic radicals comprise 1- or 2-aziridinyl, 1-, 2-, 3-azetidinyl, 1-, 2-, or 3-pyrrolidinyl, 1-, 2-, 3- or 4-piperidinyl, 1-, 2- or 3-morpholinyl, 1-, 2- or 3-thiomorpholinyl, 1-, 2- or 3-piperazinyl, 1-, 2- or 4-oxazolidinyl, 1-, 3- or 4-isoxazolidinyl, 2-oxiranyl, 2- or 3-oxetanyl, 2- or 3-oxylanyl, 2-, 3- or 4-oxylanyl, 1,3-dioxolan-2- or 4-yl and the like, which may be unsubstituted or which may carry 1, 2 or 3 of the aforementioned radicals $R^a$ and/or $R^b$.

Unsaturated non-aromatic heterocyclic radicals, are heterocyclic radicals which generally have 5-, 6- or 7 ring forming atoms and which have 1 or 2 doublebonds that do not form an aromatic p-electron system. Examples are 2,3-dihydropyrrolyl, 3,4-dihydropyrrolyl, 2,3-dihydrofuranyl, 3,4-dihydrofuranyl, 2,3-dihydrothiophenyl, 3,4-dihydrothiophenyl, 1,2-dihydropyridinyl, 2,3-Dihydropyridiynl, 3,4-dihydropyridinyl, 1,2,3,4-tetrahydropyridinyl, 2,3,4,5-tetrahydropyridinyl, and the like.

5- or 6-membered heteroaromatic radicals are heteroaromatic cyclic radicals, wherein the cyclic radical has 5 or 6 atoms which form the ring (ring members) and wherein generally 1, 2, 3 or 4 ring member atoms are selected from O, S and N, the other ring member atoms being carbon atoms. The heteroaromatic radicals may be bound via a carbon atom (C-bound) or an nitrogen atom (N-bound). Preferred heteroaromatic radicals comprise 1 nitrogen atom as ring member atom and optionally 1, 2 or 3 further heteroatoms as ring members, which are selected, independently of each other from O, S and N. Likewise preferred heteroaromatic radicals comprise 1 heteroatom as ring member, which is selected from O, S and N, and optionally 1, 2 or 3 further nitrogen atoms as ring members. Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadiazolyl, [1,3,4]-oxadiazolyl, 4- or 5-[1,2,3]-thiadiazolyl, [1,2,5]-thiadiazolyl, 3- or 5-[1,2,4]-thiadiazolyl or [1,3,4]-thiadiazolyl, which may be unsubstituted or which may carry 1, 2 or 3 of the aforementioned radicals $R^a$ and/or $R^b$.

A skilled person will appreciate that the radical -E-SO$_2$—Ar may be bound to any of the carbon atoms of the phenyl part of the bicyclic moiety in formula I, thereby substituting a hydrogen atom. Preferably the radical -E-SO$_2$—Ar is not bound to a carbon atom, which is not adjacent to a bridgehead carbon atom of the bicyclic moiety.

Preferably, Ar is phenyl or an aromatic 5- or 6-membered C-bound heteroaromatic radical, comprising 1 nitrogen atom as ring member and 0, 1, 2 or 3 further heteroatoms, independently of each other, selected from O, S and N, as ring members which may be unsubstituted or which may carry 1, 2 or 3 of the aforementioned radicals $R^a$ and/or $R^b$. Amongst these heteroaromatic radicals those are preferred, which comprise 1, 2 or 3 nitrogen atoms and no further heteroatom as ring members, or 1 or 2 nitrogen atoms and 1 atom, selected from O and S, as ring members. However, thienyl and furyl are likewise preferred. Particularly preferred radicals Ar are 2- or 3-thienyl, 2-, 3- or 4-pyridyl, 2-, 4- or 5-pyrimidinyl, 2-, 3- or 5-thiazolyl, 1,2,4-triazol-3-yl, 1,2,3-triazol-4-yl, 1,3,4-thiadiazol-2-yl, in particular 2-thienyl, 2-pyrimidinyl, 5-pyrimidinyl, 2-pyridinyl and more particularly phenyl which may be unsubstituted or which may carry 1, 2 or 3 of the aforementioned radicals $R^a$ and/or $R^b$.

Preferably the aromatic radical Ar carries one radical $R^a$ and optionally one or two further radicals $R^b$ as mentioned above, $R^b$ being particularly selected from methyl, fluorinated methyl, halogen, more preferably from fluorine or chlorine.

The aforementioned 5-membered heteroaromatic radicals Ar preferably one radical $R^a$ in the 3-position (related to the position of the $SO_2$-radical) and optionally one or two further radicals $R^b$, which are preferably selected from halogen, in particular fluorine or chlorine.

Phenyl and the aforementioned 6-membered heteroaromatic radicals Ar preferably carry one radical $R^a$ in the 4-position (related to the position of the $SO_2$-radical) and optionally one or two further radicals $R^b$, which are preferably selected from halogen, in particular fluorine or chlorine.

In a very preferred embodiment of the invention Ar is phenyl that carries a radical $R^a$ in the 4-position of the phenyl ring and optionally 1 or 2 further radicals $R^b$, which are preferably selected from halogen, in particular from fluorine or chlorine.

In another preferred embodiment of the invention Ar is 2-pyrimidinyl that carries a radical $R^a$ in the 5-position of the pyrimidine ring and optionally 1 or 2 further radicals $R^b$, which are preferably selected from halogen, in particular from fluorine or chlorine.

In a further preferred embodiment of the invention Ar is 5-pyrimidinyl that carries a radical $R^a$ in the 2-position of the pyrimidine ring and optionally 1 or 2 further radicals $R^b$, which are preferably selected from halogen, in particular from fluorine or chlorine.

In a further preferred embodiment of the invention Ar is 2-thienyl that carries a radical $R^a$ in the 3-position of the thiophen ring and optionally 1 or 2 further radicals $R^b$, which are preferably selected from halogen, in particular from fluorine or chlorine.

In a preferred embodiment Ar carries 1 radical $R^a$ which is selected from the group consisting of $C_2$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical, comprising 1 nitrogen atom as ring member and 0, 1, 2 or 3 further heteroatoms, independently of each other, selected from O, S and N, wherein the last two mentioned radicals may carry 1, 2, 3 or 4 radicals selected from halogen and the radicals $R^a$; and wherein Ar may carry 1 or 2 further radicals $R^b$, which are independently from each other selected from halogen, cyano, methyl, fluoromethyl, difluoromethyl, trifluoromethyl, difluoromethoxy and trifluoromethoxy. In this embodiment $R^4$, $R^5$ are, independently of each other, preferably selected from H, $C_1$-$C_2$-alkyl and fluorinated $C_1$-$C_2$-alkyl. Preferably one of the radicals $R^4$ or $R^5$ is different from hydrogen. One of the radicals $R^4$ or $R^5$ may also be $C_1$-$C_2$-alkoxy.

In a very preferred embodiment, the radical Ar preferably carries one radical $R^a$, which has the formula $R^{a'}$

wherein
Y is N, CH or CF,
$R^{a1}$ and $R^{a2}$ are independently of each other selected from $C_1$-$C_2$-alkyl, $C_1$-$C_2$-alkoxy, fluorinated $C_1$-$C_2$-alkyl, provided for Y being CH or CF one of the radicals $R^{a1}$ or $R^{a2}$ may also be hydrogen or fluorine, or
$R^{a1}$ and $R^{a2}$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety may be replaced by O, S, S=O, $SO_2$ or N—$R^c$, $R^c$ being hydrogen or $C_1$-$C_2$-alkyl and wherein m is 2, 3, 4, 5 or 6;
In particular
$R^{a1}$ or $R^{a2}$ may also be hydrogen or fluorine $R^{a1}$ and $R^{a2}$ are independently of each other selected from $C_1$-$C_2$-alkyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or
$R^{a1}$ and $R^{a2}$ form a radical $(CH_2)_k$ wherein 1 or 2 of the hydrogen atoms may be replaced by fluorine and wherein k is 2, 3 or 4, in particular $CH_2$—$CH_2$, CHF—$CH_2$ $CF_2$—$CH_2$, $CH_2$—$CH_2$—$CH_2$, CHF—$CH_2$—$CH_2$, $CF_2$—$CH_2$—$CH_2$, $CH_2$—CHF—$CH_2$, $CH_2$—$CF_2$—$CH_2$.

In case $R^{a1}$ and $R^{a2}$ are different from each other, the radical of the aforementioned formula $R^{a'}$ may have either (R)- or (S)-configuration with regard to the Y-moiety.

Examples for preferred radicals $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl cyclopropyl, cyclobutyl, 1-fluorocyclopropyl, and 2-fluorocyclopropyl Also preferred are radicals $R^{a'}$ wherein one of $R^{a1}$ or $R^{a2}$ is $C_1$-$C_2$-alkoxy and the other other of $R^{a1}$ or $R^{a2}$ is selected from H, $C_1$-$C_2$-alkyl, in particular methyl, fluorinated $C_1$-$C_2$-alkyl, in particular fluoromethyl, difluoromethyl or trifluoromethyl. Examples comprise N-methoxy-N-methylamino, N-methoxyamino and N-ethoxyamino.

Preferred radicals of the formula $R^{a'}$ also comprise those wherein Y is nitrogen and wherein $R^{a1}$ and $R^{a2}$ form a radical $(CH_2)_m$ wherein 1 or 2 of the hydrogen atoms may be replaced by fluorine, methyl, trifluoromethyl, methoxy or oxo and wherein m is 2, 3, 4 or 5. Examples comprise azetidin-1-yl, 2-methylazetidin-1-yl, (S)-2-methylazetidin-1-yl, (R)-2-methylazetidin-1-yl, 3-fluoroazetidin-1-yl, 3-methoxyazetidin- 1-yl, 3-hydroxyazetidin-1-yl, pyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 2,2-dimethylpyrrolidine-1-yl, 3,3-dimethylpyrrolidine-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, piperidin-1-yl, 2-methylpiperidin-1-yl, (S)-2-methylpiperidin-1-yl and (R)-2-methylpiperidin-1-yl.

Likewise preferred are radicals $R^{a'}$, wherein $R^{a1}$ and $R^{a2}$ together form a radical $(CH_2)_m$ wherein 1 or 2 of the hydrogen atoms may be replaced by fluorine, hydroxy, oxo, $C_1$-$C_2$-alkyl or $C_1$-$C_2$-alkoxy, wherein one $CH_2$ moiety is replaced by O, S, S=O, $SO_2$ or N—$R^c$, $R^c$ being hydrogen or $C_1$-$C_2$-alkyl and wherein m is 2, 3, 4, 5 or 6. Examples for preferred radicals of the formula $R^{a'}$ also comprise 4-morpholinyl, 4-thiomorpholinyl, 4-(1,1-dioxo)thiomorpholinyl, piperazin-1-yl, 4-methylpiperazin-1-yl, 2-oxo-oxazolidin-3-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl and (R)-1-methylpyrrolidin-3-yl.

Amongst the radicals of the formula $R^{a'}$ those are preferred which carry 1, 2, 3 or 4, in particular 1, 2 or 3 fluorine atoms.

In a further preferred embodiment Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl. Amongst these radicals $R^a$, preference is given to radicals selected from 2-, 3-, or 4-pyridyl, 2-, 4- or 5-pyrimidinyl, pyrazinyl, 3-, 4-pyridazinyl, 2- or 3-thienyl, 2- or 3-furyl, 1-, 2- or 3-pyrrolyl, 1-, 2- or 4-imidazolyl, 1-, 3- or 4-pyrazolyl, 1- or 3-[1,2,4]-triazolyl, 1- or 4-[1,2,3]-triazolyl, 1-, 2- or 5-tetrazolyl, 2-, 3- or 5-oxazolyl, 3-, 4- or 5-isoxazolyl, 2-, 3- or 5-thiazolyl, 3-, 4- or 5-isothiazolyl, 4- or 5-[1,2,3]-oxadiazolyl, [1,2,5]-oxadiazolyl (=furazanyl), 3- or 5-[1,2,4]-oxadiazolyl, [1,3,4]-oxadiazolyl, 4- or 5-[1,2,3]-thiadiazolyl, [1,2,5]-thiadiazolyl, 3- or 5-[1,2,4]-thiadiazolyl or [1,3,4]-thiadiazolyl, in particular from 2- or 3-furanyl, 2- or 3-thienyl, 1-, 2- or 3-pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents as given above. Preferred substituents on heteroaromatic $R^a$ are selected from halogen, $C_1$-$C_4$-alkyl, $C_1$-$C_4$-alkoxy, fluorinated $C_1$-$C_4$-alkyl and fluorinated $C_1$-$C_4$-alkoxy.

In a further preferred embodiment Ar carries 1 radical $R^a$ which selected from the group consisting of $CHF_2$, $CH_2F$, $OCHF_2$ and $OCH_2F$, with $OCHF_2$ being preferred. In this embodiment Ar may also carry 1 or 2 further radicals $R^b$, which are independently from each other selected from halogen, cyano, methyl, fluoromethyl, difluoromethyl, trifluoromethyl, difluoromethoxy and trifluoromethoxy. Preferably Ar carries no further radical $R^b$. In this embodiment Ar is preferably phenyl which carries 1 radical $R^a$ which selected from the group consisting of $CHF_2$, $CH_2F$, $OCHF_2$ and $OCH_2F$, with $OCHF_2$ being preferred. In this embodiment Ar is preferably phenyl, which carries $R^a$ in the 4 position with respect to the $SO_2$-group.

In another embodiment of the invention, Ar carries 1 radical $R^a$ which selected from the group consisting of $C_2$-$C_6$-alkenyl, fluorinated $C_2$-$C_6$-alkenyl, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $CH_2NR^4R^5$, $ONR^4R^5$, $NHC(O)NR^4R^5$, $C(O)NR^4R^5$, $SO_2NR^4R^5$, $C_1$-$C_6$-alkylcarbonyl, fluorinated $C_2$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenoxy, benzyloxy and a 5- or 6-membered N-bound heteroaromatic radical, wherein the four last mentioned radicals may carry 1, 2, 3 or 4 radicals selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_2$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated, $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

In another embodiment of the invention, Ar is phenyl, which carries 1 radical $R^a$ and at least one radical $R^b$ and wherein $R^a$ and one radical $R^b$ are bound to two adjacent carbon atoms of phenyl and form a 5- or 6-membered heterocyclic or carbocyclic ring which is fused to the phenyl ring and which is unsubstituted or which may carry 1, 2 or 3 radicals as given above. Examples of a phenyl ring fused to a saturated or unsaturated 5- or 6-membered carbocyclic or heterocyclic ring comprise indenyl, indanyl, naphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals. Preferred substituents for the saturated or unsaturated 5- or 6-membered carbocyclic or heterocyclic ring fused to the phenyl ring are selected from halogen, $C_1$-$C_4$-alkyl, $C_1$-$C_4$-alkoxy, fluorinated $C_1$-$C_4$-alkyl and fluorinated $C_1$-$C_4$-alkoxy.

The radical $R^1$ is preferably $C_2$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl, in particular $C_2$-$C_4$-alkyl, $C_3$-$C_4$-alkenyl, fluorinated $C_2$-$C_4$-alkyl, fluorinated $C_3$-$C_4$-alkenyl, more preferably n-propyl, fluorinated $C_2$-$C_3$-alkyl or 1-propen-3-yl, in particular n-propyl.

A first preferred embodiment of the invention relates to compounds, wherein $R^{1a}$ is hydrogen. In these compounds $R^1$ has the meanings given above. In particular $R^1$ is n-propyl. In this embodiment $R^{2a}$ is preferably hydrogen while $R^2$ is preferably hydrogen, methyl or fluorinated methyl. In particular, both $R^{2a}$ and $R^2$ are hydrogen or one of the radicals $R^{2a}$ and $R^2$ is hydrogen while the other is methyl.

In a second preferred embodiment, $R^{1a}$ is different from hydrogen and preferably $C_2$-$C_4$-alkyl, $C_3$-$C_4$-alkenyl, fluorinated $C_2$-$C_4$-alkyl, fluorinated $C_3$-$C_4$-alkenyl, more preferably n-propyl, fluorinated $C_2$-$C_3$-alkyl or 1-propen-3-yl, in particular n-propyl In these compounds $R^1$ has the meanings given above. In particular $R^1$ is n-propyl. In this embodiment $R^{2a}$ is preferably hydrogen while $R^2$ is preferably hydrogen, methyl or fluorinated methyl. In particular both $R^{2a}$ and $R^2$ are hydrogen or, one of the radicals $R^{2a}$ and $R^2$ is hydrogen while the other is methyl.

In a third preferred embodiment, $R^{2a}$ and $R^{1a}$ together are $(CH_2)_n$ with n being 3 or 4. $R^2$ is preferably hydrogen. In these compounds $R^1$ has the meanings given above. In particular $R^1$ is n-propyl, 1-propen-3-yl.

One preferred embodiment of the invention, relates to compounds of the formula I, wherein X is CH. Another embodiment of the invention, relates to compounds of the formula I, wherein X is N.

Preferably the moiety E is N—$R^3$, wherein $R^3$ is as defined above. $R^3$ is in particular H or methyl and most preferred H. If E is a moiety $CR^6R^7$, preferably one and in particular both of the radicals $R^6$ and $R^7$ are hydrogen.

Preferred embodiments of the invention are compounds of the following formulae Ia, Ib, Ic, Id, Ie, If, Ig, Ih, Ii, Ik, Im, In, Io, Ip, Iq, Ir, Is, It, Iu and Iv and to the physiologically tolerated acid addition salts thereof. With regard to the carbon atom carrying the $NR^1$-group, compounds of the formulae Ic, Id, Ii, Ik, Io, Ip, Iu and Iv may exist as R-enantiomers or S-enantiomers as well as mixtures of the enantiomers such as racemic mixtures. The preferred embodiments include the R- and S-enantiomers of Ic, Id, Ii, Ik, Io, Ip, Iu and Iv and the mixtures of the enantiomers.

In the compounds of the formulae Ia, Ib, Ic, Id, Ie, If, Ig, Ih, Ii, Ik, Im, In, Io, Ip, Iq, Ir, Is, It, Iu and Iv $R^1$, Ar and $R^{1a}$ are as defined above with particular preference given to those compounds wherein $R^1$, Ar and $R^{1a}$ have one of the preferred meanings.

Ia
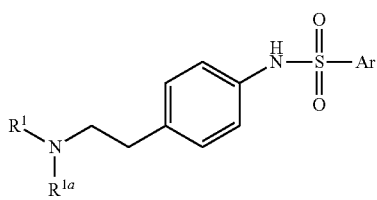

Ib
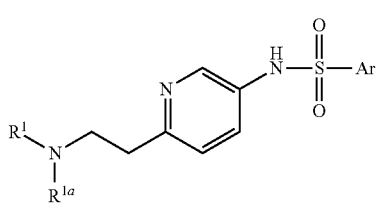

Ic
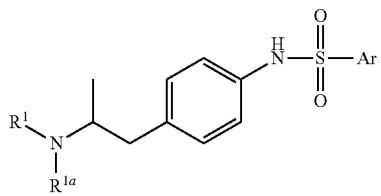

Id
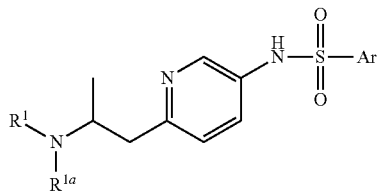

Ie
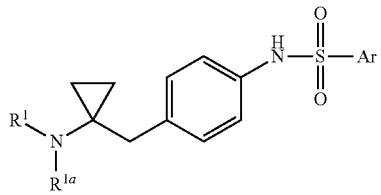

If
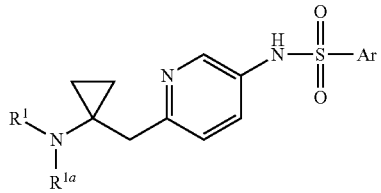

Ig
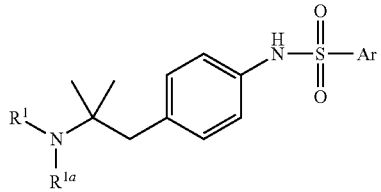

Ih
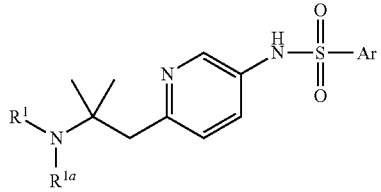

Ii
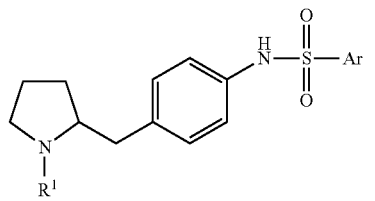

Ik

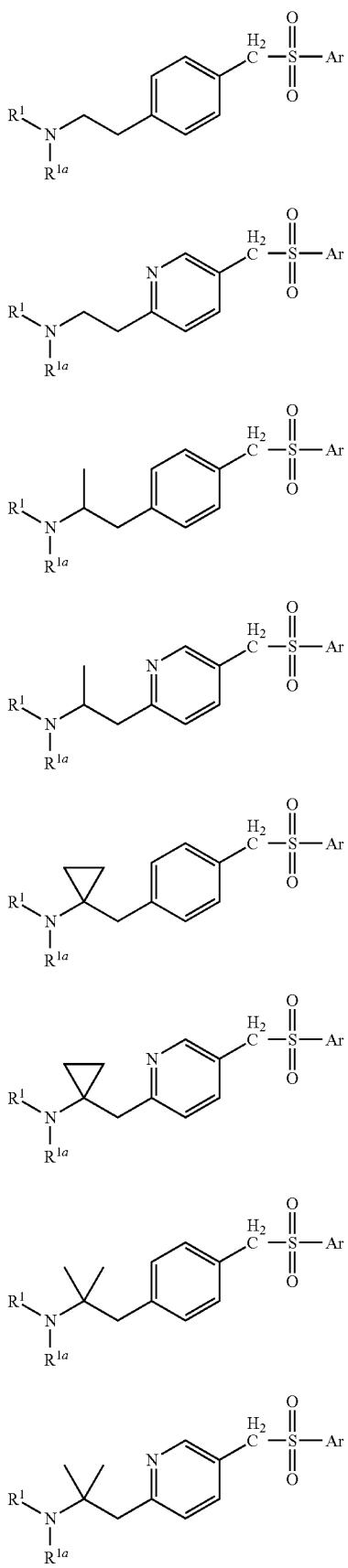

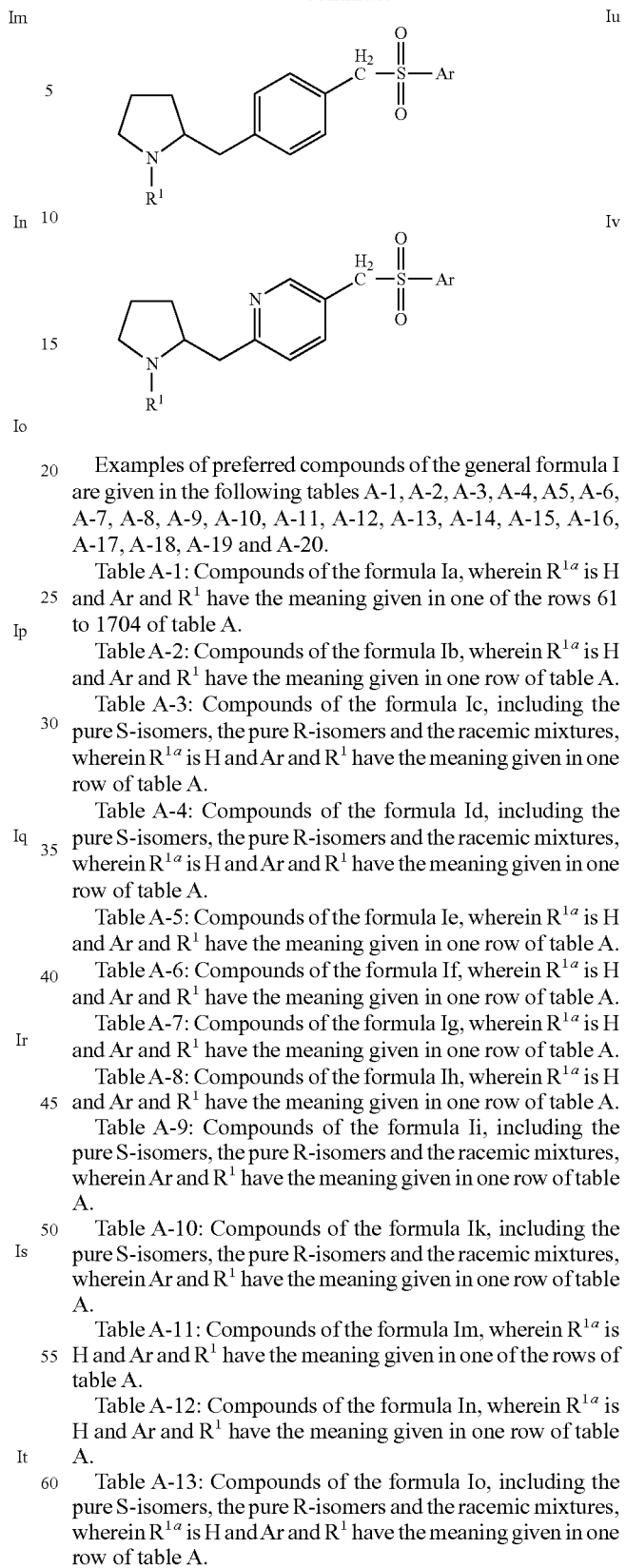

Examples of preferred compounds of the general formula I are given in the following tables A-1, A-2, A-3, A-4, A5, A-6, A-7, A-8, A-9, A-10, A-11, A-12, A-13, A-14, A-15, A-16, A-17, A-18, A-19 and A-20.

Table A-1: Compounds of the formula Ia, wherein $R^{1a}$ is H and Ar and $R^1$ have the meaning given in one of the rows 61 to 1704 of table A.

Table A-2: Compounds of the formula Ib, wherein $R^{1a}$ is H and Ar and $R^1$ have the meaning given in one row of table A.

Table A-3: Compounds of the formula Ic, including the pure S-isomers, the pure R-isomers and the racemic mixtures, wherein $R^{1a}$ is H and Ar and $R^1$ have the meaning given in one row of table A.

Table A-4: Compounds of the formula Id, including the pure S-isomers, the pure R-isomers and the racemic mixtures, wherein $R^{1a}$ is H and Ar and $R^1$ have the meaning given in one row of table A.

Table A-5: Compounds of the formula Ie, wherein $R^{1a}$ is H and Ar and $R^1$ have the meaning given in one row of table A.

Table A-6: Compounds of the formula If, wherein $R^{1a}$ is H and Ar and $R^1$ have the meaning given in one row of table A.

Table A-7: Compounds of the formula Ig, wherein $R^{1a}$ is H and Ar and $R^1$ have the meaning given in one row of table A.

Table A-8: Compounds of the formula Ih, wherein $R^{1a}$ is H and Ar and $R^1$ have the meaning given in one row of table A.

Table A-9: Compounds of the formula Ii, including the pure S-isomers, the pure R-isomers and the racemic mixtures, wherein Ar and $R^1$ have the meaning given in one row of table A.

Table A-10: Compounds of the formula Ik, including the pure S-isomers, the pure R-isomers and the racemic mixtures, wherein Ar and $R^1$ have the meaning given in one row of table A.

Table A-11: Compounds of the formula Im, wherein $R^{1a}$ is H and Ar and $R^1$ have the meaning given in one of the rows of table A.

Table A-12: Compounds of the formula In, wherein $R^{1a}$ is H and Ar and $R^1$ have the meaning given in one row of table A.

Table A-13: Compounds of the formula Io, including the pure S-isomers, the pure R-isomers and the racemic mixtures, wherein $R^{1a}$ is H and Ar and $R^1$ have the meaning given in one row of table A.

Table A-14: Compounds of the formula Ip, including the pure S-isomers, the pure R-isomers and the racemic mixtures, wherein $R^{1a}$ is H and Ar and $R^1$ have the meaning given in one row of table A.

Table A-15: Compounds of the formula Iq, wherein $R^{1a}$ is H and Ar and $R^1$ have the meaning given in one row of table A.

Table A-16: Compounds of the formula Ir, wherein $R^{1a}$ is H and Ar and $R^1$ have the meaning given in one row of table A.

Table A-17: Compounds of the formula Is, wherein $R^{1a}$ is H and Ar and $R^1$ have the meaning given in one row of table A.

Table A-18: Compounds of the formula It, wherein $R^{1a}$ is H and Ar and $R^1$ have the meaning given in one row of table A.

Table A-19: Compounds of the formula Iu, including the pure S-isomers, the pure R-isomers and the racemic mixtures, wherein Ar and $R^1$ have the meaning given in one row of table A.

Table A-20: Compounds of the formula Iv, including the pure S-isomers, the pure R-isomers and the racemic mixtures, wherein Ar and $R^1$ have the meaning given in one row of table A.

TABLE A

| No. | $R^1$ | Ar |
|---|---|---|
| 1. | methyl | 4-(trifluoromethoxy)-phenyl |
| 2. | methyl | 3-(trifluoromethoxy)-phenyl |
| 3. | methyl | 4-cyanophenyl |
| 4. | methyl | 4-methylphenyl |
| 5. | methyl | 4-ethylphenyl |
| 6. | methyl | 4-propylphenyl |
| 7. | methyl | 4-methoxyphenyl |
| 8. | methyl | 4-fluorophenyl |
| 9. | methyl | 4-chlorophenyl |
| 10. | methyl | 4-bromophenyl |
| 11. | methyl | 3-(trifluoromethyl)phenyl |
| 12. | methyl | 4-(trifluoromethyl)phenyl |
| 13. | methyl | 2-(trifluoromethyl)phenyl |
| 14. | methyl | 3,4-difluorophenyl |
| 15. | methyl | 4-bromo-3-fluorophenyl |
| 16. | methyl | 4-bromo-2-fluorophenyl |
| 17. | methyl | 4-bromo-2,5-difluorophenyl |
| 18. | methyl | 2-fluoro-4-isopropylphenyl |
| 19. | methyl | 4-methylsulfanyl |
| 20. | methyl | 4-hydroxyphenyl |
| 21. | ethyl | 4-(trifluoromethoxy)-phenyl |
| 22. | ethyl | 3-(trifluoromethoxy)-phenyl |
| 23. | ethyl | 4-cyanophenyl |
| 24. | ethyl | 4-methylphenyl |
| 25. | ethyl | 4-ethylphenyl |
| 26. | ethyl | 4-propylphenyl |
| 27. | ethyl | 4-methoxyphenyl |
| 28. | ethyl | 4-fluorophenyl |
| 29. | ethyl | 4-chlorophenyl |
| 30. | ethyl | 4-bromophenyl |
| 31. | ethyl | 3-(trifluoromethyl)phenyl |
| 32. | ethyl | 4-(trifluoromethyl)phenyl |
| 33. | ethyl | 2-(trifluoromethyl)phenyl |
| 34. | ethyl | 3,4-difluorophenyl |
| 35. | ethyl | 4-bromo-3-fluorophenyl |
| 36. | ethyl | 4-bromo-2-fluorophenyl |
| 37. | ethyl | 4-bromo-2,5-difluorophenyl |
| 38. | ethyl | 2-fluoro-4-isopropylphenyl |
| 39. | ethyl | 4-methylsulfanyl |
| 40. | ethyl | 4-hydroxyphenyl |
| 41. | propyl | 4-(trifluoromethoxy)-phenyl |
| 42. | propyl | 3-(trifluoromethoxy)-phenyl |
| 43. | propyl | 4-cyanophenyl |
| 44. | propyl | 4-methylphenyl |
| 45. | propyl | 4-ethylphenyl |
| 46. | propyl | 4-propylphenyl |
| 47. | propyl | 4-methoxyphenyl |
| 48. | propyl | 4-fluorophenyl |
| 49. | propyl | 4-chlorophenyl |
| 50. | propyl | 4-bromophenyl |
| 51. | propyl | 3-(trifluoromethyl)phenyl |
| 52. | propyl | 4-(trifluoromethyl)phenyl |
| 53. | propyl | 2-(trifluoromethyl)phenyl |
| 54. | propyl | 3,4-difluorophenyl |
| 55. | propyl | 4-bromo-3-fluorophenyl |
| 56. | propyl | 4-bromo-2-fluorophenyl |
| 57. | propyl | 4-bromo-2,5-difluorophenyl |
| 58. | propyl | 2-fluoro-4-isopropylphenyl |
| 59. | propyl | 4-methylsulfanyl |
| 60. | propyl | 4-hydroxyphenyl |
| 61. | propyl | 4-isopropylphenyl |
| 62. | propyl | 4-sec-butylphenyl |
| 63. | propyl | 4-isobutylphenyl |
| 64. | propyl | 4-(1,1-dimethylpropyl)-phenyl |
| 65. | propyl | 4-vinylphenyl |

TABLE A-continued

| No. | R¹ | Ar |
|---|---|---|
| 66. | propyl | 4-isopropenylphenyl |
| 67. | propyl | 4-(fluoromethyl)phenyl |
| 68. | propyl | 3-(fluoromethyl)phenyl |
| 69. | propyl | 2-(fluoromethyl)phenyl |
| 70. | propyl | 4-(difluoromethyl)phenyl |
| 71. | propyl | 3-(difluoromethyl)phenyl |
| 72. | propyl | 2-(difluoromethyl)phenyl |
| 73. | propyl | 4-(1-fluoroethyl)-phenyl |
| 74. | propyl | 4-((S)-1-fluoroethyl)-phenyl |
| 75. | propyl | 4-((R)-1-fluoroethyl)-phenyl |
| 76. | propyl | 4-(2-fluoroethyl)-phenyl |
| 77. | propyl | 4-(1,1-difluoroethyl)-phenyl |
| 78. | propyl | 4-(2,2-difluoroethyl)-phenyl |
| 79. | propyl | 4-(2,2,2-trifluoroethyl)-phenyl |
| 80. | propyl | 4-(3-fluoropropyl)-phenyl |
| 81. | propyl | 4-(2-fluoropropyl)-phenyl |
| 82. | propyl | 4-((S)-2-fluoropropyl)-phenyl |
| 83. | propyl | 4-((R)-2-fluoropropyl)-phenyl |
| 84. | propyl | 4-(3,3-difluoropropyl)-phenyl |
| 85. | propyl | 4-(3,3,3-trifluoropropyl)-phenyl |
| 86. | propyl | 4-(1-fluoro-1-methylethyl)-phenyl |
| 87. | propyl | 4-(2-fluoro-1-methylethyl)-phenyl |
| 88. | propyl | 4-((S)-2-fluoro-1-methylethyl)-phenyl |
| 89. | propyl | 4-((R)-2-fluoro-1-methylethyl)-phenyl |
| 90. | propyl | 4-(2,2-difluoro-1-methylethyl)-phenyl |
| 91. | propyl | 4-((S)-2,2-difluoro-1-methylethyl)-phenyl |
| 92. | propyl | 4-((R)-2,2-difluoro-1-methylethyl)-phenyl |
| 93. | propyl | 4-(2,2,2-trifluoro-1-methylethyl)-phenyl |
| 94. | propyl | 4-((S)-2,2,2-trifluoro-1-methylethyl)-phenyl |
| 95. | propyl | 4-((R)-2,2,2-trifluoro-1-methylethyl)-phenyl |
| 96. | propyl | 4-(2-fluoro-1-fluoromethylethyl)-phenyl |
| 97. | propyl | 4-(1-difluoromethyl-2,2-difluoroethyl)-phenyl |
| 98. | propyl | 4-(1,1-dimethyl-2-fluoroethyl)-phenyl |
| 99. | propyl | 4-ethoxyphenyl |
| 100. | propyl | 4-propoxyphenyl |
| 101. | propyl | 4-isopropoxyphenyl |
| 102. | propyl | 4-butoxyphenyl |
| 103. | propyl | 4-(fluoromethoxy)-phenyl |
| 104. | propyl | 4-(difluoromethoxy)-phenyl |
| 105. | propyl | 4-(2-fluoroethoxy)-phenyl |
| 106. | propyl | 4-(2,2-difluoroethoxy)-phenyl |
| 107. | propyl | 4-(2,2,2-trifluoroethoxy)-phenyl |
| 108. | propyl | 4-(1,1,2,2-tetrafluoroethoxy)-phenyl |
| 109. | propyl | 4-cyclopropylphenyl |
| 110. | propyl | 4-cyclobutylphenyl |
| 111. | propyl | 4-cyclopentylphenyl |
| 112. | propyl | 4-(2,2-difluorocyclopropyl)-phenyl |
| 113. | propyl | 2-fluoro-4-isopropylphenyl |
| 114. | propyl | 3-fluoro-4-isopropylphenyl |
| 115. | propyl | 4-(1-hydroxy-1-methylethyl)-phenyl |
| 116. | propyl | 4-(2-hydroxy-2-methylpropyl)-phenyl |
| 117. | propyl | 4-acetylphenyl |
| 118. | propyl | 4-carboxyphenyl |
| 119. | propyl | 4-(O-benzyl)-phenyl |
| 120. | propyl | 4-(2-methoxyethoxy)-phenyl |
| 121. | propyl | 4-(CH$_2$—N(CH$_3$)$_2$)-phenyl |
| 122. | propyl | 4-(NH—CO—NH$_2$)-phenyl |
| 123. | propyl | 4-(fluoromethylsulfanyl)-phenyl |
| 124. | propyl | 4-(difluoromethylsulfanyl)-phenyl |
| 125. | propyl | 4-(trifluoromethylsulfanyl)-phenyl |
| 126. | propyl | 4-(methylsulfonyl)-phenyl |
| 127. | propyl | 4-(N-methoxy-N-methyl-amino)-phenyl |
| 128. | propyl | 4-(methoxyamino)-phenyl |
| 129. | propyl | 4-(ethoxyamino)-phenyl |
| 130. | propyl | 4-(N-methylaminooxy)-phenyl |
| 131. | propyl | 4-(N,N-dimethylaminooxy)-phenyl |
| 132. | propyl | 4-(azetidin-1-yl)-phenyl |
| 133. | propyl | 4-(2-methylazetidin-1-yl)-phenyl |
| 134. | propyl | 4-((S)-2-methylazetidin-1-yl)-phenyl |
| 135. | propyl | 4-((R)-2-methylazetidin-1-yl)-phenyl |
| 136. | propyl | 4-(3-fluoroazetidin-1-yl)-phenyl |
| 137. | propyl | 4-(3-methoxyazetidin-1-yl)-phenyl |
| 138. | propyl | 4-(3-hydroxyazetidin-1-yl)-phenyl |
| 139. | propyl | 4-(pyrrolidin-1-yl)-phenyl |
| 140. | propyl | 4-(pyrrolidin-2-yl)-phenyl |
| 141. | propyl | 4-((S)-pyrrolidin-2-yl)-phenyl |
| 142. | propyl | 4-((R)-pyrrolidin-2-yl)-phenyl |
| 143. | propyl | 4-(pyrrolidin-3-yl)-phenyl |

TABLE A-continued

| No. | R¹ | Ar |
|---|---|---|
| 144. | propyl | 4-((S)-pyrrolidin-3-yl)-phenyl |
| 145. | propyl | 4-((R)-pyrrolidin-3-yl)-phenyl |
| 146. | propyl | 4-(2-fluoropyrrolidin-1-yl)-phenyl |
| 147. | propyl | 4-((S)-2-fluoropyrrolidin-1-yl)-phenyl |
| 148. | propyl | 4-((R)-2-fluoropyrrolidin-1-yl)-phenyl |
| 149. | propyl | 4-(3-fluoropyrrolidin-1-yl)-phenyl |
| 150. | propyl | 4-((S)-3-fluoropyrrolidin-1-yl)-phenyl |
| 151. | propyl | 4-((R)-3-fluoropyrrolidin-1-yl)-phenyl |
| 152. | propyl | 4-(2,2-difluoropyrrolidin-1-yl)-phenyl |
| 153. | propyl | 4-(3,3-difluoropyrrolidin-1-yl)-phenyl |
| 154. | propyl | 4-(2-methylpyrrolidin-1-yl)-phenyl |
| 155. | propyl | 4-((S)-2-methylpyrrolidin-1-yl)-phenyl |
| 156. | propyl | 4-((R)-2-methylpyrrolidin-1-yl)-phenyl |
| 157. | propyl | 4-(3-methylpyrrolidin-1-yl)-phenyl |
| 158. | propyl | 4-((S)-3-methylpyrrolidin-1-yl)-phenyl |
| 159. | propyl | 4-((R)-3-methylpyrrolidin-1-yl)-phenyl |
| 160. | propyl | 4-(1-methylpyrrolidin-2-yl)-phenyl |
| 161. | propyl | 4-((S)-1-methylpyrrolidin-2-yl)-phenyl |
| 162. | propyl | 4-((R)-1-methylpyrrolidin-2-yl)-phenyl |
| 163. | propyl | 4-(1-methylpyrrolidin-3-yl)-phenyl |
| 164. | propyl | 4-((S)-1-methylpyrrolidin-3-yl)-phenyl |
| 165. | propyl | 4-((R)-1-methylpyrrolidin-3-yl)-phenyl |
| 166. | propyl | 4-(2,2-dimethylpyrrolidin-1-yl)-phenyl |
| 167. | propyl | 4-(3,3-dimethylpyrrolidin-1-yl)-phenyl |
| 168. | propyl | 4-(2-trifluoromethylpyrrolidin-1-yl)-phenyl |
| 169. | propyl | 4-((S)-2-trifluoromethylpyrrolidin-1-yl)-phenyl |
| 170. | propyl | 4-((R)-2-trifluoromethylpyrrolidin-1-yl)-phenyl |
| 171. | propyl | 4-(3-trifluoromethylpyrrolidin-1-yl)-phenyl |
| 172. | propyl | 4-((S)-3-trifluoromethylpyrrolidin-1-yl)-phenyl |
| 173. | propyl | 4-((R)-3-trifluoromethylpyrrolidin-1-yl)-phenyl |
| 174. | propyl | 4-(2-oxopyrrolidin-1-yl)-phenyl |
| 175. | propyl | 4-(2-oxo-oxazolidin-3-yl)-phenyl |
| 176. | propyl | 4-(piperidin-1-yl)-phenyl |
| 177. | propyl | 4-(2-methylpiperidin-1-yl)-phenyl |
| 178. | propyl | 4-((S)-2-methylpiperidin-1-yl)-phenyl |
| 179. | propyl | 4-((R)-2-methylpiperidin-1-yl)-phenyl |
| 180. | propyl | 4-(piperazin-1-yl)-phenyl |
| 181. | propyl | 4-(4-methylpiperazin-1-yl)-phenyl |
| 182. | propyl | 4-(morpholin-4-yl)-phenyl |
| 183. | propyl | 4-(thiomorpholin-4-yl)-phenyl |
| 184. | propyl | 4-(1-oxo-thiomorpholin-4-yl)-phenyl |
| 185. | propyl | 4-(1,1-dioxo-thiomorpholin-4-yl)-phenyl |
| 186. | propyl | 4-(pyrrol-1-yl)-phenyl |
| 187. | propyl | 4-(pyrrol-2-yl)-phenyl |
| 188. | propyl | 4-(pyrrol-3-yl)-phenyl |
| 189. | propyl | 4-(1-methylpyrrol-2-yl)-phenyl |
| 190. | propyl | 4-(1-methylpyrrol-3-yl)-phenyl |
| 191. | propyl | 4-(furan-2-yl)-phenyl |
| 192. | propyl | 4-(furan-3-yl)-phenyl |
| 193. | propyl | 4-(thiophen-2-yl)-phenyl |
| 194. | propyl | 4-(thiophen-3-yl)-phenyl |
| 195. | propyl | 4-(5-propylthien-2-yl)-phenyl |
| 196. | propyl | 4-(pyrazol-1-yl)-phenyl |
| 197. | propyl | 4-(pyrazol-3-yl)-phenyl |
| 198. | propyl | 4-(pyrazol-4-yl)-phenyl |
| 199. | propyl | 4-(1-methyl-1H-pyrazol-4-yl)-phenyl |
| 200. | propyl | 4-(1-ethyl-1H-pyrazol-4-yl)-phenyl |
| 201. | propyl | 4-(1-methyl-1H-pyrazol-5-yl)-phenyl |
| 202. | propyl | 4-(1H-imidazol-2-yl)-phenyl |
| 203. | propyl | 4-(imidazol-1-yl)-phenyl |
| 204. | propyl | 4-(1-methylimidazol-2-yl)-phenyl |
| 205. | propyl | 4-(oxazol-2-yl)-phenyl |
| 206. | propyl | 4-(oxazol-4-yl)-phenyl |
| 207. | propyl | 4-(oxazol-5-yl)-phenyl |
| 208. | propyl | 4-(isoxazol-3-yl)-phenyl |
| 209. | propyl | 4-(isoxazol-4-yl)-phenyl |
| 210. | propyl | 4-(isoxazol-5-yl)-phenyl |
| 211. | propyl | 4-([1,2,3]-triazol-1-yl)-phenyl |
| 212. | propyl | 4-([1,2,4]-triazol-1-yl)-phenyl |
| 213. | propyl | 4-([1,2,3]-triazol-2-yl)-phenyl |
| 214. | propyl | 4-(4H-[1,2,4]-triazol-3-yl)-phenyl |
| 215. | propyl | 4-([1,2,4]-triazol-4-yl)-phenyl |
| 216. | propyl | 4-(2H-[1,2,3]-triazol-4-yl)-phenyl |
| 217. | propyl | 4-(4-methyl-4H-[1,2,4]-triazol-3-yl)-phenyl |
| 218. | propyl | 4-(2-methyl-2H-[1,2,3]-triazol-4-yl)-phenyl |
| 219. | propyl | 4-([1,3,4]-oxadiazol-2-yl)-phenyl |
| 220. | propyl | 4-([1,2,4]-oxadiazol-3-yl)-phenyl |
| 221. | propyl | 4-([1,2,4]-oxadiazol-5-yl)-phenyl |

TABLE A-continued

| No. | R¹ | Ar |
|---|---|---|
| 222. | propyl | 4-([1,2,3]-oxadiazol-4-yl)-phenyl |
| 223. | propyl | 4-([1,2,3]-oxadiazol-5-yl)-phenyl |
| 224. | propyl | 4-([1,2,3]-thiadiazol-4-yl)-phenyl |
| 225. | propyl | 4-(1H-tetrazol-5-yl)-phenyl |
| 226. | propyl | 4-(tetrazol-1-yl)-phenyl |
| 227. | propyl | 4-(2-methyl-2H-tetrazol-5-yl)-phenyl |
| 228. | propyl | 4-(1-methyl-1H-tetrazol-5-yl)-phenyl |
| 229. | propyl | 4-furazan-3-yl-phenyl |
| 230. | propyl | 4-(pyrid-2-yl)-phenyl |
| 231. | propyl | 4-(pyrid-3-yl)-phenyl |
| 232. | propyl | 4-(pyrid-4-yl)-phenyl |
| 233. | propyl | 4-(pyrimidin-2-yl)-phenyl |
| 234. | propyl | 4-(pyrimidin-4-yl)-phenyl |
| 235. | propyl | 4-(pyrimidin-5-yl)-phenyl |
| 236. | propyl | 5-isopropylthiophen-2-yl |
| 237. | propyl | 2-chlorothiophen-5-yl |
| 238. | propyl | 2,5-dichlorothiophen-4-yl |
| 239. | propyl | 2,3-dichlorothiophen-5-yl |
| 240. | propyl | 2-chloro-3-nitrothiophen-5-yl |
| 241. | propyl | 2-(phenylsulfonyl)-thiophen-5-yl |
| 242. | propyl | 2-(pyridin-2-yl)thiophen-5-yl |
| 243. | propyl | 2-(5-(trifluoromethyl)isoxazol-3-yl)-thiophen-5-yl |
| 244. | propyl | 2-(2-methylthiazol-4-yl)-thiophen-5-yl |
| 245. | propyl | 1-methyl-1H-imidazol-4-yl |
| 246. | propyl | 1,2-dimethyl-1H-imidazol-4-yl |
| 247. | propyl | 3,5-dimethylisoxazol-4-yl |
| 248. | propyl | thiazol-2-yl |
| 249. | propyl | 4-methylthiazol-2-yl |
| 250. | propyl | 4-isopropylthiazol-2-yl |
| 251. | propyl | 4-trifluoromethylthiazol-2-yl |
| 252. | propyl | 5-methylthiazol-2-yl |
| 253. | propyl | 5-isopropylthiazol-2-yl |
| 254. | propyl | 5-trifluoromethylthiazol-2-yl |
| 255. | propyl | 2,4-dimethylthiazol-5-yl |
| 256. | propyl | 2-acetamido-4-methylthiazol-5-yl |
| 257. | propyl | 4H-[1,2,4]triazol-3-yl |
| 258. | propyl | 5-methyl-4H-[1,2,4]triazol-3-yl |
| 259. | propyl | 4-methyl-4H-[1,2,4]triazol-3-yl |
| 260. | propyl | 5-isopropyl-4H-[1,2,4]triazol-3-yl |
| 261. | propyl | 5-trifluoromethyl-4H-[1,2,4]triazol-3-yl |
| 262. | propyl | 4,5-dimethyl-4H-[1,2,4]triazol-3-yl |
| 263. | propyl | 5-isopropyl-4-methyl-4H-[1,2,4]triazol-3-yl |
| 264. | propyl | 5-trifluoromethyl-4-methyl-4H-[1,2,4]triazol-3-yl |
| 265. | propyl | [1,3,4]thiadiazol-2-yl |
| 266. | propyl | 5-methyl-[1,3,4]thiadiazol-2-yl |
| 267. | propyl | 5-isopropyl-[1,3,4]thiadiazol-2-yl |
| 268. | propyl | 5-trifluoromethyl-[1,3,4]thiadiazol-2-yl |
| 269. | propyl | 3-bromo-2-chloropyrid-5-yl |
| 270. | propyl | 2-(4-morpholino)-pyrid-5-yl |
| 271. | propyl | 2-phenoxypyrid-5-yl |
| 272. | propyl | (2-isopropyl)-pyrimidin-5-yl |
| 273. | propyl | (5-isopropyl)-pyrimidin-2-yl |
| 274. | propyl | 8-quinolyl |
| 275. | propyl | 5-isoquinolyl |
| 276. | propyl | 2-(trifluoroacetyl)-1,2,3,4-tetrahydroisoquinolin-7-yl |
| 277. | propyl | 5-chloro-3-methylbenzothiophen-2-yl |
| 278. | propyl | 3,4-dihydro-4-methyl-2H-benzo[b][1,4]oxazinyl |
| 279. | propyl | benzothiazol-6-yl |
| 280. | propyl | benzo[2,1,3]oxadiazol-4-yl |
| 281. | propyl | 5-chlorobenzo[2,1,3]oxadiazol-4-yl |
| 282. | propyl | 7-chlorobenzo[2,1,3]oxadiazol-4-yl |
| 283. | propyl | benzo[2,1,3]thiadiazol-4-yl |
| 284. | ethyl | 4-isopropylphenyl |
| 285. | ethyl | 4-sec-butylphenyl |
| 286. | ethyl | 4-isobutylphenyl |
| 287. | ethyl | 4-(1,1-dimethylpropyl)-phenyl |
| 288. | ethyl | 4-vinylphenyl |
| 289. | ethyl | 4-isopropenylphenyl |
| 290. | ethyl | 4-(fluoromethyl)phenyl |
| 291. | ethyl | 3-(fluoromethyl)phenyl |
| 292. | ethyl | 2-(fluoromethyl)phenyl |
| 293. | ethyl | 4-(difluoromethyl)phenyl |
| 294. | ethyl | 3-(difluoromethyl)phenyl |
| 295. | ethyl | 2-(difluoromethyl)phenyl |
| 296. | ethyl | 4-(trifluoromethyl)phenyl |
| 297. | ethyl | 3-(trifluoromethyl)phenyl |
| 298. | ethyl | 2-(trifluoromethyl)phenyl |

TABLE A-continued

| No. | R¹ | Ar |
|---|---|---|
| 299. | ethyl | 4-(1-fluoroethyl)-phenyl |
| 300. | ethyl | 4-((S)-1-fluoroethyl)-phenyl |
| 301. | ethyl | 4-((R)-1-fluoroethyl)-phenyl |
| 302. | ethyl | 4-(2-fluoroethyl)-phenyl |
| 303. | ethyl | 4-(1,1-difluoroethyl)-phenyl |
| 304. | ethyl | 4-(2,2-difluoroethyl)-phenyl |
| 305. | ethyl | 4-(2,2,2-trifluoroethyl)-phenyl |
| 306. | ethyl | 4-(3-fluoropropyl)-phenyl |
| 307. | ethyl | 4-(2-fluoropropyl)-phenyl |
| 308. | ethyl | 4-((S)-2-fluoropropyl)-phenyl |
| 309. | ethyl | 4-((R)-2-fluoropropyl)-phenyl |
| 310. | ethyl | 4-(3,3-difluoropropyl)-phenyl |
| 311. | ethyl | 4-(3,3,3-trifluoropropyl)-phenyl |
| 312. | ethyl | 4-(1-fluoro-1-methylethyl)-phenyl |
| 313. | ethyl | 4-(2-fluoro-1-methylethyl)-phenyl |
| 314. | ethyl | 4-((S)-2-fluoro-1-methylethyl)-phenyl |
| 315. | ethyl | 4-((R)-2-fluoro-1-methylethyl)-phenyl |
| 316. | ethyl | 4-(2,2-difluoro-1-methylethyl)-phenyl |
| 317. | ethyl | 4-((S)-2,2-difluoro-1-methylethyl)-phenyl |
| 318. | ethyl | 4-((R)-2,2-difluoro-1-methylethyl)-phenyl |
| 319. | ethyl | 4-(2,2,2-trifluoro-1-methylethyl)-phenyl |
| 320. | ethyl | 4-((S)-2,2,2-trifluoro-1-methylethyl)-phenyl |
| 321. | ethyl | 4-((R)-2,2,2-trifluoro-1-methylethyl)-phenyl |
| 322. | ethyl | 4-(2-fluoro-1-fluoromethylethyl)-phenyl |
| 323. | ethyl | 4-(1-difluoromethyl-2,2-difluoroethyl)-phenyl |
| 324. | ethyl | 4-(1,1-dimethyl-2-fluoroethyl)-phenyl |
| 325. | ethyl | 4-ethoxyphenyl |
| 326. | ethyl | 4-propoxyphenyl |
| 327. | ethyl | 4-isopropoxyphenyl |
| 328. | ethyl | 4-butoxyphenyl |
| 329. | ethyl | 4-(fluoromethoxy)-phenyl |
| 330. | ethyl | 4-(difluoromethoxy)-phenyl |
| 331. | ethyl | 4-(2-fluoroethoxy)-phenyl |
| 332. | ethyl | 4-(2,2-difluoroethoxy)-phenyl |
| 333. | ethyl | 4-(2,2,2-trifluoroethoxy)-phenyl |
| 334. | ethyl | 4-(1,1,2,2-tetrafluoroethoxy)-phenyl |
| 335. | ethyl | 4-cyclopropylphenyl |
| 336. | ethyl | 4-cyclobutylphenyl |
| 337. | ethyl | 4-cyclopentylphenyl |
| 338. | ethyl | 4-(2,2-difluorocyclopropyl)-phenyl |
| 339. | ethyl | 3,4-difluorophenyl |
| 340. | ethyl | 2-fluoro-4-isopropylphenyl |
| 341. | ethyl | 3-fluoro-4-isopropylphenyl |
| 342. | ethyl | 4-(1-hydroxy-1-methylethyl)-phenyl |
| 343. | ethyl | 4-(2-hydroxy-2-methylpropyl)-phenyl |
| 344. | ethyl | 4-acetylphenyl |
| 345. | ethyl | 4-carboxyphenyl |
| 346. | ethyl | 4-(O-benzyl)-phenyl |
| 347. | ethyl | 4-(2-methoxyethoxy)-phenyl |
| 348. | ethyl | 4-(CH₂—N(CH₃)₂)-phenyl |
| 349. | ethyl | 4-(NH—CO—NH₂)-phenyl |
| 350. | ethyl | 4-(fluoromethylsulfanyl)-phenyl |
| 351. | ethyl | 4-(difluoromethylsulfanyl)-phenyl |
| 352. | ethyl | 4-(trifluoromethylsulfanyl)-phenyl |
| 353. | ethyl | 4-(methylsulfonyl)-phenyl |
| 354. | ethyl | 4-(N-methoxy-N-methyl-amino)-phenyl |
| 355. | ethyl | 4-(methoxyamino)-phenyl |
| 356. | ethyl | 4-(ethoxyamino)-phenyl |
| 357. | ethyl | 4-(N-methylaminooxy)-phenyl |
| 358. | ethyl | 4-(N,N-dimethylaminooxy)-phenyl |
| 359. | ethyl | 4-(azetidin-1-yl)-phenyl |
| 360. | ethyl | 4-(2-methylazetidin-1-yl)-phenyl |
| 361. | ethyl | 4-((S)-2-methylazetidin-1-yl)-phenyl |
| 362. | ethyl | 4-((R)-2-methylazetidin-1-yl)-phenyl |
| 363. | ethyl | 4-(3-fluoroazetidin-1-yl)-phenyl |
| 364. | ethyl | 4-(3-methoxyazetidin-1-yl)-phenyl |
| 365. | ethyl | 4-(3-hydroxyazetidin-1-yl)-phenyl |
| 366. | ethyl | 4-(pyrrolidin-1-yl)-phenyl |
| 367. | ethyl | 4-(pyrrolidin-2-yl)-phenyl |
| 368. | ethyl | 4-((S)-pyrrolidin-2-yl)-phenyl |
| 369. | ethyl | 4-((R)-pyrrolidin-2-yl)-phenyl |
| 370. | ethyl | 4-(pyrrolidin-3-yl)-phenyl |
| 371. | ethyl | 4-((S)-pyrrolidin-3-yl)-phenyl |
| 372. | ethyl | 4-((R)-pyrrolidin-3-yl)-phenyl |
| 373. | ethyl | 4-(2-fluoropyrrolidin-1-yl)-phenyl |
| 374. | ethyl | 4-((S)-2-fluoropyrrolidin-1-yl)-phenyl |
| 375. | ethyl | 4-((R)-2-fluoropyrrolidin-1-yl)-phenyl |
| 376. | ethyl | 4-(3-fluoropyrrolidin-1-yl)-phenyl |

TABLE A-continued

| No. | R¹ | Ar |
|---|---|---|
| 377. | ethyl | 4-((S)-3-fluoropyrrolidin-1-yl)-phenyl |
| 378. | ethyl | 4-((R)-3-fluoropyrrolidin-1-yl)-phenyl |
| 379. | ethyl | 4-(2,2-difluoropyrrolidin-1-yl)-phenyl |
| 380. | ethyl | 4-(3,3-difluoropyrrolidin-1-yl)-phenyl |
| 381. | ethyl | 4-(2-methylpyrrolidin-1-yl)-phenyl |
| 382. | ethyl | 4-((S)-2-methylpyrrolidin-1-yl)-phenyl |
| 383. | ethyl | 4-((R)-2-methylpyrrolidin-1-yl)-phenyl |
| 384. | ethyl | 4-(3-methylpyrrolidin-1-yl)-phenyl |
| 385. | ethyl | 4-((S)-3-methylpyrrolidin-1-yl)-phenyl |
| 386. | ethyl | 4-((R)-3-methylpyrrolidin-1-yl)-phenyl |
| 387. | ethyl | 4-(1-methylpyrrolidin-2-yl)-phenyl |
| 388. | ethyl | 4-((S)-1-methylpyrrolidin-2-yl)-phenyl |
| 389. | ethyl | 4-((R)-1-methylpyrrolidin-2-yl)-phenyl |
| 390. | ethyl | 4-(1-methylpyrrolidin-3-yl)-phenyl |
| 391. | ethyl | 4-((S)-1-methylpyrrolidin-3-yl)-phenyl |
| 392. | ethyl | 4-((R)-1-methylpyrrolidin-3-yl)-phenyl |
| 393. | ethyl | 4-(2,2-dimethylpyrrolidin-1-yl)-phenyl |
| 394. | ethyl | 4-(3,3-dimethylpyrrolidin-1-yl)-phenyl |
| 395. | ethyl | 4-(2-trifluoromethylpyrrolidin-1-yl)-phenyl |
| 396. | ethyl | 4-((S)-2-trifluoromethylpyrrolidin-1-yl)-phenyl |
| 397. | ethyl | 4-((R)-2-trifluoromethylpyrrolidin-1-yl)-phenyl |
| 398. | ethyl | 4-(3-trifluoromethylpyrrolidin-1-yl)-phenyl |
| 399. | ethyl | 4-((S)-3-trifluoromethylpyrrolidin-1-yl)-phenyl |
| 400. | ethyl | 4-((R)-3-trifluoromethylpyrrolidin-1-yl)-phenyl |
| 401. | ethyl | 4-(2-oxopyrrolidin-1-yl)-phenyl |
| 402. | ethyl | 4-(2-oxo-oxazolidin-3-yl)-phenyl |
| 403. | ethyl | 4-(piperidin-1-yl)-phenyl |
| 404. | ethyl | 4-(2-methylpiperidin-1-yl)-phenyl |
| 405. | ethyl | 4-((S)-2-methylpiperidin-1-yl)-phenyl |
| 406. | ethyl | 4-((R)-2-methylpiperidin-1-yl)-phenyl |
| 407. | ethyl | 4-(piperazin-1-yl)-phenyl |
| 408. | ethyl | 4-(4-methylpiperazin-1-yl)-phenyl |
| 409. | ethyl | 4-(morpholin-4-yl)-phenyl |
| 410. | ethyl | 4-(thiomorpholin-4-yl)-phenyl |
| 411. | ethyl | 4-(1-oxo-thiomorpholin-4-yl)-phenyl |
| 412. | ethyl | 4-(1,1-dioxo-thiomorpholin-4-yl)-phenyl |
| 413. | ethyl | 4-(pyrrol-1-yl)-phenyl |
| 414. | ethyl | 4-(pyrrol-2-yl)-phenyl |
| 415. | ethyl | 4-(pyrrol-3-yl)-phenyl |
| 416. | ethyl | 4-(1-methylpyrrol-2-yl)-phenyl |
| 417. | ethyl | 4-(1-methylpyrrol-3-yl)-phenyl |
| 418. | ethyl | 4-(furan-2-yl)-phenyl |
| 419. | ethyl | 4-(furan-3-yl)-phenyl |
| 420. | ethyl | 4-(thiophen-2-yl)-phenyl |
| 421. | ethyl | 4-(thiophen-3-yl)-phenyl |
| 422. | ethyl | 4-(5-propylthien-2-yl)-phenyl |
| 423. | ethyl | 4-(pyrazol-1-yl)-phenyl |
| 424. | ethyl | 4-(pyrazol-3-yl)-phenyl |
| 425. | ethyl | 4-(pyrazol-4-yl)-phenyl |
| 426. | ethyl | 4-(1-methyl-1H-pyrazol-4-yl)-phenyl |
| 427. | ethyl | 4-(1-ethyl-1H-pyrazol-4-yl)-phenyl |
| 428. | ethyl | 4-(1-methyl-1H-pyrazol-5-yl)-phenyl |
| 429. | ethyl | 4-(1H-imidazol-2-yl)-phenyl |
| 430. | ethyl | 4-(imidazol-1-yl)-phenyl |
| 431. | ethyl | 4-(1-methylimidazol-2-yl)-phenyl |
| 432. | ethyl | 4-(oxazol-2-yl)-phenyl |
| 433. | ethyl | 4-(oxazol-4-yl)-phenyl |
| 434. | ethyl | 4-(oxazol-5-yl)-phenyl |
| 435. | ethyl | 4-(isoxazol-3-yl)-phenyl |
| 436. | ethyl | 4-(isoxazol-4-yl)-phenyl |
| 437. | ethyl | 4-(isoxazol-5-yl)-phenyl |
| 438. | ethyl | 4-([1,2,3]-triazol-1-yl)-phenyl |
| 439. | ethyl | 4-([1,2,4]-triazol-1-yl)-phenyl |
| 440. | ethyl | 4-([1,2,3]-triazol-2-yl)-phenyl |
| 441. | ethyl | 4-(4H-[1,2,4]-triazol-3-yl)-phenyl |
| 442. | ethyl | 4-([1,2,4]-triazol-4-yl)-phenyl |
| 443. | ethyl | 4-(2H-[1,2,3]-triazol-4-yl)-phenyl |
| 444. | ethyl | 4-(4-methyl-4H-[1,2,4]-triazol-3-yl)-phenyl |
| 445. | ethyl | 4-(2-methyl-2H-[1,2,3]-triazol-4-yl)-phenyl |
| 446. | ethyl | 4-([1,3,4]-oxadiazol-2-yl)-phenyl |
| 447. | ethyl | 4-([1,2,4]-oxadiazol-3-yl)-phenyl |
| 448. | ethyl | 4-([1,2,4]-oxadiazol-5-yl)-phenyl |
| 449. | ethyl | 4-([1,2,3]-oxadiazol-4-yl)-phenyl |
| 450. | ethyl | 4-([1,2,3]-oxadiazol-5-yl)-phenyl |
| 451. | ethyl | 4-([1,2,3]-thiadiazol-4-yl)-phenyl |
| 452. | ethyl | 4-(1H-tetrazol-5-yl)-phenyl |
| 453. | ethyl | 4-(tetrazol-1-yl)-phenyl |
| 454. | ethyl | 4-(2-methyl-2H-tetrazol-5-yl)-phenyl |

TABLE A-continued

| No. | R¹ | Ar |
|---|---|---|
| 455. | ethyl | 4-(1-methyl-1H-tetrazol-5-yl)-phenyl |
| 456. | ethyl | 4-furazan-3-yl-phenyl |
| 457. | ethyl | 4-(pyrid-2-yl)-phenyl |
| 458. | ethyl | 4-(pyrid-3-yl)-phenyl |
| 459. | ethyl | 4-(pyrid-4-yl)-phenyl |
| 460. | ethyl | 4-(pyrimidin-2-yl)-phenyl |
| 461. | ethyl | 4-(pyrimidin-4-yl)-phenyl |
| 462. | ethyl | 4-(pyrimidin-5-yl)-phenyl |
| 463. | ethyl | 5-isopropylthiophen-2-yl |
| 464. | ethyl | 2-chlorothiophen-5-yl |
| 465. | ethyl | 2,5-dichlorothiophen-4-yl |
| 466. | ethyl | 2,3-dichlorothiophen-5-yl |
| 467. | ethyl | 2-chloro-3-nitrothiophen-5-yl |
| 468. | ethyl | 2-(phenylsulfonyl)-thiophen-5-yl |
| 469. | ethyl | 2-(pyridin-2-yl)thiophen-5-yl |
| 470. | ethyl | 2-(5-(trifluoromethyl)isoxazol-3-yl)-thiophen-5-yl |
| 471. | ethyl | 2-(2-methylthiazol-4-yl)-thiophen-5-yl |
| 472. | ethyl | 1-methyl-1H-imidazol-4-yl |
| 473. | ethyl | 1,2-dimethyl-1H-imidazol-4-yl |
| 474. | ethyl | 3,5-dimethylisoxazol-4-yl |
| 475. | ethyl | thiazol-2-yl |
| 476. | ethyl | 4-methylthiazol-2-yl |
| 477. | ethyl | 4-isopropylthiazol-2-yl |
| 478. | ethyl | 4-trifluoromethylthiazol-2-yl |
| 479. | ethyl | 5-methylthiazol-2-yl |
| 480. | ethyl | 5-isopropylthiazol-2-yl |
| 481. | ethyl | 5-trifluoromethylthiazol-2-yl |
| 482. | ethyl | 2,4-dimethylthiazol-5-yl |
| 483. | ethyl | 2-acetamido-4-methylthiazol-5-yl |
| 484. | ethyl | 4H-[1,2,4]triazol-3-yl |
| 485. | ethyl | 5-methyl-4H-[1,2,4]triazol-3-yl |
| 486. | ethyl | 4-methyl-4H-[1,2,4]triazol-3-yl |
| 487. | ethyl | 5-isopropyl-4H-[1,2,4]triazol-3-yl |
| 488. | ethyl | 5-trifluoromethyl-4H-[1,2,4]triazol-3-yl |
| 489. | ethyl | 4,5-dimethyl-4H-[1,2,4]triazol-3-yl |
| 490. | ethyl | 5-isopropyl-4-methyl-4H-[1,2,4]triazol-3-yl |
| 491. | ethyl | 5-trifluoromethyl-4-methyl-4H-[1,2,4]triazol-3-yl |
| 492. | ethyl | [1,3,4]thiadiazol-2-yl |
| 493. | ethyl | 5-methyl-[1,3,4]thiadiazol-2-yl |
| 494. | ethyl | 5-isopropyl-[1,3,4]thiadiazol-2-yl |
| 495. | ethyl | 5-trifluoromethyl-[1,3,4]thiadiazol-2-yl |
| 496. | ethyl | 3-bromo-2-chloropyrid-5-yl |
| 497. | ethyl | 2-(4-morpholino)-pyrid-5-yl |
| 498. | ethyl | 2-phenoxypyrid-5-yl |
| 499. | ethyl | (2-isopropyl)-pyrimidin-5-yl |
| 500. | ethyl | (5-isopropyl)-pyrimidin-2-yl |
| 501. | ethyl | 8-quinolyl |
| 502. | ethyl | 5-isoquinolyl |
| 503. | ethyl | 2-(trifluoroacetyl)-1,2,3,4-tetrahydroisoquinolin-7-yl |
| 504. | ethyl | 5-chloro-3-methylbenzothiophen-2-yl |
| 505. | ethyl | 3,4-dihydro-4-methyl-2H-benzo[b][1,4]oxazinyl |
| 506. | ethyl | benzothiazol-6-yl |
| 507. | ethyl | benzo[2,1,3]oxadiazol-4-yl |
| 508. | ethyl | 5-chlorobenzo[2,1,3]oxadiazol-4-yl |
| 509. | ethyl | 7-chlorobenzo[2,1,3]oxadiazol-4-yl |
| 510. | ethyl | benzo[2,1,3]thiadiazol-4-yl |
| 511. | methyl | 4-isopropylphenyl |
| 512. | methyl | 4-sec-butylphenyl |
| 513. | methyl | 4-isobutylphenyl |
| 514. | methyl | 4-(1,1-dimethylpropyl)-phenyl |
| 515. | methyl | 4-vinylphenyl |
| 516. | methyl | 4-isopropenylphenyl |
| 517. | methyl | 4-(fluoromethyl)phenyl |
| 518. | methyl | 3-(fluoromethyl)phenyl |
| 519. | methyl | 2-(fluoromethyl)phenyl |
| 520. | methyl | 4-(difluoromethyl)phenyl |
| 521. | methyl | 3-(difluoromethyl)phenyl |
| 522. | methyl | 2-(difluoromethyl)phenyl |
| 523. | methyl | 4-(1-fluoroethyl)-phenyl |
| 524. | methyl | 4-((S)-1-fluoroethyl)-phenyl |
| 525. | methyl | 4-((R)-1-fluoroethyl)-phenyl |
| 526. | methyl | 4-(2-fluoroethyl)-phenyl |
| 527. | methyl | 4-(1,1-difluoroethyl)-phenyl |
| 528. | methyl | 4-(2,2-difluoroethyl)-phenyl |
| 529. | methyl | 4-(2,2,2-trifluoroethyl)-phenyl |
| 530. | methyl | 4-(3-fluoropropyl)-phenyl |
| 531. | methyl | 4-(2-fluoropropyl)-phenyl |

TABLE A-continued

| No. | R¹ | Ar |
|---|---|---|
| 532. | methyl | 4-((S)-2-fluoropropyl)-phenyl |
| 533. | methyl | 4-((R)-2-fluoropropyl)-phenyl |
| 534. | methyl | 4-(3,3-difluoropropyl)-phenyl |
| 535. | methyl | 4-(3,3,3-trifluoropropyl)-phenyl |
| 536. | methyl | 4-(1-fluoro-1-methylethyl)-phenyl |
| 537. | methyl | 4-(2-fluoro-1-methylethyl)-phenyl |
| 538. | methyl | 4-((S)-2-fluoro-1-methylethyl)-phenyl |
| 539. | methyl | 4-((R)-2-fluoro-1-methylethyl)-phenyl |
| 540. | methyl | 4-(2,2-difluoro-1-methylethyl)-phenyl |
| 541. | methyl | 4-((S)-2,2-difluoro-1-methylethyl)-phenyl |
| 542. | methyl | 4-((R)-2,2-difluoro-1-methylethyl)-phenyl |
| 543. | methyl | 4-(2,2,2-trifluoro-1-methylethyl)-phenyl |
| 544. | methyl | 4-((S)-2,2,2-trifluoro-1-methylethyl)-phenyl |
| 545. | methyl | 4-((R)-2,2,2-trifluoro-1-methylethyl)-phenyl |
| 546. | methyl | 4-(2-fluoro-1-fluoromethylethyl)-phenyl |
| 547. | methyl | 4-(1-difluoromethyl-2,2-difluoroethyl)-phenyl |
| 548. | methyl | 4-(1,1-dimethyl-2-fluoroethyl)-phenyl |
| 549. | methyl | 4-ethoxyphenyl |
| 550. | methyl | 4-propoxyphenyl |
| 551. | methyl | 4-isopropoxyphenyl |
| 552. | methyl | 4-butoxyphenyl |
| 553. | methyl | 4-(fluoromethoxy)-phenyl |
| 554. | methyl | 4-(difluoromethoxy)-phenyl |
| 555. | methyl | 4-(2-fluoroethoxy)-phenyl |
| 556. | methyl | 4-(2,2-difluoroethoxy)-phenyl |
| 557. | methyl | 4-(2,2,2-trifluoroethoxy)-phenyl |
| 558. | methyl | 4-(1,1,2,2-tetrafluoroethoxy)-phenyl |
| 559. | methyl | 4-cyclopropylphenyl |
| 560. | methyl | 4-cyclobutylphenyl |
| 561. | methyl | 4-cyclopentylphenyl |
| 562. | methyl | 4-(2,2-difluorocyclopropyl)-phenyl |
| 563. | methyl | 3-fluoro-4-isopropylphenyl |
| 564. | methyl | 4-(1-hydroxy-1-methylethyl)-phenyl |
| 565. | methyl | 4-(2-hydroxy-2-methylpropyl)-phenyl |
| 566. | methyl | 4-acetylphenyl |
| 567. | methyl | 4-carboxyphenyl |
| 568. | methyl | 4-cyanophenyl |
| 569. | methyl | 4-hydroxyphenyl |
| 570. | methyl | 4-(O-benzyl)-phenyl |
| 571. | methyl | 4-(2-methoxyethoxy)-phenyl |
| 572. | methyl | 4-(CH$_2$—N(CH$_3$)$_2$)-phenyl |
| 573. | methyl | 4-(NH—CO—NH$_2$)-phenyl |
| 574. | methyl | 4-(methylsulfanyl)-phenyl |
| 575. | methyl | 4-(fluoromethylsulfanyl)-phenyl |
| 576. | methyl | 4-(difluoromethylsulfanyl)-phenyl |
| 577. | methyl | 4-(trifluoromethylsulfanyl)-phenyl |
| 578. | methyl | 4-(methylsulfonyl)-phenyl |
| 579. | methyl | 4-(N-methoxy-N-methyl-amino)-phenyl |
| 580. | methyl | 4-(methoxyamino)-phenyl |
| 581. | methyl | 4-(ethoxyamino)-phenyl |
| 582. | methyl | 4-(N-methylaminooxy)-phenyl |
| 583. | methyl | 4-(N,N-dimethylaminooxy)-phenyl |
| 584. | methyl | 4-(azetidin-1-yl)-phenyl |
| 585. | methyl | 4-(2-methylazetidin-1-yl)-phenyl |
| 586. | methyl | 4-((S)-2-methylazetidin-1-yl)-phenyl |
| 587. | methyl | 4-((R)-2-methylazetidin-1-yl)-phenyl |
| 588. | methyl | 4-(3-fluoroazetidin-1-yl)-phenyl |
| 589. | methyl | 4-(3-methoxyazetidin-1-yl)-phenyl |
| 590. | methyl | 4-(3-hydroxyazetidin-1-yl)-phenyl |
| 591. | methyl | 4-(pyrrolidin-1-yl)-phenyl |
| 592. | methyl | 4-(pyrrolidin-2-yl)-phenyl |
| 593. | methyl | 4-((S)-pyrrolidin-2-yl)-phenyl |
| 594. | methyl | 4-((R)-pyrrolidin-2-yl)-phenyl |
| 595. | methyl | 4-(pyrrolidin-3-yl)-phenyl |
| 596. | methyl | 4-((S)-pyrrolidin-3-yl)-phenyl |
| 597. | methyl | 4-((R)-pyrrolidin-3-yl)-phenyl |
| 598. | methyl | 4-(2-fluoropyrrolidin-1-yl)-phenyl |
| 599. | methyl | 4-((S)-2-fluoropyrrolidin-1-yl)-phenyl |
| 600. | methyl | 4-((R)-2-fluoropyrrolidin-1-yl)-phenyl |
| 601. | methyl | 4-(3-fluoropyrrolidin-1-yl)-phenyl |
| 602. | methyl | 4-((S)-3-fluoropyrrolidin-1-yl)-phenyl |
| 603. | methyl | 4-((R)-3-fluoropyrrolidin-1-yl)-phenyl |
| 604. | methyl | 4-(2,2-difluoropyrrolidin-1-yl)-phenyl |
| 605. | methyl | 4-(3,3-difluoropyrrolidin-1-yl)-phenyl |
| 606. | methyl | 4-(2-methylpyrrolidin-1-yl)-phenyl |
| 607. | methyl | 4-((S)-2-methylpyrrolidin-1-yl)-phenyl |
| 608. | methyl | 4-((R)-2-methylpyrrolidin-1-yl)-phenyl |
| 609. | methyl | 4-(3-methylpyrrolidin-1-yl)-phenyl |

TABLE A-continued

| No. | R¹ | Ar |
|---|---|---|
| 610. | methyl | 4-((S)-3-methylpyrrolidin-1-yl)-phenyl |
| 611. | methyl | 4-((R)-3-methylpyrrolidin-1-yl)-phenyl |
| 612. | methyl | 4-(1-methylpyrrolidin-2-yl)-phenyl |
| 613. | methyl | 4-((S)-1-methylpyrrolidin-2-yl)-phenyl |
| 614. | methyl | 4-((R)-1-methylpyrrolidin-2-yl)-phenyl |
| 615. | methyl | 4-(1-methylpyrrolidin-3-yl)-phenyl |
| 616. | methyl | 4-((S)-1-methylpyrrolidin-3-yl)-phenyl |
| 617. | methyl | 4-((R)-1-methylpyrrolidin-3-yl)-phenyl |
| 618. | methyl | 4-(2,2-dimethylpyrrolidin-1-yl)-phenyl |
| 619. | methyl | 4-(3,3-dimethylpyrrolidin-1-yl)-phenyl |
| 620. | methyl | 4-(2-trifluoromethylpyrrolidin-1-yl)-phenyl |
| 621. | methyl | 4-((S)-2-trifluoromethylpyrrolidin-1-yl)-phenyl |
| 622. | methyl | 4-((R)-2-trifluoromethylpyrrolidin-1-yl)-phenyl |
| 623. | methyl | 4-(3-trifluoromethylpyrrolidin-1-yl)-phenyl |
| 624. | methyl | 4-((S)-3-trifluoromethylpyrrolidin-1-yl)-phenyl |
| 625. | methyl | 4-((R)-3-trifluoromethylpyrrolidin-1-yl)-phenyl |
| 626. | methyl | 4-(2-oxopyrrolidin-1-yl)-phenyl |
| 627. | methyl | 4-(2-oxo-oxazolidin-3-yl)-phenyl |
| 628. | methyl | 4-(piperidin-1-yl)-phenyl |
| 629. | methyl | 4-(2-methylpiperidin-1-yl)-phenyl |
| 630. | methyl | 4-((S)-2-methylpiperidin-1-yl)-phenyl |
| 631. | methyl | 4-((R)-2-methylpiperidin-1-yl)-phenyl |
| 632. | methyl | 4-(piperazin-1-yl)-phenyl |
| 633. | methyl | 4-(4-methylpiperazin-1-yl)-phenyl |
| 634. | methyl | 4-(morpholin-4-yl)-phenyl |
| 635. | methyl | 4-(thiomorpholin-4-yl)-phenyl |
| 636. | methyl | 4-(1-oxo-thiomorpholin-4-yl)-phenyl |
| 637. | methyl | 4-(1,1-dioxo-thiomorpholin-4-yl)-phenyl |
| 638. | methyl | 4-(pyrrol-1-yl)-phenyl |
| 639. | methyl | 4-(pyrrol-2-yl)-phenyl |
| 640. | methyl | 4-(pyrrol-3-yl)-phenyl |
| 641. | methyl | 4-(1-methylpyrrol-2-yl)-phenyl |
| 642. | methyl | 4-(1-methylpyrrol-3-yl)-phenyl |
| 643. | methyl | 4-(furan-2-yl)-phenyl |
| 644. | methyl | 4-(furan-3-yl)-phenyl |
| 645. | methyl | 4-(thiophen-2-yl)-phenyl |
| 646. | methyl | 4-(thiophen-3-yl)-phenyl |
| 647. | methyl | 4-(5-propylthien-2-yl)-phenyl |
| 648. | methyl | 4-(pyrazol-1-yl)-phenyl |
| 649. | methyl | 4-(pyrazol-3-yl)-phenyl |
| 650. | methyl | 4-(pyrazol-4-yl)-phenyl |
| 651. | methyl | 4-(1-methyl-1H-pyrazol-4-yl)-phenyl |
| 652. | methyl | 4-(1-ethyl-1H-pyrazol-4-yl)-phenyl |
| 653. | methyl | 4-(1-methyl-1H-pyrazol-5-yl)-phenyl |
| 654. | methyl | 4-(1H-imidazol-2-yl)-phenyl |
| 655. | methyl | 4-(imidazol-1-yl)-phenyl |
| 656. | methyl | 4-(1-methylimidazol-2-yl)-phenyl |
| 657. | methyl | 4-(oxazol-2-yl)-phenyl |
| 658. | methyl | 4-(oxazol-4-yl)-phenyl |
| 659. | methyl | 4-(oxazol-5-yl)-phenyl |
| 660. | methyl | 4-(isoxazol-3-yl)-phenyl |
| 661. | methyl | 4-(isoxazol-4-yl)-phenyl |
| 662. | methyl | 4-(isoxazol-5-yl)-phenyl |
| 663. | methyl | 4-([1,2,3]-triazol-1-yl)-phenyl |
| 664. | methyl | 4-([1,2,4]-triazol-1-yl)-phenyl |
| 665. | methyl | 4-([1,2,3]-triazol-2-yl)-phenyl |
| 666. | methyl | 4-(4H-[1,2,4]-triazol-3-yl)-phenyl |
| 667. | methyl | 4-([1,2,4]-triazol-4-yl)-phenyl |
| 668. | methyl | 4-2H-[1,2,3]-triazol-4-yl)-phenyl |
| 669. | methyl | 4-(4-methyl-4H-[1,2,4]-triazol-3-yl)-phenyl |
| 670. | methyl | 4-(2-methyl-2H-[1,2,3]-triazol-4-yl)-phenyl |
| 671. | methyl | 4-([1,3,4]-oxadiazol-2-yl)-phenyl |
| 672. | methyl | 4-([1,2,4]-oxadiazol-3-yl)-phenyl |
| 673. | methyl | 4-([1,2,4]-oxadiazol-5-yl)-phenyl |
| 674. | methyl | 4-([1,2,3]-oxadiazol-4-yl)-phenyl |
| 675. | methyl | 4-([1,2,3]-oxadiazol-5-yl)-phenyl |
| 676. | methyl | 4-([1,2,3]-thiadiazol-4-yl)-phenyl |
| 677. | methyl | 4-(1H-tetrazol-5-yl)-phenyl |
| 678. | methyl | 4-(tetrazol-1-yl)-phenyl |
| 679. | methyl | 4-(2-methyl-2H-tetrazol-5-yl)-phenyl |
| 680. | methyl | 4-(1-methyl-1H-tetrazol-5-yl)-phenyl |
| 681. | methyl | 4-furazan-3-yl-phenyl |
| 682. | methyl | 4-(pyrid-2-yl)-phenyl |
| 683. | methyl | 4-(pyrid-3-yl)-phenyl |
| 684. | methyl | 4-(pyrid-4-yl)-phenyl |
| 685. | methyl | 4-(pyrimidin-2-yl)-phenyl |
| 686. | methyl | 4-(pyrimidin-4-yl)-phenyl |
| 687. | methyl | 4-(pyrimidin-5-yl)-phenyl |

TABLE A-continued

| No. | R¹ | Ar |
|---|---|---|
| 688. | methyl | 5-isopropylthiophen-2-yl |
| 689. | methyl | 2-chlorothiophen-5-yl |
| 690. | methyl | 2,5-dichlorothiophen-4-yl |
| 691. | methyl | 2,3-dichlorothiophen-5-yl |
| 692. | methyl | 2-chloro-3-nitrothiophen-5-yl |
| 693. | methyl | 2-(phenylsulfonyl)-thiophen-5-yl |
| 694. | methyl | 2-(pyridin-2-yl)thiophen-5-yl |
| 695. | methyl | 2-(5-(trifluoromethyl)isoxazol-3-yl)-thiophen-5-yl |
| 696. | methyl | 2-(2-methylthiazol-4-yl)-thiophen-5-yl |
| 697. | methyl | 1-methyl-1H-imidazol-4-yl |
| 698. | methyl | 1,2-dimethyl-1H-imidazol-4-yl |
| 699. | methyl | 3,5-dimethylisoxazol-4-yl |
| 700. | methyl | thiazol-2-yl |
| 701. | methyl | 4-methylthiazol-2-yl |
| 702. | methyl | 4-isopropylthiazol-2-yl |
| 703. | methyl | 4-trifluoromethylthiazol-2-yl |
| 704. | methyl | 5-methylthiazol-2-yl |
| 705. | methyl | 5-isopropylthiazol-2-yl |
| 706. | methyl | 5-trifluoromethylthiazol-2-yl |
| 707. | methyl | 2,4-dimethylthiazol-5-yl |
| 708. | methyl | 2-acetamido-4-methylthiazol-5-yl |
| 709. | methyl | 4H-[1,2,4]triazol-3-yl |
| 710. | methyl | 5-methyl-4H-[1,2,4]triazol-3-yl |
| 711. | methyl | 4-methyl-4H-[1,2,4]triazol-3-yl |
| 712. | methyl | 5-isopropyl-4H-[1,2,4]triazol-3-yl |
| 713. | methyl | 5-trifluoromethyl-4H-[1,2,4]triazol-3-yl |
| 714. | methyl | 4,5-dimethyl-4H-[1,2,4]triazol-3-yl |
| 715. | methyl | 5-isopropyl-4-methyl-4H-[1,2,4]triazol-3-yl |
| 716. | methyl | 5-trifluoromethyl-4-methyl-4H-[1,2,4]triazol-3-yl |
| 717. | methyl | [1,3,4]thiadiazol-2-yl |
| 718. | methyl | 5-methyl-[1,3,4]thiadiazol-2-yl |
| 719. | methyl | 5-isopropyl-[1,3,4]thiadiazol-2-yl |
| 720. | methyl | 5-trifluoromethyl-[1,3,4]thiadiazol-2-yl |
| 721. | methyl | 3-bromo-2-chloropyrid-5-yl |
| 722. | methyl | 2-(4-morpholino)-pyrid-5-yl |
| 723. | methyl | 2-phenoxypyrid-5-yl |
| 724. | methyl | (2-isopropyl)-pyrimidin-5-yl |
| 725. | methyl | (5-isopropyl)-pyrimidin-2-yl |
| 726. | methyl | 8-quinolyl |
| 727. | methyl | 5-isoquinolyl |
| 728. | methyl | 2-(trifluoroacetyl)-1,2,3,4-tetrahydroisoquinolin-7-yl |
| 729. | methyl | 5-chloro-3-methylbenzothiophen-2-yl |
| 730. | methyl | 3,4-dihydro-4-methyl-2H-benzo[b][1,4]oxazinyl |
| 731. | methyl | benzothiazol-6-yl |
| 732. | methyl | benzo[2,1,3]oxadiazol-4-yl |
| 733. | methyl | 5-chlorobenzo[2,1,3]oxadiazol-4-yl |
| 734. | methyl | 7-chlorobenzo[2,1,3]oxadiazol-4-yl |
| 735. | methyl | benzo[2,1,3]thiadiazol-4-yl |
| 736. | 3-fluoropropyl | 4-methylphenyl |
| 737. | 3-fluoropropyl | 4-ethylphenyl |
| 738. | 3-fluoropropyl | 4-propylphenyl |
| 739. | 3-fluoropropyl | 4-isopropylphenyl |
| 740. | 3-fluoropropyl | 4-sec-butylphenyl |
| 741. | 3-fluoropropyl | 4-isobutylphenyl |
| 742. | 3-fluoropropyl | 4-(1,1-dimethylpropyl)-phenyl |
| 743. | 3-fluoropropyl | 4-vinylphenyl |
| 744. | 3-fluoropropyl | 4-isopropenylphenyl |
| 745. | 3-fluoropropyl | 4-fluorophenyl |
| 746. | 3-fluoropropyl | 4-chlorophenyl |
| 747. | 3-fluoropropyl | 4-bromophenyl |
| 748. | 3-fluoropropyl | 4-(fluoromethyl)phenyl |
| 749. | 3-fluoropropyl | 3-(fluoromethyl)phenyl |
| 750. | 3-fluoropropyl | 2-(fluoromethyl)phenyl |
| 751. | 3-fluoropropyl | 4-(difluoromethyl)phenyl |
| 752. | 3-fluoropropyl | 3-(difluoromethyl)phenyl |
| 753. | 3-fluoropropyl | 2-(difluoromethyl)phenyl |
| 754. | 3-fluoropropyl | 4-(trifluoromethyl)phenyl |
| 755. | 3-fluoropropyl | 3-(trifluoromethyl)phenyl |
| 756. | 3-fluoropropyl | 2-(trifluoromethyl)phenyl |
| 757. | 3-fluoropropyl | 4-(1-fluoroethyl)-phenyl |
| 758. | 3-fluoropropyl | 4-((S)-1-fluoroethyl)-phenyl |
| 759. | 3-fluoropropyl | 4-((R)-1-fluoroethyl)-phenyl |
| 760. | 3-fluoropropyl | 4-(2-fluoroethyl)-phenyl |
| 761. | 3-fluoropropyl | 4-(1,1-difluoroethyl)-phenyl |
| 762. | 3-fluoropropyl | 4-(2,2-difluoroethyl)-phenyl |
| 763. | 3-fluoropropyl | 4-(2,2,2-trifluoroethyl)-phenyl |
| 764. | 3-fluoropropyl | 4-(3-fluoropropyl)-phenyl |

TABLE A-continued

| No. | R¹ | Ar |
|---|---|---|
| 765. | 3-fluoropropyl | 4-(2-fluoropropyl)-phenyl |
| 766. | 3-fluoropropyl | 4-((S)-2-fluoropropyl)-phenyl |
| 767. | 3-fluoropropyl | 4-((R)-2-fluoropropyl)-phenyl |
| 768. | 3-fluoropropyl | 4-(3,3-difluoropropyl)-phenyl |
| 769. | 3-fluoropropyl | 4-(3,3,3-trifluoropropyl)-phenyl |
| 770. | 3-fluoropropyl | 4-(1-fluoro-1-methylethyl)-phenyl |
| 771. | 3-fluoropropyl | 4-(2-fluoro-1-methylethyl)-phenyl |
| 772. | 3-fluoropropyl | 4-((S)-2-fluoro-1-methylethyl)-phenyl |
| 773. | 3-fluoropropyl | 4-((R)-2-fluoro-1-methylethyl)-phenyl |
| 774. | 3-fluoropropyl | 4-(2,2-difluoro-1-methylethyl)-phenyl |
| 775. | 3-fluoropropyl | 4-((S)-2,2-difluoro-1-methylethyl)-phenyl |
| 776. | 3-fluoropropyl | 4-((R)-2,2-difluoro-1-methylethyl)-phenyl |
| 777. | 3-fluoropropyl | 4-(2,2,2-trifluoro-1-methylethyl)-phenyl |
| 778. | 3-fluoropropyl | 4-((S)-2,2,2-trifluoro-1-methylethyl)-phenyl |
| 779. | 3-fluoropropyl | 4-((R)-2,2,2-trifluoro-1-methylethyl)-phenyl |
| 780. | 3-fluoropropyl | 4-(2-fluoro-1-fluoromethylethyl)-phenyl |
| 781. | 3-fluoropropyl | 4-(1-difluoromethyl-2,2-difluoroethyl)-phenyl |
| 782. | 3-fluoropropyl | 4-(1,1-dimethyl-2-fluoroethyl)-phenyl |
| 783. | 3-fluoropropyl | 4-methoxyphenyl |
| 784. | 3-fluoropropyl | 4-ethoxyphenyl |
| 785. | 3-fluoropropyl | 4-propoxyphenyl |
| 786. | 3-fluoropropyl | 4-isopropoxyphenyl |
| 787. | 3-fluoropropyl | 4-butoxyphenyl |
| 788. | 3-fluoropropyl | 4-(fluoromethoxy)-phenyl |
| 789. | 3-fluoropropyl | 4-(difluoromethoxy)-phenyl |
| 790. | 3-fluoropropyl | 4-(trifluoromethoxy)-phenyl |
| 791. | 3-fluoropropyl | 3-(trifluoromethoxy)-phenyl |
| 792. | 3-fluoropropyl | 4-(2-fluoroethoxy)-phenyl |
| 793. | 3-fluoropropyl | 4-(2,2-difluoroethoxy)-phenyl |
| 794. | 3-fluoropropyl | 4-(2,2,2-trifluoroethoxy)-phenyl |
| 795. | 3-fluoropropyl | 4-(1,1,2,2-tetrafluoroethoxy)-phenyl |
| 796. | 3-fluoropropyl | 4-cyclopropylphenyl |
| 797. | 3-fluoropropyl | 4-cyclobutylphenyl |
| 798. | 3-fluoropropyl | 4-cyclopentylphenyl |
| 799. | 3-fluoropropyl | 4-(2,2-difluorocyclopropyl)-phenyl |
| 800. | 3-fluoropropyl | 3,4-difluorophenyl |
| 801. | 3-fluoropropyl | 4-bromo-3-fluorophenyl |
| 802. | 3-fluoropropyl | 4-bromo-2-fluorophenyl |
| 803. | 3-fluoropropyl | 4-bromo-2,5-difluorophenyl |
| 804. | 3-fluoropropyl | 2-fluoro-4-isopropylphenyl |
| 805. | 3-fluoropropyl | 3-fluoro-4-isopropylphenyl |
| 806. | 3-fluoropropyl | 4-(1-hydroxy-1-methylethyl)-phenyl |
| 807. | 3-fluoropropyl | 4-(2-hydroxy-2-methylpropyl)-phenyl |
| 808. | 3-fluoropropyl | 4-acetylphenyl |
| 809. | 3-fluoropropyl | 4-carboxyphenyl |
| 810. | 3-fluoropropyl | 4-cyanophenyl |
| 811. | 3-fluoropropyl | 4-hydroxyphenyl |
| 812. | 3-fluoropropyl | 4-(O-benzyl)-phenyl |
| 813. | 3-fluoropropyl | 4-(2-methoxyethoxy)-phenyl |
| 814. | 3-fluoropropyl | 4-(CH$_2$—N(CH$_3$)$_2$)-phenyl |
| 815. | 3-fluoropropyl | 4-(NH—CO—NH$_2$)-phenyl |
| 816. | 3-fluoropropyl | 4-(methylsulfanyl)-phenyl |
| 817. | 3-fluoropropyl | 4-(fluoromethylsulfanyl)-phenyl |
| 818. | 3-fluoropropyl | 4-(difluoromethylsulfanyl)-phenyl |
| 819. | 3-fluoropropyl | 4-(trifluoromethylsulfanyl)-phenyl |
| 820. | 3-fluoropropyl | 4-(methylsulfonyl)-phenyl |
| 821. | 3-fluoropropyl | 4-(N-methoxy-N-methyl-amino)-phenyl |
| 822. | 3-fluoropropyl | 4-(methoxyamino)-phenyl |
| 823. | 3-fluoropropyl | 4-(ethoxyamino)-phenyl |
| 824. | 3-fluoropropyl | 4-(N-methylaminooxy)-phenyl |
| 825. | 3-fluoropropyl | 4-(N,N-dimethylaminooxy)-phenyl |
| 826. | 3-fluoropropyl | 4-(azetidin-1-yl)-phenyl |
| 827. | 3-fluoropropyl | 4-(2-methylazetidin-1-yl)-phenyl |
| 828. | 3-fluoropropyl | 4-((S)-2-methylazetidin-1-yl)-phenyl |
| 829. | 3-fluoropropyl | 4-((R)-2-methylazetidin-1-yl)-phenyl |
| 830. | 3-fluoropropyl | 4-(3-fluoroazetidin-1-yl)-phenyl |
| 831. | 3-fluoropropyl | 4-(3-methoxyazetidin-1-yl)-phenyl |
| 832. | 3-fluoropropyl | 4-(3-hydroxyazetidin-1-yl)-phenyl |
| 833. | 3-fluoropropyl | 4-(pyrrolidin-1-yl)-phenyl |
| 834. | 3-fluoropropyl | 4-(pyrrolidin-2-yl)-phenyl |
| 835. | 3-fluoropropyl | 4-(S)-pyrrolidin-2-yl)-phenyl |
| 836. | 3-fluoropropyl | 4-((R)-pyrrolidin-2-yl)-phenyl |
| 837. | 3-fluoropropyl | 4-(pyrrolidin-3-yl)-phenyl |
| 838. | 3-fluoropropyl | 4-((S)-pyrrolidin-3-yl)-phenyl |
| 839. | 3-fluoropropyl | 4-((R)-pyrrolidin-3-yl)-phenyl |
| 840. | 3-fluoropropyl | 4-(2-fluoropyrrolidin-1-yl)-phenyl |
| 841. | 3-fluoropropyl | 4-((S)-2-fluoropyrrolidin-1-yl)-phenyl |
| 842. | 3-fluoropropyl | 4-((R)-2-fluoropyrrolidin-1-yl)-phenyl |

TABLE A-continued

| No. | R¹ | Ar |
|---|---|---|
| 843. | 3-fluoropropyl | 4-(3-fluoropyrrolidin-1-yl)-phenyl |
| 844. | 3-fluoropropyl | 4-((S)-3-fluoropyrrolidin-1-yl)-phenyl |
| 845. | 3-fluoropropyl | 4-((R)-3-fluoropyrrolidin-1-yl)-phenyl |
| 846. | 3-fluoropropyl | 4-(2,2-difluoropyrrolidin-1-yl)-phenyl |
| 847. | 3-fluoropropyl | 4-(3,3-difluoropyrrolidin-1-yl)-phenyl |
| 848. | 3-fluoropropyl | 4-(2-methylpyrrolidin-1-yl)-phenyl |
| 849. | 3-fluoropropyl | 4-((S)-2-methylpyrrolidin-1-yl)-phenyl |
| 850. | 3-fluoropropyl | 4-((R)-2-methylpyrrolidin-1-yl)-phenyl |
| 851. | 3-fluoropropyl | 4-(3-methylpyrrolidin-1-yl)-phenyl |
| 852. | 3-fluoropropyl | 4-((S)-3-methylpyrrolidin-1-yl)-phenyl |
| 853. | 3-fluoropropyl | 4-((R)-3-methylpyrrolidin-1-yl)-phenyl |
| 854. | 3-fluoropropyl | 4-(1-methylpyrrolidin-2-yl)-phenyl |
| 855. | 3-fluoropropyl | 4-((S)-1-methylpyrrolidin-2-yl)-phenyl |
| 856. | 3-fluoropropyl | 4-((R)-1-methylpyrrolidin-2-yl)-phenyl |
| 857. | 3-fluoropropyl | 4-(1-methylpyrrolidin-3-yl)-phenyl |
| 858. | 3-fluoropropyl | 4-((S)-1-methylpyrrolidin-3-yl)-phenyl |
| 859. | 3-fluoropropyl | 4-((R)-1-methylpyrrolidin-3-yl)-phenyl |
| 860. | 3-fluoropropyl | 4-(2,2-dimethylpyrrolidin-1-yl)-phenyl |
| 861. | 3-fluoropropyl | 4-(3,3-dimethylpyrrolidin-1-yl)-phenyl |
| 862. | 3-fluoropropyl | 4-(2-trifluoromethylpyrrolidin-1-yl)-phenyl |
| 863. | 3-fluoropropyl | 4-((S)-2-trifluoromethylpyrrolidin-1-yl)-phenyl |
| 864. | 3-fluoropropyl | 4-((R)-2-trifluoromethylpyrrolidin-1-yl)-phenyl |
| 865. | 3-fluoropropyl | 4-(3-trifluoromethylpyrrolidin-1-yl)-phenyl |
| 866. | 3-fluoropropyl | 4-((S)-3-trifluoromethylpyrrolidin-1-yl)-phenyl |
| 867. | 3-fluoropropyl | 4-((R)-3-trifluoromethylpyrrolidin-1-yl)-phenyl |
| 868. | 3-fluoropropyl | 4-(2-oxopyrrolidin-1-yl)-phenyl |
| 869. | 3-fluoropropyl | 4-(2-oxo-oxazolidin-3-yl)-phenyl |
| 870. | 3-fluoropropyl | 4-(piperidin-1-yl)-phenyl |
| 871. | 3-fluoropropyl | 4-(2-methylpiperidin-1-yl)-phenyl |
| 872. | 3-fluoropropyl | 4-((S)-2-methylpiperidin-1-yl)-phenyl |
| 873. | 3-fluoropropyl | 4-((R)-2-methylpiperidin-1-yl)-phenyl |
| 874. | 3-fluoropropyl | 4-(piperazin-1-yl)-phenyl |
| 875. | 3-fluoropropyl | 4-(4-methylpiperazin-1-yl)-phenyl |
| 876. | 3-fluoropropyl | 4-(morpholin-4-yl)-phenyl |
| 877. | 3-fluoropropyl | 4-(thiomorpholin-4-yl)-phenyl |
| 878. | 3-fluoropropyl | 4-(1-oxo-thiomorpholin-4-yl)-phenyl |
| 879. | 3-fluoropropyl | 4-(1,1-dioxo-thiomorpholin-4-yl)-phenyl |
| 880. | 3-fluoropropyl | 4-(pyrrol-1-yl)-phenyl |
| 881. | 3-fluoropropyl | 4-(pyrrol-2-yl)-phenyl |
| 882. | 3-fluoropropyl | 4-(pyrrol-3-yl)-phenyl |
| 883. | 3-fluoropropyl | 4-(1-methylpyrrol-2-yl)-phenyl |
| 884. | 3-fluoropropyl | 4-(1-methylpyrrol-3-yl)-phenyl |
| 885. | 3-fluoropropyl | 4-(furan-2-yl)-phenyl |
| 886. | 3-fluoropropyl | 4-(furan-3-yl)-phenyl |
| 887. | 3-fluoropropyl | 4-(thiophen-2-yl)-phenyl |
| 888. | 3-fluoropropyl | 4-(thiophen-3-yl)-phenyl |
| 889. | 3-fluoropropyl | 4-(5-propylthien-2-yl)-phenyl |
| 890. | 3-fluoropropyl | 4-(pyrazol-1-yl)-phenyl |
| 891. | 3-fluoropropyl | 4-(pyrazol-3-yl)-phenyl |
| 892. | 3-fluoropropyl | 4-(pyrazol-4-yl)-phenyl |
| 893. | 3-fluoropropyl | 4-(1-methyl-1H-pyrazol-4-yl)-phenyl |
| 894. | 3-fluoropropyl | 4-(1-ethyl-1H-pyrazol-4-yl)-phenyl |
| 895. | 3-fluoropropyl | 4-(1-methyl-1H-pyrazol-5-yl)-phenyl |
| 896. | 3-fluoropropyl | 4-(1H-imidazol-2-yl)-phenyl |
| 897. | 3-fluoropropyl | 4-(imidazol-1-yl)-phenyl |
| 898. | 3-fluoropropyl | 4-(1-methylimidazol-2-yl)-phenyl |
| 899. | 3-fluoropropyl | 4-(oxazol-2-yl)-phenyl |
| 900. | 3-fluoropropyl | 4-(oxazol-4-yl)-phenyl |
| 901. | 3-fluoropropyl | 4-(oxazol-5-yl)-phenyl |
| 902. | 3-fluoropropyl | 4-(isoxazol-3-yl)-phenyl |
| 903. | 3-fluoropropyl | 4-(isoxazol-4-yl)-phenyl |
| 904. | 3-fluoropropyl | 4-(isoxazol-5-yl)-phenyl |
| 905. | 3-fluoropropyl | 4-([1,2,3]-triazol-1-yl)-phenyl |
| 906. | 3-fluoropropyl | 4-([1,2,4]-triazol-1-yl)-phenyl |
| 907. | 3-fluoropropyl | 4-([1,2,3]-triazol-2-yl)-phenyl |
| 908. | 3-fluoropropyl | 4-(4H-[1,2,4]-triazol-3-yl)-phenyl |
| 909. | 3-fluoropropyl | 4-([1,2,4]-triazol-4-yl)-phenyl |
| 910. | 3-fluoropropyl | 4-(2H-[1,2,3]-triazol-4-yl)-phenyl |
| 911. | 3-fluoropropyl | 4-(4-methyl-4H-[1,2,4]-triazol-3-yl)-phenyl |
| 912. | 3-fluoropropyl | 4-(2-methyl-2H-[1,2,3]-triazol-4-yl)-phenyl |
| 913. | 3-fluoropropyl | 4-([1,3,4]-oxadiazol-2-yl)-phenyl |
| 914. | 3-fluoropropyl | 4-([1,2,4]-oxadiazol-3-yl)-phenyl |
| 915. | 3-fluoropropyl | 4-([1,2,4]-oxadiazol-5-yl)-phenyl |
| 916. | 3-fluoropropyl | 4-([1,2,3]-oxadiazol-4-yl)-phenyl |
| 917. | 3-fluoropropyl | 4-([1,2,3]-oxadiazol-5-yl)-phenyl |
| 918. | 3-fluoropropyl | 4-([1,2,3]-thiadiazol-4-yl)-phenyl |
| 919. | 3-fluoropropyl | 4-(1H-tetrazol-5-yl)-phenyl |
| 920. | 3-fluoropropyl | 4-(tetrazol-1-yl)-phenyl |

TABLE A-continued

| No. | R¹ | Ar |
|---|---|---|
| 921. | 3-fluoropropyl | 4-(2-methyl-2H-tetrazol-5-yl)-phenyl |
| 922. | 3-fluoropropyl | 4-(1-methyl-1H-tetrazol-5-yl)-phenyl |
| 923. | 3-fluoropropyl | 4-furazan-3-yl-phenyl |
| 924. | 3-fluoropropyl | 4-(pyrid-2-yl)-phenyl |
| 925. | 3-fluoropropyl | 4-(pyrid-3-yl)-phenyl |
| 926. | 3-fluoropropyl | 4-(pyrid-4-yl)-phenyl |
| 927. | 3-fluoropropyl | 4-(pyrimidin-2-yl)-phenyl |
| 928. | 3-fluoropropyl | 4-(pyrimidin-4-yl)-phenyl |
| 929. | 3-fluoropropyl | 4-(pyrimidin-5-yl)-phenyl |
| 930. | 3-fluoropropyl | 5-isopropylthiophen-2-yl |
| 931. | 3-fluoropropyl | 2-chlorothiophen-5-yl |
| 932. | 3-fluoropropyl | 2,5-dichlorothiophen-4-yl |
| 933. | 3-fluoropropyl | 2,3-dichlorothiophen-5-yl |
| 934. | 3-fluoropropyl | 2-chloro-3-nitrothiophen-5-yl |
| 935. | 3-fluoropropyl | 2-(phenylsulfonyl)-thiophen-5-yl |
| 936. | 3-fluoropropyl | 2-(pyridin-2-yl)thiophen-5-yl |
| 937. | 3-fluoropropyl | 2-(5-(trifluoromethyl)isoxazol-3-yl)-thiophen-5-yl |
| 938. | 3-fluoropropyl | 2-(2-methylthiazol-4-yl)-thiophen-5-yl |
| 939. | 3-fluoropropyl | 1-methyl-1H-imidazol-4-yl |
| 940. | 3-fluoropropyl | 1,2-dimethyl-1H-imidazol-4-yl |
| 941. | 3-fluoropropyl | 3,5-dimethylisoxazol-4-yl |
| 942. | 3-fluoropropyl | thiazol-2-yl |
| 943. | 3-fluoropropyl | 4-methylthiazol-2-yl |
| 944. | 3-fluoropropyl | 4-isopropylthiazol-2-yl |
| 945. | 3-fluoropropyl | 4-trifluoromethylthiazol-2-yl |
| 946. | 3-fluoropropyl | 5-methylthiazol-2-yl |
| 947. | 3-fluoropropyl | 5-isopropylthiazol-2-yl |
| 948. | 3-fluoropropyl | 5-trifluoromethylthiazol-2-yl |
| 949. | 3-fluoropropyl | 2,4-dimethylthiazol-5-yl |
| 950. | 3-fluoropropyl | 2-acetamido-4-methylthiazol-5-yl |
| 951. | 3-fluoropropyl | 4H-[1,2,4]triazol-3-yl |
| 952. | 3-fluoropropyl | 5-methyl-4H-[1,2,4]triazol-3-yl |
| 953. | 3-fluoropropyl | 4-methyl-4H-[1,2,4]triazol-3-yl |
| 954. | 3-fluoropropyl | 5-isopropyl-4H-[1,2,4]triazol-3-yl |
| 955. | 3-fluoropropyl | 5-trifluoromethyl-4H-[1,2,4]triazol-3-yl |
| 956. | 3-fluoropropyl | 4,5-dimethyl-4H-[1,2,4]triazol-3-yl |
| 957. | 3-fluoropropyl | 5-isopropyl-4-methyl-4H-[1,2,4]triazol-3-yl |
| 958. | 3-fluoropropyl | 5-trifluoromethyl-4-methyl-4H-[1,2,4]triazol-3-yl |
| 959. | 3-fluoropropyl | [1,3,4]thiadiazol-2-yl |
| 960. | 3-fluoropropyl | 5-methyl-[1,3,4]thiadiazol-2-yl |
| 961. | 3-fluoropropyl | 5-isopropyl-[1,3,4]thiadiazol-2-yl |
| 962. | 3-fluoropropyl | 5-trifluoromethyl-[1,3,4]thiadiazol-2-yl |
| 963. | 3-fluoropropyl | 3-bromo-2-chloropyrid-5-yl |
| 964. | 3-fluoropropyl | 2-(4-morpholino)-pyrid-5-yl |
| 965. | 3-fluoropropyl | 2-phenoxypyrid-5-yl |
| 966. | 3-fluoropropyl | (2-isopropyl)-pyrimidin-5-yl |
| 967. | 3-fluoropropyl | (5-isopropyl)-pyrimidin-2-yl |
| 968. | 3-fluoropropyl | 8-quinolyl |
| 969. | 3-fluoropropyl | 5-isoquinolyl |
| 970. | 3-fluoropropyl | 2-(trifluoroacetyl)-1,2,3,4-tetrahydroisoquinolin-7-yl |
| 971. | 3-fluoropropyl | 5-chloro-3-methylbenzothiophen-2-yl |
| 972. | 3-fluoropropyl | 3,4-dihydro-4-methyl-2H-benzo[b][1,4]oxazinyl |
| 973. | 3-fluoropropyl | benzothiazol-6-yl |
| 974. | 3-fluoropropyl | benzo[2,1,3]oxadiazol-4-yl |
| 975. | 3-fluoropropyl | 5-chlorobenzo[2,1,3]oxadiazol-4-yl |
| 976. | 3-fluoropropyl | 7-chlorobenzo[2,1,3]oxadiazol-4-yl |
| 977. | 3-fluoropropyl | benzo[2,1,3]thiadiazol-4-yl |
| 978. | 2-fluoroethyl | 4-methylphenyl |
| 979. | 2-fluoroethyl | 4-ethylphenyl |
| 980. | 2-fluoroethyl | 4-propylphenyl |
| 981. | 2-fluoroethyl | 4-isopropylphenyl |
| 982. | 2-fluoroethyl | 4-sec-butylphenyl |
| 983. | 2-fluoroethyl | 4-isobutylphenyl |
| 984. | 2-fluoroethyl | 4-(1,1-dimethylpropyl)-phenyl |
| 985. | 2-fluoroethyl | 4-vinylphenyl |
| 986. | 2-fluoroethyl | 4-isopropenylphenyl |
| 987. | 2-fluoroethyl | 4-fluorophenyl |
| 988. | 2-fluoroethyl | 4-chlorophenyl |
| 989. | 2-fluoroethyl | 4-bromophenyl |
| 990. | 2-fluoroethyl | 4-(fluoromethyl)phenyl |
| 991. | 2-fluoroethyl | 3-(fluoromethyl)phenyl |
| 992. | 2-fluoroethyl | 2-(fluoromethyl)phenyl |
| 993. | 2-fluoroethyl | 4-(difluoromethyl)phenyl |
| 994. | 2-fluoroethyl | 3-(difluoromethyl)phenyl |
| 995. | 2-fluoroethyl | 2-(difluoromethyl)phenyl |
| 996. | 2-fluoroethyl | 4-(trifluoromethyl)phenyl |
| 997. | 2-fluoroethyl | 3-(trifluoromethyl)phenyl |
| 998. | 2-fluoroethyl | 2-(trifluoromethyl)phenyl |

TABLE A-continued

| No. | R¹ | Ar |
|---|---|---|
| 999. | 2-fluoroethyl | 4-(1-fluoroethyl)-phenyl |
| 1000. | 2-fluoroethyl | 4-((S)-1-fluoroethyl)-phenyl |
| 1001. | 2-fluoroethyl | 4-((R)-1-fluoroethyl)-phenyl |
| 1002. | 2-fluoroethyl | 4-(2-fluoroethyl)-phenyl |
| 1003. | 2-fluoroethyl | 4-(1,1-difluoroethyl)-phenyl |
| 1004. | 2-fluoroethyl | 4-(2,2-difluoroethyl)-phenyl |
| 1005. | 2-fluoroethyl | 4-(2,2,2-trifluoroethyl)-phenyl |
| 1006. | 2-fluoroethyl | 4-(3-fluoropropyl)-phenyl |
| 1007. | 2-fluoroethyl | 4-(2-fluoropropyl)-phenyl |
| 1008. | 2-fluoroethyl | 4-((S)-2-fluoropropyl)-phenyl |
| 1009. | 2-fluoroethyl | 4-((R)-2-fluoropropyl)-phenyl |
| 1010. | 2-fluoroethyl | 4-(3,3-difluoropropyl)-phenyl |
| 1011. | 2-fluoroethyl | 4-(3,3,3-trifluoropropyl)-phenyl |
| 1012. | 2-fluoroethyl | 4-(1-fluoro-1-methylethyl)-phenyl |
| 1013. | 2-fluoroethyl | 4-(2-fluoro-1-methylethyl)-phenyl |
| 1014. | 2-fluoroethyl | 4-((S)-2-fluoro-1-methylethyl)-phenyl |
| 1015. | 2-fluoroethyl | 4-((R)-2-fluoro-1-methylethyl)-phenyl |
| 1016. | 2-fluoroethyl | 4-(2,2-difluoro-1-methylethyl)-phenyl |
| 1017. | 2-fluoroethyl | 4-((S)-2,2-difluoro-1-methylethyl)-phenyl |
| 1018. | 2-fluoroethyl | 4-((R)-2,2-difluoro-1-methylethyl)-phenyl |
| 1019. | 2-fluoroethyl | 4-(2,2,2-trifluoro-1-methylethyl)-phenyl |
| 1020. | 2-fluoroethyl | 4-((S)-2,2,2-trifluoro-1-methylethyl)-phenyl |
| 1021. | 2-fluoroethyl | 4-((R)-2,2,2-trifluoro-1-methylethyl)-phenyl |
| 1022. | 2-fluoroethyl | 4-(2-fluoro-1-fluoromethylethyl)-phenyl |
| 1023. | 2-fluoroethyl | 4-(1-difluoromethyl-2,2-difluoroethyl)-phenyl |
| 1024. | 2-fluoroethyl | 4-(1,1-dimethyl-2-fluoroethyl)-phenyl |
| 1025. | 2-fluoroethyl | 4-methoxyphenyl |
| 1026. | 2-fluoroethyl | 4-ethoxyphenyl |
| 1027. | 2-fluoroethyl | 4-propoxyphenyl |
| 1028. | 2-fluoroethyl | 4-isopropoxyphenyl |
| 1029. | 2-fluoroethyl | 4-butoxyphenyl |
| 1030. | 2-fluoroethyl | 4-(fluoromethoxy)-phenyl |
| 1031. | 2-fluoroethyl | 4-(difluoromethoxy)-phenyl |
| 1032. | 2-fluoroethyl | 4-(trifluoromethoxy)-phenyl |
| 1033. | 2-fluoroethyl | 3-(trifluoromethoxy)-phenyl |
| 1034. | 2-fluoroethyl | 4-(2-fluoroethoxy)-phenyl |
| 1035. | 2-fluoroethyl | 4-(2,2-difluoroethoxy)-phenyl |
| 1036. | 2-fluoroethyl | 4-(2,2,2-trifluoroethoxy)-phenyl |
| 1037. | 2-fluoroethyl | 4-(1,1,2,2-tetrafluoroethoxy)-phenyl |
| 1038. | 2-fluoroethyl | 4-cyclopropylphenyl |
| 1039. | 2-fluoroethyl | 4-cyclobutylphenyl |
| 1040. | 2-fluoroethyl | 4-cyclopentylphenyl |
| 1041. | 2-fluoroethyl | 4-(2,2-difluorocyclopropyl)-phenyl |
| 1042. | 2-fluoroethyl | 3,4-difluorophenyl |
| 1043. | 2-fluoroethyl | 4-bromo-3-fluorophenyl |
| 1044. | 2-fluoroethyl | 4-bromo-2-fluorophenyl |
| 1045. | 2-fluoroethyl | 4-bromo-2,5-difluorophenyl |
| 1046. | 2-fluoroethyl | 2-fluoro-4-isopropylphenyl |
| 1047. | 2-fluoroethyl | 3-fluoro-4-isopropylphenyl |
| 1048. | 2-fluoroethyl | 4-(1-hydroxy-1-methylethyl)-phenyl |
| 1049. | 2-fluoroethyl | 4-(2-hydroxy-2-methylpropyl)-phenyl |
| 1050. | 2-fluoroethyl | 4-acetylphenyl |
| 1051. | 2-fluoroethyl | 4-carboxyphenyl |
| 1052. | 2-fluoroethyl | 4-cyanophenyl |
| 1053. | 2-fluoroethyl | 4-hydroxyphenyl |
| 1054. | 2-fluoroethyl | 4-(O-benzyl)-phenyl |
| 1055. | 2-fluoroethyl | 4-(2-methoxyethoxy)-phenyl |
| 1056. | 2-fluoroethyl | 4-(CH$_2$—N(CH$_3$)$_2$)-phenyl |
| 1057. | 2-fluoroethyl | 4-(NH—CO—NH$_2$)-phenyl |
| 1058. | 2-fluoroethyl | 4-(methylsulfanyl)-phenyl |
| 1059. | 2-fluoroethyl | 4-(fluoromethylsulfanyl)-phenyl |
| 1060. | 2-fluoroethyl | 4-(difluoromethylsulfanyl)-phenyl |
| 1061. | 2-fluoroethyl | 4-(trifluoromethylsulfanyl)-phenyl |
| 1062. | 2-fluoroethyl | 4-(methylsulfonyl)-phenyl |
| 1063. | 2-fluoroethyl | 4-(N-methoxy-N-methyl-amino)-phenyl |
| 1064. | 2-fluoroethyl | 4-(methoxyamino)-phenyl |
| 1065. | 2-fluoroethyl | 4-(ethoxyamino)-phenyl |
| 1066. | 2-fluoroethyl | 4-(N-methylaminooxy)-phenyl |
| 1067. | 2-fluoroethyl | 4-(N,N-dimethylaminooxy)-phenyl |
| 1068. | 2-fluoroethyl | 4-(azetidin-1-yl)-phenyl |
| 1069. | 2-fluoroethyl | 4-(2-methylazetidin-1-yl)-phenyl |
| 1070. | 2-fluoroethyl | 4-((S)-2-methylazetidin-1-yl)-phenyl |
| 1071. | 2-fluoroethyl | 4-((R)-2-methylazetidin-1-yl)-phenyl |
| 1072. | 2-fluoroethyl | 4-(3-fluoroazetidin-1-yl)-phenyl |
| 1073. | 2-fluoroethyl | 4-(3-methoxyazetidin-1-yl)-phenyl |
| 1074. | 2-fluoroethyl | 4-(3-hydroxyazetidin-1-yl)-phenyl |
| 1075. | 2-fluoroethyl | 4-(pyrrolidin-1-yl)-phenyl |
| 1076. | 2-fluoroethyl | 4-(pyrrolidin-2-yl)-phenyl |

TABLE A-continued

| No. | R¹ | Ar |
|---|---|---|
| 1077. | 2-fluoroethyl | 4-((S)-pyrrolidin-2-yl)-phenyl |
| 1078. | 2-fluoroethyl | 4-((R)-pyrrolidin-2-yl)-phenyl |
| 1079. | 2-fluoroethyl | 4-(pyrrolidin-3-yl)-phenyl |
| 1080. | 2-fluoroethyl | 4-((S)-pyrrolidin-3-yl)-phenyl |
| 1081. | 2-fluoroethyl | 4-((R)-pyrrolidin-3-yl)-phenyl |
| 1082. | 2-fluoroethyl | 4-(2-fluoropyrrolidin-1-yl)-phenyl |
| 1083. | 2-fluoroethyl | 4-((S)-2-fluoropyrrolidin-1-yl)-phenyl |
| 1084. | 2-fluoroethyl | 4-((R)-2-fluoropyrrolidin-1-yl)-phenyl |
| 1085. | 2-fluoroethyl | 4-(3-fluoropyrrolidin-1-yl)-phenyl |
| 1086. | 2-fluoroethyl | 4-((S)-3-fluoropyrrolidin-1-yl)-phenyl |
| 1087. | 2-fluoroethyl | 4-((R)-3-fluoropyrrolidin-1-yl)-phenyl |
| 1088. | 2-fluoroethyl | 4-(2,2-difluoropyrrolidin-1-yl)-phenyl |
| 1089. | 2-fluoroethyl | 4-(3,3-difluoropyrrolidin-1-yl)-phenyl |
| 1090. | 2-fluoroethyl | 4-(2-methylpyrrolidin-1-yl)-phenyl |
| 1091. | 2-fluoroethyl | 4-((S)-2-methylpyrrolidin-1-yl)-phenyl |
| 1092. | 2-fluoroethyl | 4-((R)-2-methylpyrrolidin-1-yl)-phenyl |
| 1093. | 2-fluoroethyl | 4-(3-methylpyrrolidin-1-yl)-phenyl |
| 1094. | 2-fluoroethyl | 4-((S)-3-methylpyrrolidin-1-yl)-phenyl |
| 1095. | 2-fluoroethyl | 4-((R)-3-methylpyrrolidin-1-yl)-phenyl |
| 1096. | 2-fluoroethyl | 4-(1-methylpyrrolidin-2-yl)-phenyl |
| 1097. | 2-fluoroethyl | 4-((S)-1-methylpyrrolidin-2-yl)-phenyl |
| 1098. | 2-fluoroethyl | 4-((R)-1-methylpyrrolidin-2-yl)-phenyl |
| 1099. | 2-fluoroethyl | 4-(1-methylpyrrolidin-3-yl)-phenyl |
| 1100. | 2-fluoroethyl | 4-((S)-1-methylpyrrolidin-3-yl)-phenyl |
| 1101. | 2-fluoroethyl | 4-((R)-1-methylpyrrolidin-3-yl)-phenyl |
| 1102. | 2-fluoroethyl | 4-(2,2-dimethylpyrrolidin-1-yl)-phenyl |
| 1103. | 2-fluoroethyl | 4-(3,3-dimethylpyrrolidin-1-yl)-phenyl |
| 1104. | 2-fluoroethyl | 4-(2-trifluoromethylpyrrolidin-1-yl)-phenyl |
| 1105. | 2-fluoroethyl | 4-((S)-2-trifluoromethylpyrrolidin-1-yl)-phenyl |
| 1106. | 2-fluoroethyl | 4-((R)-2-trifluoromethylpyrrolidin-1-yl)-phenyl |
| 1107. | 2-fluoroethyl | 4-(3-trifluoromethylpyrrolidin-1-yl)-phenyl |
| 1108. | 2-fluoroethyl | 4-((S)-3-trifluoromethylpyrrolidin-1-yl)-phenyl |
| 1109. | 2-fluoroethyl | 4-((R)-3-trifluoromethylpyrrolidin-1-yl)-phenyl |
| 1110. | 2-fluoroethyl | 4-(2-oxopyrrolidin-1-yl)-phenyl |
| 1111. | 2-fluoroethyl | 4-(2-oxo-oxazolidin-3-yl)-phenyl |
| 1112. | 2-fluoroethyl | 4-(piperidin-1-yl)-phenyl |
| 1113. | 2-fluoroethyl | 4-(2-methylpiperidin-1-yl)-phenyl |
| 1114. | 2-fluoroethyl | 4-((S)-2-methylpiperidin-1-yl)-phenyl |
| 1115. | 2-fluoroethyl | 4-((R)-2-methylpiperidin-1-yl)-phenyl |
| 1116. | 2-fluoroethyl | 4-(piperazin-1-yl)-phenyl |
| 1117. | 2-fluoroethyl | 4-(4-methylpiperazin-1-yl)-phenyl |
| 1118. | 2-fluoroethyl | 4-(morpholin-4-yl)-phenyl |
| 1119. | 2-fluoroethyl | 4-(thiomorpholin-4-yl)-phenyl |
| 1120. | 2-fluoroethyl | 4-(1-oxo-thiomorpholin-4-yl)-phenyl |
| 1121. | 2-fluoroethyl | 4-(1,1-dioxo-thiomorpholin-4-yl)-phenyl |
| 1122. | 2-fluoroethyl | 4-(pyrrol-1-yl)-phenyl |
| 1123. | 2-fluoroethyl | 4-(pyrrol-2-yl)-phenyl |
| 1124. | 2-fluoroethyl | 4-(pyrrol-3-yl)-phenyl |
| 1125. | 2-fluoroethyl | 4-(1-methylpyrrol-2-yl)-phenyl |
| 1126. | 2-fluoroethyl | 4-(1-methylpyrrol-3-yl)-phenyl |
| 1127. | 2-fluoroethyl | 4-(furan-2-yl)-phenyl |
| 1128. | 2-fluoroethyl | 4-(furan-3-yl)-phenyl |
| 1129. | 2-fluoroethyl | 4-(thiophen-2-yl)-phenyl |
| 1130. | 2-fluoroethyl | 4-(thiophen-3-yl)-phenyl |
| 1131. | 2-fluoroethyl | 4-(5-propylthien-2-yl)-phenyl |
| 1132. | 2-fluoroethyl | 4-(pyrazol-1-yl)-phenyl |
| 1133. | 2-fluoroethyl | 4-(pyrazol-3-yl)-phenyl |
| 1134. | 2-fluoroethyl | 4-(pyrazol-4-yl)-phenyl |
| 1135. | 2-fluoroethyl | 4-(1-methyl-1H-pyrazol-4-yl)-phenyl |
| 1136. | 2-fluoroethyl | 4-(1-ethyl-1H-pyrazol-4-yl)-phenyl |
| 1137. | 2-fluoroethyl | 4-(1-methyl-1H-pyrazol-5-yl)-phenyl |
| 1138. | 2-fluoroethyl | 4-(1H-imidazol-2-yl)-phenyl |
| 1139. | 2-fluoroethyl | 4-(imidazol-1-yl)-phenyl |
| 1140. | 2-fluoroethyl | 4-(1-methylimidazol-2-yl)-phenyl |
| 1141. | 2-fluoroethyl | 4-(oxazol-2-yl)-phenyl |
| 1142. | 2-fluoroethyl | 4-(oxazol-4-yl)-phenyl |
| 1143. | 2-fluoroethyl | 4-(oxazol-5-yl)-phenyl |
| 1144. | 2-fluoroethyl | 4-(isoxazol-3-yl)-phenyl |
| 1145. | 2-fluoroethyl | 4-(isoxazol-4-yl)-phenyl |
| 1146. | 2-fluoroethyl | 4-(isoxazol-5-yl)-phenyl |
| 1147. | 2-fluoroethyl | 4-([1,2,3]-triazol-1-yl)-phenyl |
| 1148. | 2-fluoroethyl | 4-([1,2,4]-triazol-1-yl)-phenyl |
| 1149. | 2-fluoroethyl | 4-([1,2,3]-triazol-2-yl)-phenyl |
| 1150. | 2-fluoroethyl | 4-(4H-[1,2,4]-triazol-3-yl)-phenyl |
| 1151. | 2-fluoroethyl | 4-([1,2,4]-triazol-4-yl)-phenyl |
| 1152. | 2-fluoroethyl | 4-(2H-[1,2,3]-triazol-4-yl)-phenyl |
| 1153. | 2-fluoroethyl | 4-(4-methyl-4H-[1,2,4]-triazol-3-yl)-phenyl |
| 1154. | 2-fluoroethyl | 4-(2-methyl-2H-[1,2,3]-triazol-4-yl)-phenyl |

TABLE A-continued

| No. | R¹ | Ar |
|---|---|---|
| 1155. | 2-fluoroethyl | 4-([1,3,4]-oxadiazol-2-yl)-phenyl |
| 1156. | 2-fluoroethyl | 4-([1,2,4]-oxadiazol-3-yl)-phenyl |
| 1157. | 2-fluoroethyl | 4-([1,2,4]-oxadiazol-5-yl)-phenyl |
| 1158. | 2-fluoroethyl | 4-([1,2,3]-oxadiazol-4-yl)-phenyl |
| 1159. | 2-fluoroethyl | 4-([1,2,3]-oxadiazol-5-yl)-phenyl |
| 1160. | 2-fluoroethyl | 4-([1,2,3]-thiadiazol-4-yl)-phenyl |
| 1161. | 2-fluoroethyl | 4-(1H-tetrazol-5-yl)-phenyl |
| 1162. | 2-fluoroethyl | 4-(tetrazol-1-yl)-phenyl |
| 1163. | 2-fluoroethyl | 4-(2-methyl-2H-tetrazol-5-yl)-phenyl |
| 1164. | 2-fluoroethyl | 4-(1-methyl-1H-tetrazol-5-yl)-phenyl |
| 1165. | 2-fluoroethyl | 4-furazan-3-yl-phenyl |
| 1166. | 2-fluoroethyl | 4-(pyrid-2-yl)-phenyl |
| 1167. | 2-fluoroethyl | 4-(pyrid-3-yl)-phenyl |
| 1168. | 2-fluoroethyl | 4-(pyrid-4-yl)-phenyl |
| 1169. | 2-fluoroethyl | 4-(pyrimidin-2-yl)-phenyl |
| 1170. | 2-fluoroethyl | 4-(pyrimidin-4-yl)-phenyl |
| 1171. | 2-fluoroethyl | 4-(pyrimidin-5-yl)-phenyl |
| 1172. | 2-fluoroethyl | 5-isopropylthiophen-2-yl |
| 1173. | 2-fluoroethyl | 2-chlorothiophen-5-yl |
| 1174. | 2-fluoroethyl | 2,5-dichlorothiophen-4-yl |
| 1175. | 2-fluoroethyl | 2,3-dichlorothiophen-5-yl |
| 1176. | 2-fluoroethyl | 2-chloro-3-nitrothiophen-5-yl |
| 1177. | 2-fluoroethyl | 2-(phenylsulfonyl)-thiophen-5-yl |
| 1178. | 2-fluoroethyl | 2-(pyridin-2-yl)thiophen-5-yl |
| 1179. | 2-fluoroethyl | 2-(5-(trifluoromethyl)isoxazol-3-yl)-thiophen-5-yl |
| 1180. | 2-fluoroethyl | 2-(2-methylthiazol-4-yl)-thiophen-5-yl |
| 1181. | 2-fluoroethyl | 1-methyl-1H-imidazol-4-yl |
| 1182. | 2-fluoroethyl | 1,2-dimethyl-1H-imidazol-4-yl |
| 1183. | 2-fluoroethyl | 3,5-dimethylisoxazol-4-yl |
| 1184. | 2-fluoroethyl | thiazol-2-yl |
| 1185. | 2-fluoroethyl | 4-methylthiazol-2-yl |
| 1186. | 2-fluoroethyl | 4-isopropylthiazol-2-yl |
| 1187. | 2-fluoroethyl | 4-trifluoromethylthiazol-2-yl |
| 1188. | 2-fluoroethyl | 5-methylthiazol-2-yl |
| 1189. | 2-fluoroethyl | 5-isopropylthiazol-2-yl |
| 1190. | 2-fluoroethyl | 5-trifluoromethylthiazol-2-yl |
| 1191. | 2-fluoroethyl | 2,4-dimethylthiazol-5-yl |
| 1192. | 2-fluoroethyl | 2-acetamido-4-methylthiazol-5-yl |
| 1193. | 2-fluoroethyl | 4H-[1,2,4]triazol-3-yl |
| 1194. | 2-fluoroethyl | 5-methyl-4H-[1,2,4]triazol-3-yl |
| 1195. | 2-fluoroethyl | 4-methyl-4H-[1,2,4]triazol-3-yl |
| 1196. | 2-fluoroethyl | 5-isopropyl-4H-[1,2,4]triazol-3-yl |
| 1197. | 2-fluoroethyl | 5-trifluoromethyl-4H-[1,2,4]triazol-3-yl |
| 1198. | 2-fluoroethyl | 4,5-dimethyl-4H-[1,2,4]triazol-3-yl |
| 1199. | 2-fluoroethyl | 5-isopropyl-4-methyl-4H-[1,2,4]triazol-3-yl |
| 1200. | 2-fluoroethyl | 5-trifluoromethyl-4-methyl-4H-[1,2,4]triazol-3-yl |
| 1201. | 2-fluoroethyl | [1,3,4]thiadiazol-2-yl |
| 1202. | 2-fluoroethyl | 5-methyl-[1,3,4]thiadiazol-2-yl |
| 1203. | 2-fluoroethyl | 5-isopropyl-[1,3,4]thiadiazol-2-yl |
| 1204. | 2-fluoroethyl | 5-trifluoromethyl-[1,3,4]thiadiazol-2-yl |
| 1205. | 2-fluoroethyl | 3-bromo-2-chloropyrid-5-yl |
| 1206. | 2-fluoroethyl | 2-(4-morpholino)-pyrid-5-yl |
| 1207. | 2-fluoroethyl | 2-phenoxypyrid-5-yl |
| 1208. | 2-fluoroethyl | (2-isopropyl)-pyrimidin-5-yl |
| 1209. | 2-fluoroethyl | (5-isopropyl)-pyrimidin-2-yl |
| 1210. | 2-fluoroethyl | 8-quinolyl |
| 1211. | 2-fluoroethyl | 5-isoquinolyl |
| 1212. | 2-fluoroethyl | 2-(trifluoroacetyl)-1,2,3,4-tetrahydroisoquinolin-7-yl |
| 1213. | 2-fluoroethyl | 5-chloro-3-methylbenzothiophen-2-yl |
| 1214. | 2-fluoroethyl | 3,4-dihydro-4-methyl-2H-benzo[b][1,4]oxazinyl |
| 1215. | 2-fluoroethyl | benzothiazol-6-yl |
| 1216. | 2-fluoroethyl | benzo[2,1,3]oxadiazol-4-yl |
| 1217. | 2-fluoroethyl | 5-chlorobenzo[2,1,3]oxadiazol-4-yl |
| 1218. | 2-fluoroethyl | 7-chlorobenzo[2,1,3]oxadiazol-4-yl |
| 1219. | 2-fluoroethyl | benzo[2,1,3]thiadiazol-4-yl |
| 1220. | cyclopropylmethyl | 4-methylphenyl |
| 1221. | cyclopropylmethyl | 4-ethylphenyl |
| 1222. | cyclopropylmethyl | 4-propylphenyl |
| 1223. | cyclopropylmethyl | 4-isopropylphenyl |
| 1224. | cyclopropylmethyl | 4-sec-butylphenyl |
| 1225. | cyclopropylmethyl | 4-isobutylphenyl |
| 1226. | cyclopropylmethyl | 4-(1,1-dimethylpropyl)-phenyl |
| 1227. | cyclopropylmethyl | 4-vinylphenyl |
| 1228. | cyclopropylmethyl | 4-isopropenylphenyl |
| 1229. | cyclopropylmethyl | 4-fluorophenyl |
| 1230. | cyclopropylmethyl | 4-chlorophenyl |
| 1231. | cyclopropylmethyl | 4-bromophenyl |
| 1232. | cyclopropylmethyl | 4-(fluoromethyl)phenyl |

TABLE A-continued

| No. | R¹ | Ar |
|---|---|---|
| 1233. | cyclopropylmethyl | 3-(fluoromethyl)phenyl |
| 1234. | cyclopropylmethyl | 2-(fluoromethyl)phenyl |
| 1235. | cyclopropylmethyl | 4-(difluoromethyl)phenyl |
| 1236. | cyclopropylmethyl | 3-(difluoromethyl)phenyl |
| 1237. | cyclopropylmethyl | 2-(difluoromethyl)phenyl |
| 1238. | cyclopropylmethyl | 4-(trifluoromethyl)phenyl |
| 1239. | cyclopropylmethyl | 3-(trifluoromethyl)phenyl |
| 1240. | cyclopropylmethyl | 2-(trifluoromethyl)phenyl |
| 1241. | cyclopropylmethyl | 4-(1-fluoroethyl)-phenyl |
| 1242. | cyclopropylmethyl | 4-((S)-1-fluoroethyl)-phenyl |
| 1243. | cyclopropylmethyl | 4-((R)-1-fluoroethyl)-phenyl |
| 1244. | cyclopropylmethyl | 4-(2-fluoroethyl)-phenyl |
| 1245. | cyclopropylmethyl | 4-(1,1-difluoroethyl)-phenyl |
| 1246. | cyclopropylmethyl | 4-(2,2-difluoroethyl)-phenyl |
| 1247. | cyclopropylmethyl | 4-(2,2,2-trifluoroethyl)-phenyl |
| 1248. | cyclopropylmethyl | 4-(3-fluoropropyl)-phenyl |
| 1249. | cyclopropylmethyl | 4-(2-fluoropropyl)-phenyl |
| 1250. | cyclopropylmethyl | 4-((S)-2-fluoropropyl)-phenyl |
| 1251. | cyclopropylmethyl | 4-((R)-2-fluoropropyl)-phenyl |
| 1252. | cyclopropylmethyl | 4-(3,3-difluoropropyl)-phenyl |
| 1253. | cyclopropylmethyl | 4-(3,3,3-trifluoropropyl)-phenyl |
| 1254. | cyclopropylmethyl | 4-(1-fluoro-1-methylethyl)-phenyl |
| 1255. | cyclopropylmethyl | 4-(2-fluoro-1-methylethyl)-phenyl |
| 1256. | cyclopropylmethyl | 4-((S)-2-fluoro-1-methylethyl)-phenyl |
| 1257. | cyclopropylmethyl | 4-((R)-2-fluoro-1-methylethyl)-phenyl |
| 1258. | cyclopropylmethyl | 4-(2,2-difluoro-1-methylethyl)-phenyl |
| 1259. | cyclopropylmethyl | 4-((S)-2,2-difluoro-1-methylethyl)-phenyl |
| 1260. | cyclopropylmethyl | 4-((R)-2,2-difluoro-1-methylethyl)-phenyl |
| 1261. | cyclopropylmethyl | 4-(2,2,2-trifluoro-1-methylethyl)-phenyl |
| 1262. | cyclopropylmethyl | 4-((S)-2,2,2-trifluoro-1-methylethyl)-phenyl |
| 1263. | cyclopropylmethyl | 4-((R)-2,2,2-trifluoro-1-methylethyl)-phenyl |
| 1264. | cyclopropylmethyl | 4-(2-fluoro-1-fluoromethylethyl)-phenyl |
| 1265. | cyclopropylmethyl | 4-(1-difluoromethyl-2,2-difluoroethyl)-phenyl |
| 1266. | cyclopropylmethyl | 4-(1,1-dimethyl-2-fluoroethyl)-phenyl |
| 1267. | cyclopropylmethyl | 4-methoxyphenyl |
| 1268. | cyclopropylmethyl | 4-ethoxyphenyl |
| 1269. | cyclopropylmethyl | 4-propoxyphenyl |
| 1270. | cyclopropylmethyl | 4-isopropoxyphenyl |
| 1271. | cyclopropylmethyl | 4-butoxyphenyl |
| 1272. | cyclopropylmethyl | 4-(fluoromethoxy)-phenyl |
| 1273. | cyclopropylmethyl | 4-(difluoromethoxy)-phenyl |
| 1274. | cyclopropylmethyl | 4-(trifluoromethoxy)-phenyl |
| 1275. | cyclopropylmethyl | 3-(trifluoromethoxy)-phenyl |
| 1276. | cyclopropylmethyl | 4-(2-fluoroethoxy)-phenyl |
| 1277. | cyclopropylmethyl | 4-(2,2-difluoroethoxy)-phenyl |
| 1278. | cyclopropylmethyl | 4-(2,2,2-trifluoroethoxy)-phenyl |
| 1279. | cyclopropylmethyl | 4-(1,1,2,2-tetrafluoroethoxy)-phenyl |
| 1280. | cyclopropylmethyl | 4-cyclopropylphenyl |
| 1281. | cyclopropylmethyl | 4-cyclobutylphenyl |
| 1282. | cyclopropylmethyl | 4-cyclopentylphenyl |
| 1283. | cyclopropylmethyl | 4-(2,2-difluorocyclopropyl)-phenyl |
| 1284. | cyclopropylmethyl | 3,4-difluorophenyl |
| 1285. | cyclopropylmethyl | 4-bromo-3-fluorophenyl |
| 1286. | cyclopropylmethyl | 4-bromo-2-fluorophenyl |
| 1287. | cyclopropylmethyl | 4-bromo-2,5-difluorophenyl |
| 1288. | cyclopropylmethyl | 2-fluoro-4-isopropylphenyl |
| 1289. | cyclopropylmethyl | 3-fluoro-4-isopropylphenyl |
| 1290. | cyclopropylmethyl | 4-(1-hydroxy-1-methylethyl)-phenyl |
| 1291. | cyclopropylmethyl | 4-(2-hydroxy-2-methylpropyl)-phenyl |
| 1292. | cyclopropylmethyl | 4-acetylphenyl |
| 1293. | cyclopropylmethyl | 4-carboxyphenyl |
| 1294. | cyclopropylmethyl | 4-cyanophenyl |
| 1295. | cyclopropylmethyl | 4-hydroxyphenyl |
| 1296. | cyclopropylmethyl | 4-(O-benzyl)-phenyl |
| 1297. | cyclopropylmethyl | 4-(2-methoxyethoxy)-phenyl |
| 1298. | cyclopropylmethyl | 4-(CH$_2$—N(CH$_3$)$_2$)-phenyl |
| 1299. | cyclopropylmethyl | 4-(NH—CO—NH$_2$)-phenyl |
| 1300. | cyclopropylmethyl | 4-(methylsulfanyl)-phenyl |
| 1301. | cyclopropylmethyl | 4-(fluoromethylsulfanyl)-phenyl |
| 1302. | cyclopropylmethyl | 4-(difluoromethylsulfanyl)-phenyl |
| 1303. | cyclopropylmethyl | 4-(trifluoromethylsulfanyl)-phenyl |
| 1304. | cyclopropylmethyl | 4-(methylsulfonyl)-phenyl |
| 1305. | cyclopropylmethyl | 4-(N-methoxy-N-methyl-amino)-phenyl |
| 1306. | cyclopropylmethyl | 4-(methoxyamino)-phenyl |
| 1307. | cyclopropylmethyl | 4-(ethoxyamino)-phenyl |
| 1308. | cyclopropylmethyl | 4-(N-methylaminooxy)-phenyl |
| 1309. | cyclopropylmethyl | 4-(N,N-dimethylaminooxy)-phenyl |
| 1310. | cyclopropylmethyl | 4-(azetidin-1-yl)-phenyl |

TABLE A-continued

| No. | R¹ | Ar |
|---|---|---|
| 1311. | cyclopropylmethyl | 4-(2-methylazetidin-1-yl)-phenyl |
| 1312. | cyclopropylmethyl | 4-((S)-2-methylazetidin-1-yl)-phenyl |
| 1313. | cyclopropylmethyl | 4-((R)-2-methylazetidin-1-yl)-phenyl |
| 1314. | cyclopropylmethyl | 4-(3-fluoroazetidin-1-yl)-phenyl |
| 1315. | cyclopropylmethyl | 4-(3-methoxyazetidin-1-yl)-phenyl |
| 1316. | cyclopropylmethyl | 4-(3-hydroxyazetidin-1-yl)-phenyl |
| 1317. | cyclopropylmethyl | 4-(pyrrolidin-1-yl)-phenyl |
| 1318. | cyclopropylmethyl | 4-(pyrrolidin-2-yl)-phenyl |
| 1319. | cyclopropylmethyl | 4-((S)-pyrrolidin-2-yl)-phenyl |
| 1320. | cyclopropylmethyl | 4-((R)-pyrrolidin-2-yl)-phenyl |
| 1321. | cyclopropylmethyl | 4-(pyrrolidin-3-yl)-phenyl |
| 1322. | cyclopropylmethyl | 4-((S)-pyrrolidin-3-yl)-phenyl |
| 1323. | cyclopropylmethyl | 4-((R)-pyrrolidin-3-yl)-phenyl |
| 1324. | cyclopropylmethyl | 4-(2-fluoropyrrolidin-1-yl)-phenyl |
| 1325. | cyclopropylmethyl | 4-((S)-2-fluoropyrrolidin-1-yl)-phenyl |
| 1326. | cyclopropylmethyl | 4-((R)-2-fluoropyrrolidin-1-yl)-phenyl |
| 1327. | cyclopropylmethyl | 4-(3-fluoropyrrolidin-1-yl)-phenyl |
| 1328. | cyclopropylmethyl | 4-((S)-3-fluoropyrrolidin-1-yl)-phenyl |
| 1329. | cyclopropylmethyl | 4-((R)-3-fluoropyrrolidin-1-yl)-phenyl |
| 1330. | cyclopropylmethyl | 4-(2,2-difluoropyrrolidin-1-yl)-phenyl |
| 1331. | cyclopropylmethyl | 4-(3,3-difluoropyrrolidin-1-yl)-phenyl |
| 1332. | cyclopropylmethyl | 4-(2-methylpyrrolidin-1-yl)-phenyl |
| 1333. | cyclopropylmethyl | 4-((S)-2-methylpyrrolidin-1-yl)-phenyl |
| 1334. | cyclopropylmethyl | 4-((R)-2-methylpyrrolidin-1-yl)-phenyl |
| 1335. | cyclopropylmethyl | 4-(3-methylpyrrolidin-1-yl)-phenyl |
| 1336. | cyclopropylmethyl | 4-((S)-3-methylpyrrolidin-1-yl)-phenyl |
| 1337. | cyclopropylmethyl | 4-((R)-3-methylpyrrolidin-1-yl)-phenyl |
| 1338. | cyclopropylmethyl | 4-(1-methylpyrrolidin-2-yl)-phenyl |
| 1339. | cyclopropylmethyl | 4-((S)-1-methylpyrrolidin-2-yl)-phenyl |
| 1340. | cyclopropylmethyl | 4-((R)-1-methylpyrrolidin-2-yl)-phenyl |
| 1341. | cyclopropylmethyl | 4-(1-methylpyrrolidin-3-yl)-phenyl |
| 1342. | cyclopropylmethyl | 4-((S)-1-methylpyrrolidin-3-yl)-phenyl |
| 1343. | cyclopropylmethyl | 4-((R)-1-methylpyrrolidin-3-yl)-phenyl |
| 1344. | cyclopropylmethyl | 4-(2,2-dimethylpyrrolidin-1-yl)-phenyl |
| 1345. | cyclopropylmethyl | 4-(3,3-dimethylpyrrolidin-1-yl)-phenyl |
| 1346. | cyclopropylmethyl | 4-(2-trifluoromethylpyrrolidin-1-yl)-phenyl |
| 1347. | cyclopropylmethyl | 4-((S)-2-trifluoromethylpyrrolidin-1-yl)-phenyl |
| 1348. | cyclopropylmethyl | 4-((R)-2-trifluoromethylpyrrolidin-1-yl)-phenyl |
| 1349. | cyclopropylmethyl | 4-(3-trifluoromethylpyrrolidin-1-yl)-phenyl |
| 1350. | cyclopropylmethyl | 4-((S)-3-trifluoromethylpyrrolidin-1-yl)-phenyl |
| 1351. | cyclopropylmethyl | 4-((R)-3-trifluoromethylpyrrolidin-1-yl)-phenyl |
| 1352. | cyclopropylmethyl | 4-(2-oxopyrrolidin-1-yl)-phenyl |
| 1353. | cyclopropylmethyl | 4-(2-oxo-oxazolidin-3-yl)-phenyl |
| 1354. | cyclopropylmethyl | 4-(piperidin-1-yl)-phenyl |
| 1355. | cyclopropylmethyl | 4-(2-methylpiperidin-1-yl)-phenyl |
| 1356. | cyclopropylmethyl | 4-((S)-2-methylpiperidin-1-yl)-phenyl |
| 1357. | cyclopropylmethyl | 4-((R)-2-methylpiperidin-1-yl)-phenyl |
| 1358. | cyclopropylmethyl | 4-(piperazin-1-yl)-phenyl |
| 1359. | cyclopropylmethyl | 4-(4-methylpiperazin-1-yl)-phenyl |
| 1360. | cyclopropylmethyl | 4-(morpholin-4-yl)-phenyl |
| 1361. | cyclopropylmethyl | 4-(thiomorpholin-4-yl)-phenyl |
| 1362. | cyclopropylmethyl | 4-(1-oxo-thiomorpholin-4-yl)-phenyl |
| 1363. | cyclopropylmethyl | 4-(1,1-dioxo-thiomorpholin-4-yl)-phenyl |
| 1364. | cyclopropylmethyl | 4-(pyrrol-1-yl)-phenyl |
| 1365. | cyclopropylmethyl | 4-(pyrrol-2-yl)-phenyl |
| 1366. | cyclopropylmethyl | 4-(pyrrol-3-yl)-phenyl |
| 1367. | cyclopropylmethyl | 4-(1-methylpyrrol-2-yl)-phenyl |
| 1368. | cyclopropylmethyl | 4-(1-methylpyrrol-3-yl)-phenyl |
| 1369. | cyclopropylmethyl | 4-(furan-2-yl)-phenyl |
| 1370. | cyclopropylmethyl | 4-(furan-3-yl)-phenyl |
| 1371. | cyclopropylmethyl | 4-(thiophen-2-yl)-phenyl |
| 1372. | cyclopropylmethyl | 4-(thiophen-3-yl)-phenyl |
| 1373. | cyclopropylmethyl | 4-(5-propylthien-2-yl)-phenyl |
| 1374. | cyclopropylmethyl | 4-(pyrazol-1-yl)-phenyl |
| 1375. | cyclopropylmethyl | 4-(pyrazol-3-yl)-phenyl |
| 1376. | cyclopropylmethyl | 4-(pyrazol-4-yl)-phenyl |
| 1377. | cyclopropylmethyl | 4-(1-methyl-1H-pyrazol-4-yl)-phenyl |
| 1378. | cyclopropylmethyl | 4-(1-ethyl-1H-pyrazol-4-yl)-phenyl |
| 1379. | cyclopropylmethyl | 4-(1-methyl-1H-pyrazol-5-yl)-phenyl |
| 1380. | cyclopropylmethyl | 4-(1H-imidazol-2-yl)-phenyl |
| 1381. | cyclopropylmethyl | 4-(imidazol-1-yl)-phenyl |
| 1382. | cyclopropylmethyl | 4-(1-methylimidazol-2-yl)-phenyl |
| 1383. | cyclopropylmethyl | 4-(oxazol-2-yl)-phenyl |
| 1384. | cyclopropylmethyl | 4-(oxazol-4-yl)-phenyl |
| 1385. | cyclopropylmethyl | 4-(oxazol-5-yl)-phenyl |
| 1386. | cyclopropylmethyl | 4-(isoxazol-3-yl)-phenyl |
| 1387. | cyclopropylmethyl | 4-(isoxazol-4-yl)-phenyl |
| 1388. | cyclopropylmethyl | 4-(isoxazol-5-yl)-phenyl |

TABLE A-continued

| No. | R¹ | Ar |
|---|---|---|
| 1389. | cyclopropylmethyl | 4-([1,2,3]-triazol-1-yl)-phenyl |
| 1390. | cyclopropylmethyl | 4-([1,2,4]-triazol-1-yl)-phenyl |
| 1391. | cyclopropylmethyl | 4-([1,2,3]-triazol-2-yl)-phenyl |
| 1392. | cyclopropylmethyl | 4-(4H-[1,2,4]-triazol-3-yl)-phenyl |
| 1393. | cyclopropylmethyl | 4-([1,2,4]-triazol-4-yl)-phenyl |
| 1394. | cyclopropylmethyl | 4-(2H-[1,2,3]-triazol-4-yl)-phenyl |
| 1395. | cyclopropylmethyl | 4-(4-methyl-4H-[1,2,4]-triazol-3-yl)-phenyl |
| 1396. | cyclopropylmethyl | 4-(2-methyl-2H-[1,2,3]-triazol-4-yl)-phenyl |
| 1397. | cyclopropylmethyl | 4-([1,3,4]-oxadiazol-2-yl)-phenyl |
| 1398. | cyclopropylmethyl | 4-([1,2,4]-oxadiazol-3-yl)-phenyl |
| 1399. | cyclopropylmethyl | 4-([1,2,4]-oxadiazol-5-yl)-phenyl |
| 1400. | cyclopropylmethyl | 4-([1,2,3]-oxadiazol-4-yl)-phenyl |
| 1401. | cyclopropylmethyl | 4-([1,2,3]-oxadiazol-5-yl)-phenyl |
| 1402. | cyclopropylmethyl | 4-([1,2,3]-thiadiazol-4-yl)-phenyl |
| 1403. | cyclopropylmethyl | 4-(1H-tetrazol-5-yl)-phenyl |
| 1404. | cyclopropylmethyl | 4-(tetrazol-1-yl)-phenyl |
| 1405. | cyclopropylmethyl | 4-(2-methyl-2H-tetrazol-5-yl)-phenyl |
| 1406. | cyclopropylmethyl | 4-(1-methyl-1H-tetrazol-5-yl)-phenyl |
| 1407. | cyclopropylmethyl | 4-furazan-3-yl-phenyl |
| 1408. | cyclopropylmethyl | 4-(pyrid-2-yl)-phenyl |
| 1409. | cyclopropylmethyl | 4-(pyrid-3-yl)-phenyl |
| 1410. | cyclopropylmethyl | 4-(pyrid-4-yl)-phenyl |
| 1411. | cyclopropylmethyl | 4-(pyrimidin-2-yl)-phenyl |
| 1412. | cyclopropylmethyl | 4-(pyrimidin-4-yl)-phenyl |
| 1413. | cyclopropylmethyl | 4-(pyrimidin-5-yl)-phenyl |
| 1414. | cyclopropylmethyl | 5-isopropylthiophen-2-yl |
| 1415. | cyclopropylmethyl | 2-chlorothiophen-5-yl |
| 1416. | cyclopropylmethyl | 2,5-dichlorothiophen-4-yl |
| 1417. | cyclopropylmethyl | 2,3-dichlorothiophen-5-yl |
| 1418. | cyclopropylmethyl | 2-chloro-3-nitrothiophen-5-yl |
| 1419. | cyclopropylmethyl | 2-(phenylsulfonyl)-thiophen-5-yl |
| 1420. | cyclopropylmethyl | 2-(pyridin-2-yl)thiophen-5-yl |
| 1421. | cyclopropylmethyl | 2-(5-(trifluoromethyl)isoxazol-3-yl)-thiophen-5-yl |
| 1422. | cyclopropylmethyl | 2-(2-methylthiazol-4-yl)-thiophen-5-yl |
| 1423. | cyclopropylmethyl | 1-methyl-1H-imidazol-4-yl |
| 1424. | cyclopropylmethyl | 1,2-dimethyl-1H-imidazol-4-yl |
| 1425. | cyclopropylmethyl | 3,5-dimethylisoxazol-4-yl |
| 1426. | cyclopropylmethyl | thiazol-2-yl |
| 1427. | cyclopropylmethyl | 4-methylthiazol-2-yl |
| 1428. | cyclopropylmethyl | 4-isopropylthiazol-2-yl |
| 1429. | cyclopropylmethyl | 4-trifluoromethylthiazol-2-yl |
| 1430. | cyclopropylmethyl | 5-methylthiazol-2-yl |
| 1431. | cyclopropylmethyl | 5-isopropylthiazol-2-yl |
| 1432. | cyclopropylmethyl | 5-trifluoromethylthiazol-2-yl |
| 1433. | cyclopropylmethyl | 2,4-dimethylthiazol-5-yl |
| 1434. | cyclopropylmethyl | 2-acetamido-4-methylthiazol-5-yl |
| 1435. | cyclopropylmethyl | 4H-[1,2,4]triazol-3-yl |
| 1436. | cyclopropylmethyl | 5-methyl-4H-[1,2,4]triazol-3-yl |
| 1437. | cyclopropylmethyl | 4-methyl-4H-[1,2,4]triazol-3-yl |
| 1438. | cyclopropylmethyl | 5-isopropyl-4H-[1,2,4]triazol-3-yl |
| 1439. | cyclopropylmethyl | 5-trifluoromethyl-4H-[1,2,4]triazol-3-yl |
| 1440. | cyclopropylmethyl | 4,5-dimethyl-4H-[1,2,4]triazol-3-yl |
| 1441. | cyclopropylmethyl | 5-isopropyl-4-methyl-4H-[1,2,4]triazol-3-yl |
| 1442. | cyclopropylmethyl | 5-trifluoromethyl-4-methyl-4H-[1,2,4]triazol-3-yl |
| 1443. | cyclopropylmethyl | [1,3,4]thiadiazol-2-yl |
| 1444. | cyclopropylmethyl | 5-methyl-[1,3,4]thiadiazol-2-yl |
| 1445. | cyclopropylmethyl | 5-isopropyl-[1,3,4]thiadiazol-2-yl |
| 1446. | cyclopropylmethyl | 5-trifluoromethyl-[1,3,4]thiadiazol-2-yl |
| 1447. | cyclopropylmethyl | 3-bromo-2-chloropyrid-5-yl |
| 1448. | cyclopropylmethyl | 2-(4-morpholino)-pyrid-5-yl |
| 1449. | cyclopropylmethyl | 2-phenoxypyrid-5-yl |
| 1450. | cyclopropylmethyl | (2-isopropyl)-pyrimidin-5-yl |
| 1451. | cyclopropylmethyl | (5-isopropyl)-pyrimidin-2-yl |
| 1452. | cyclopropylmethyl | 8-quinolyl |
| 1453. | cyclopropylmethyl | 5-isoquinolyl |
| 1454. | cyclopropylmethyl | 2-(trifluoroacetyl)-1,2,3,4-tetrahydroisoquinolin-7-yl |
| 1455. | cyclopropylmethyl | 5-chloro-3-methylbenzothiophen-2-yl |
| 1456. | cyclopropylmethyl | 3,4-dihydro-4-methyl-2H-benzo[b][1,4]oxazinyl |
| 1457. | cyclopropylmethyl | benzothiazol-6-yl |
| 1458. | cyclopropylmethyl | benzo[2,1,3]oxadiazol-4-yl |
| 1459. | cyclopropylmethyl | 5-chlorobenzo[2,1,3]oxadiazol-4-yl |
| 1460. | cyclopropylmethyl | 7-chlorobenzo[2,1,3]oxadiazol-4-yl |
| 1461. | cyclopropylmethyl | benzo[2,1,3]thiadiazol-4-yl |
| 1462. | allyl | 4-methylphenyl |
| 1463. | allyl | 4-ethylphenyl |
| 1464. | allyl | 4-propylphenyl |
| 1465. | allyl | 4-isopropylphenyl |

TABLE A-continued

| No. | R¹ | Ar |
|---|---|---|
| 1466. | allyl | 4-sec-butylphenyl |
| 1467. | allyl | 4-isobutylphenyl |
| 1468. | allyl | 4-(1,1-dimethylpropyl)-phenyl |
| 1469. | allyl | 4-vinylphenyl |
| 1470. | allyl | 4-isopropenylphenyl |
| 1471. | allyl | 4-fluorophenyl |
| 1472. | allyl | 4-chlorophenyl |
| 1473. | allyl | 4-bromophenyl |
| 1474. | allyl | 4-(fluoromethyl)phenyl |
| 1475. | allyl | 3-(fluoromethyl)phenyl |
| 1476. | allyl | 2-(fluoromethyl)phenyl |
| 1477. | allyl | 4-(difluoromethyl)phenyl |
| 1478. | allyl | 3-(difluoromethyl)phenyl |
| 1479. | allyl | 2-(difluoromethyl)phenyl |
| 1480. | allyl | 4-(trifluoromethyl)phenyl |
| 1481. | allyl | 3-(trifluoromethyl)phenyl |
| 1482. | allyl | 2-(trifluoromethyl)phenyl |
| 1483. | allyl | 4-(1-fluoroethyl)-phenyl |
| 1484. | allyl | 4-((S)-1-fluoroethyl)-phenyl |
| 1485. | allyl | 4-((R)-1-fluoroethyl)-phenyl |
| 1486. | allyl | 4-(2-fluoroethyl)-phenyl |
| 1487. | allyl | 4-(1,1-difluoroethyl)-phenyl |
| 1488. | allyl | 4-(2,2-difluoroethyl)-phenyl |
| 1489. | allyl | 4-(2,2,2-trifluoroethyl)-phenyl |
| 1490. | allyl | 4-(3-fluoropropyl)-phenyl |
| 1491. | allyl | 4-(2-fluoropropyl)-phenyl |
| 1492. | allyl | 4-((S)-2-fluoropropyl)-phenyl |
| 1493. | allyl | 4-((R)-2-fluoropropyl)-phenyl |
| 1494. | allyl | 4-(3,3-difluoropropyl)-phenyl |
| 1495. | allyl | 4-(3,3,3-trifluoropropyl)-phenyl |
| 1496. | allyl | 4-(1-fluoro-1-methylethyl)-phenyl |
| 1497. | allyl | 4-(2-fluoro-1-methylethyl)-phenyl |
| 1498. | allyl | 4-((S)-2-fluoro-1-methylethyl)-phenyl |
| 1499. | allyl | 4-((R)-2-fluoro-1-methylethyl)-phenyl |
| 1500. | allyl | 4-(2,2-difluoro-1-methylethyl)-phenyl |
| 1501. | allyl | 4-((S)-2,2-difluoro-1-methylethyl)-phenyl |
| 1502. | allyl | 4-((R)-2,2-difluoro-1-methylethyl)-phenyl |
| 1503. | allyl | 4-(2,2,2-trifluoro-1-methylethyl)-phenyl |
| 1504. | allyl | 4-((S)-2,2,2-trifluoro-1-methylethyl)-phenyl |
| 1505. | allyl | 4-((R)-2,2,2-trifluoro-1-methylethyl)-phenyl |
| 1506. | allyl | 4-(2-fluoro-1-fluoromethylethyl)-phenyl |
| 1507. | allyl | 4-(1-difluoromethyl-2,2-difluoroethyl)-phenyl |
| 1508. | allyl | 4-(1,1-dimethyl-2-fluoroethyl)-phenyl |
| 1509. | allyl | 4-methoxyphenyl |
| 1510. | allyl | 4-ethoxyphenyl |
| 1511. | allyl | 4-propoxyphenyl |
| 1512. | allyl | 4-isopropoxyphenyl |
| 1513. | allyl | 4-butoxyphenyl |
| 1514. | allyl | 4-(fluoromethoxy)-phenyl |
| 1515. | allyl | 4-(difluoromethoxy)-phenyl |
| 1516. | allyl | 4-(trifluoromethoxy)-phenyl |
| 1517. | allyl | 3-(trifluoromethoxy)-phenyl |
| 1518. | allyl | 4-(2-fluoroethoxy)-phenyl |
| 1519. | allyl | 4-(2,2-difluoroethoxy)-phenyl |
| 1520. | allyl | 4-(2,2,2-trifluoroethoxy)-phenyl |
| 1521. | allyl | 4-(1,1,2,2-tetrafluoroethoxy)-phenyl |
| 1522. | allyl | 4-cyclopropylphenyl |
| 1523. | allyl | 4-cyclobutylphenyl |
| 1524. | allyl | 4-cyclopentylphenyl |
| 1525. | allyl | 4-(2,2-difluorocyclopropyl)-phenyl |
| 1526. | allyl | 3,4-difluorophenyl |
| 1527. | allyl | 4-bromo-3-fluorophenyl |
| 1528. | allyl | 4-bromo-2-fluorophenyl |
| 1529. | allyl | 4-bromo-2,5-difluorophenyl |
| 1530. | allyl | 2-fluoro-4-isopropylphenyl |
| 1531. | allyl | 3-fluoro-4-isopropylphenyl |
| 1532. | allyl | 4-(1-hydroxy-1-methylethyl)-phenyl |
| 1533. | allyl | 4-(2-hydroxy-2-methylpropyl)-phenyl |
| 1534. | allyl | 4-acetylphenyl |
| 1535. | allyl | 4-carboxyphenyl |
| 1536. | allyl | 4-cyanophenyl |
| 1537. | allyl | 4-hydroxyphenyl |
| 1538. | allyl | 4-(O-benzyl)-phenyl |
| 1539. | allyl | 4-(2-methoxyethoxy)-phenyl |
| 1540. | allyl | 4-($CH_2$—$N(CH_3)_2$)-phenyl |
| 1541. | allyl | 4-(NH—CO—NH2)-phenyl |
| 1542. | allyl | 4-(methylsulfanyl)-phenyl |
| 1543. | allyl | 4-(fluoromethylsulfanyl)-phenyl |

TABLE A-continued

| No. | R¹ | Ar |
|---|---|---|
| 1544. | allyl | 4-(difluoromethylsulfanyl)-phenyl |
| 1545. | allyl | 4-(trifluoromethylsulfanyl)-phenyl |
| 1546. | allyl | 4-(methylsulfonyl)-phenyl |
| 1547. | allyl | 4-(N-methoxy-N-methyl-amino)-phenyl |
| 1548. | allyl | 4-(methoxyamino)-phenyl |
| 1549. | allyl | 4-(ethoxyamino)-phenyl |
| 1550. | allyl | 4-(N-methylaminooxy)-phenyl |
| 1551. | allyl | 4-(N,N-dimethylaminooxy)-phenyl |
| 1552. | allyl | 4-(azetidin-1-yl)-phenyl |
| 1553. | allyl | 4-(2-methylazetidin-1-yl)-phenyl |
| 1554. | allyl | 4-((S)-2-methylazetidin-1-yl)-phenyl |
| 1555. | allyl | 4-((R)-2-methylazetidin-1-yl)-phenyl |
| 1556. | allyl | 4-(3-fluoroazetidin-1-yl)-phenyl |
| 1557. | allyl | 4-(3-methoxyazetidin-1-yl)-phenyl |
| 1558. | allyl | 4-(3-hydroxyazetidin-1-yl)-phenyl |
| 1559. | allyl | 4-(pyrrolidin-1-yl)-phenyl |
| 1560. | allyl | 4-(pyrrolidin-2-yl)-phenyl |
| 1561. | allyl | 4-((S)-pyrrolidin-2-yl)-phenyl |
| 1562. | allyl | 4-((R)-pyrrolidin-2-yl)-phenyl |
| 1563. | allyl | 4-(pyrrolidin-3-yl)-phenyl |
| 1564. | allyl | 4-((S)-pyrrolidin-3-yl)-phenyl |
| 1565. | allyl | 4-((R)-pyrrolidin-3-yl)-phenyl |
| 1566. | allyl | 4-(2-fluoropyrrolidin-1-yl)-phenyl |
| 1567. | allyl | 4-((S)-2-fluoropyrrolidin-1-yl)-phenyl |
| 1568. | allyl | 4-((R)-2-fluoropyrrolidin-1-yl)-phenyl |
| 1569. | allyl | 4-(3-fluoropyrrolidin-1-yl)-phenyl |
| 1570. | allyl | 4-((S)-3-fluoropyrrolidin-1-yl)-phenyl |
| 1571. | allyl | 4-((R)-3-fluoropyrrolidin-1-yl)-phenyl |
| 1572. | allyl | 4-(2,2-difluoropyrrolidin-1-yl)-phenyl |
| 1573. | allyl | 4-(3,3-difluoropyrrolidin-1-yl)-phenyl |
| 1574. | allyl | 4-(2-methylpyrrolidin-1-yl)-phenyl |
| 1575. | allyl | 4-((S)-2-methylpyrrolidin-1-yl)-phenyl |
| 1576. | allyl | 4-((R)-2-methylpyrrolidin-1-yl)-phenyl |
| 1577. | allyl | 4-(3-methylpyrrolidin-1-yl)-phenyl |
| 1578. | allyl | 4-((S)-3-methylpyrrolidin-1-yl)-phenyl |
| 1579. | allyl | 4-((R)-3-methylpyrrolidin-1-yl)-phenyl |
| 1580. | allyl | 4-(1-methylpyrrolidin-2-yl)-phenyl |
| 1581. | allyl | 4-((S)-1-methylpyrrolidin-2-yl)-phenyl |
| 1582. | allyl | 4-((R)-1-methylpyrrolidin-2-yl)-phenyl |
| 1583. | allyl | 4-(1-methylpyrrolidin-3-yl)-phenyl |
| 1584. | allyl | 4-((S)-1-methylpyrrolidin-3-yl)-phenyl |
| 1585. | allyl | 4-((R)-1-methylpyrrolidin-3-yl)-phenyl |
| 1586. | allyl | 4-(2,2-dimethylpyrrolidin-1-yl)-phenyl |
| 1587. | allyl | 4-(3,3-dimethylpyrrolidin-1-yl)-phenyl |
| 1588. | allyl | 4-(2-trifluoromethylpyrrolidin-1-yl)-phenyl |
| 1589. | allyl | 4-((S)-2-trifluoromethylpyrrolidin-1-yl)-phenyl |
| 1590. | allyl | 4-((R)-2-trifluoromethylpyrrolidin-1-yl)-phenyl |
| 1591. | allyl | 4-(3-trifluoromethylpyrrolidin-1-yl)-phenyl |
| 1592. | allyl | 4-((S)-3-trifluoromethylpyrrolidin-1-yl)-phenyl |
| 1593. | allyl | 4-((R)-3-trifluoromethylpyrrolidin-1-yl)-phenyl |
| 1594. | allyl | 4-(2-oxopyrrolidin-1-yl)-phenyl |
| 1595. | allyl | 4-(2-oxo-oxazolidin-3-yl)-phenyl |
| 1596. | allyl | 4-(piperidin-1-yl)-phenyl |
| 1597. | allyl | 4-(2-methylpiperidin-1-yl)-phenyl |
| 1598. | allyl | 4-((S)-2-methylpiperidin-1-yl)-phenyl |
| 1599. | allyl | 4-((R)-2-methylpiperidin-1-yl)-phenyl |
| 1600. | allyl | 4-(piperazin-1-yl)-phenyl |
| 1601. | allyl | 4-(4-methylpiperazin-1-yl)-phenyl |
| 1602. | allyl | 4-(morpholin-4-yl)-phenyl |
| 1603. | allyl | 4-(thiomorpholin-4-yl)-phenyl |
| 1604. | allyl | 4-(1-oxo-thiomorpholin-4-yl)-phenyl |
| 1605. | allyl | 4-(1,1-dioxo-thiomorpholin-4-yl)-phenyl |
| 1606. | allyl | 4-(pyrrol-1-yl)-phenyl |
| 1607. | allyl | 4-(pyrrol-2-yl)-phenyl |
| 1608. | allyl | 4-(pyrrol-3-yl)-phenyl |
| 1609. | allyl | 4-(1-methylpyrrol-2-yl)-phenyl |
| 1610. | allyl | 4-(1-methylpyrrol-3-yl)-phenyl |
| 1611. | allyl | 4-(furan-2-yl)-phenyl |
| 1612. | allyl | 4-(furan-3-yl)-phenyl |
| 1613. | allyl | 4-(thiophen-2-yl)-phenyl |
| 1614. | allyl | 4-(thiophen-3-yl)-phenyl |
| 1615. | allyl | 4-(5-propylthien-2-yl)-phenyl |
| 1616. | allyl | 4-(pyrazol-1-yl)-phenyl |
| 1617. | allyl | 4-(pyrazol-3-yl)-phenyl |
| 1618. | allyl | 4-(pyrazol-4-yl)-phenyl |
| 1619. | allyl | 4-(1-methyl-1H-pyrazol-4-yl)-phenyl |
| 1620. | allyl | 4-(1-ethyl-1H-pyrazol-4-yl)-phenyl |
| 1621. | allyl | 4-(1-methyl-1H-pyrazol-5-yl)-phenyl |

TABLE A-continued

| No. | R¹ | Ar |
|---|---|---|
| 1622. | allyl | 4-(1H-imidazol-2-yl)-phenyl |
| 1623. | allyl | 4-(imidazol-1-yl)-phenyl |
| 1624. | allyl | 4-(1-methylimidazol-2-yl)-phenyl |
| 1625. | allyl | 4-(oxazol-2-yl)-phenyl |
| 1626. | allyl | 4-(oxazol-4-yl)-phenyl |
| 1627. | allyl | 4-(oxazol-5-yl)-phenyl |
| 1628. | allyl | 4-(isoxazol-3-yl)-phenyl |
| 1629. | allyl | 4-(isoxazol-4-yl)-phenyl |
| 1630. | allyl | 4-(isoxazol-5-yl)-phenyl |
| 1631. | allyl | 4-([1,2,3]-triazol-1-yl)-phenyl |
| 1632. | allyl | 4-([1,2,4]-triazol-1-yl)-phenyl |
| 1633. | allyl | 4-([1,2,3]-triazol-2-yl)-phenyl |
| 1634. | allyl | 4-(4H-[1,2,4]-triazol-3-yl)-phenyl |
| 1635. | allyl | 4-([1,2,4]-triazol-4-yl)-phenyl |
| 1636. | allyl | 4-(2H-[1,2,3]-triazol-4-yl)-phenyl |
| 1637. | allyl | 4-(4-methyl-4H-[1,2,4]-triazol-3-yl)-phenyl |
| 1638. | allyl | 4-(2-methyl-2H-[1,2,3]-triazol-4-yl)-phenyl |
| 1639. | allyl | 4-([1,3,4]-oxadiazol-2-yl)-phenyl |
| 1640. | allyl | 4-([1,2,4]-oxadiazol-3-yl)-phenyl |
| 1641. | allyl | 4-([1,2,4]-oxadiazol-5-yl)-phenyl |
| 1642. | allyl | 4-([1,2,3]-oxadiazol-4-yl)-phenyl |
| 1643. | allyl | 4-([1,2,3]-oxadiazol-5-yl)-phenyl |
| 1644. | allyl | 4-([1,2,3]-thiadiazol-4-yl)-phenyl |
| 1645. | allyl | 4-(1H-tetrazol-5-yl)-phenyl |
| 1646. | allyl | 4-(tetrazol-1-yl)-phenyl |
| 1647. | allyl | 4-(2-methyl-2H-tetrazol-5-yl)-phenyl |
| 1648. | allyl | 4-(1-methyl-1H-tetrazol-5-yl)-phenyl |
| 1649. | allyl | 4-furazan-3-yl-phenyl |
| 1650. | allyl | 4-(pyrid-2-yl)-phenyl |
| 1651. | allyl | 4-(pyrid-3-yl)-phenyl |
| 1652. | allyl | 4-(pyrid-4-yl)-phenyl |
| 1653. | allyl | 4-(pyrimidin-2-yl)-phenyl |
| 1654. | allyl | 4-(pyrimidin-4-yl)-phenyl |
| 1655. | allyl | 4-(pyrimidin-5-yl)-phenyl |
| 1656. | allyl | 5-isopropylthiophen-2-yl |
| 1657. | allyl | 2-chlorothiophen-5-yl |
| 1658. | allyl | 2,5-dichlorothiophen-4-yl |
| 1659. | allyl | 2,3-dichlorothiophen-5-yl |
| 1660. | allyl | 2-chloro-3-nitrothiophen-5-yl |
| 1661. | allyl | 2-(phenylsulfonyl)-thiophen-5-yl |
| 1662. | allyl | 2-(pyridin-2-yl)thiophen-5-yl |
| 1663. | allyl | 2-(5-(trifluoromethyl)isoxazol-3-yl)-thiophen-5-yl |
| 1664. | allyl | 2-(2-methylthiazol-4-yl)-thiophen-5-yl |
| 1665. | allyl | 1-methyl-1H-imidazol-4-yl |
| 1666. | allyl | 1,2-dimethyl-1H-imidazol-4-yl |
| 1667. | allyl | 3,5-dimethylisoxazol-4-yl |
| 1668. | allyl | thiazol-2-yl |
| 1669. | allyl | 4-methylthiazol-2-yl |
| 1670. | allyl | 4-isopropylthiazol-2-yl |
| 1671. | allyl | 4-trifluoromethylthiazol-2-yl |
| 1672. | allyl | 5-methylthiazol-2-yl |
| 1673. | allyl | 5-isopropylthiazol-2-yl |
| 1674. | allyl | 5-trifluoromethylthiazol-2-yl |
| 1675. | allyl | 2,4-dimethylthiazol-5-yl |
| 1676. | allyl | 2-acetamido-4-methylthiazol-5-yl |
| 1677. | allyl | 4H-[1,2,4]triazol-3-yl |
| 1678. | allyl | 5-methyl-4H-[1,2,4]triazol-3-yl |
| 1679. | allyl | 4-methyl-4H-[1,2,4]triazol-3-yl |
| 1680. | allyl | 5-isopropyl-4H-[1,2,4]triazol-3-yl |
| 1681. | allyl | 5-trifluoromethyl-4H-[1,2,4]triazol-3-yl |
| 1682. | allyl | 4,5-dimethyl-4H-[1,2,4]triazol-3-yl |
| 1683. | allyl | 5-isopropyl-4-methyl-4H-[1,2,4]triazol-3-yl |
| 1684. | allyl | 5-trifluoromethyl-4-methyl-4H-[1,2,4]triazol-3-yl |
| 1685. | allyl | [1,3,4]thiadiazol-2-yl |
| 1686. | allyl | 5-methyl-[1,3,4]thiadiazol-2-yl |
| 1687. | allyl | 5-isopropyl-[1,3,4]thiadiazol-2-yl |
| 1688. | allyl | 5-trifluoromethyl-[1,3,4]thiadiazol-2-yl |
| 1689. | allyl | 3-bromo-2-chloropyrid-5-yl |
| 1690. | allyl | 2-(4-morpholino)-pyrid-5-yl |
| 1691. | allyl | 2-phenoxypyrid-5-yl |
| 1692. | allyl | (2-isopropyl)-pyrimidin-5-yl |
| 1693. | allyl | (5-isopropyl)-pyrimidin-2-yl |
| 1694. | allyl | 8-quinolyl |
| 1695. | allyl | 5-isoquinolyl |
| 1696. | allyl | 2-(trifluoroacetyl)-1,2,3,4-tetrahydroisoquinolin-7-yl |
| 1697. | allyl | 5-chloro-3-methylbenzothiophen-2-yl |
| 1698. | allyl | 3,4-dihydro-4-methyl-2H-benzo[b][1,4]oxazinyl |

TABLE A-continued

| No. | R¹ | Ar |
|---|---|---|
| 1699. | allyl | benzothiazol-6-yl |
| 1700. | allyl | benzo[2,1,3]oxadiazol-4-yl |
| 1701. | allyl | 5-chlorobenzo[2,1,3]oxadiazol-4-yl |
| 1702. | allyl | 7-chlorobenzo[2,1,3]oxadiazol-4-yl |
| 1703. | allyl | benzo[2,1,3]thiadiazol-4-yl |
| 1704. | allyl | 6-chloroimidazo[2,1-b]thiazolyl |

The compounds of the formula I where E is NH and $R^{1a}$ is hydrogen can be prepared by analogy to methods which are well known in the art, e.g. from the international patent applications cited in the introductory part. A preferred method for the preparation of compounds I is outlined in scheme 1:

for example, J. March, Advanced Organic Chemistry, 3rd ed., J. Wiley & Sons, New-York, 1985, p. 1183 and the literature cited in this reference). The reduction is achieved, for example, by reacting the nitro compound VII with a metal such as iron, zinc or tin under acidic reaction conditions, i.e.

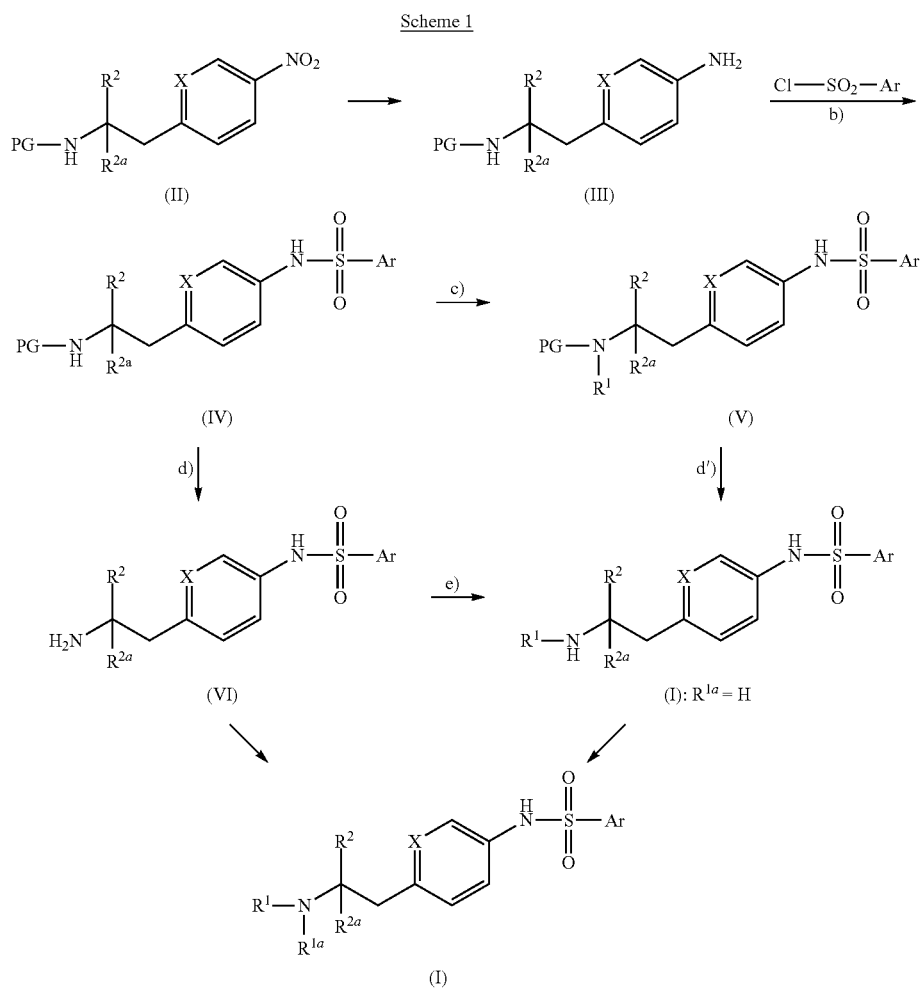

In scheme 1, $R^1$, $R^2$, $R^2$, X and Ar have the meanings as given above. PG is an amino-protecting group such as tert.-butoxycarbonyl. Suitable protecting groups are disclosed, for example, in P. Kocienski, Protecting Groups, Thieme-Verlag, Stuttgart 2000, Chapter 6.

In step a) the protected nitrophenethylamine II is reduced by conventional means into the corresponding amino compound III. The required reaction conditions correspond to the customary conditions for reducing aromatic nitro groups which have been described extensively in the literature (see, using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of II to III can be carried out with hydrogen in the presence of a transition metal catalyst, e.g.

using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound II, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of II with tin(II) chloride is preferably carried out in an inert organic solvent, preferably an alcohol such as methanol, ethanol, isopropanol or butanol.

The thus obtained compound III is reacted with an arylchlorosulfonylchloride $C_1$—$SO_2$—Ar, preferably in the presence of a base, according to standard procedures in the art to obtain compound IV. The reaction depicted in scheme 1 step b) takes place under the reaction conditions which are customary for preparing arylsulfonamide compounds or arylsulfonic esters, respectively, and which are described, for example, in J. March, Advanced Organic Chemistry, $3^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of III with $C_1$—$SO_2$—Ar is customarily carried out in the presence of an auxiliary base. Suitable bases are inorganic bases, such as sodium carbonate or potassium carbonate, or sodium hydrogencarbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound III.

The thus obtained compound can be alkylated or acylated in step c with a compound $R^1$-L, wherein $R^1$ has the meanings given above and L is a leaving group that can be replaced by the nucleophilic amino group. Leaving groups L comprise e.g. halogen, trifluoroacetate, arylsulfonyloxy such as tosylate, phenylsulfonyloxy, $C_1$-$C_4$-alkylsulfonyloxy, trifluoromethylsulfonyloxy, $C_1$-$C_4$-alkoxysulfonyloxy, etc. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

In step d') the protecting group PG is cleaved by conventional means (see e.g. P. Kocienski, Protecting Groups, Thieme-Verlag, Stuttgart 2000, Chapter 6) thereby obtaining a compound I, wherein $R^{1a}$ is hydrogen. This compound can be further reacted by alkylation or acylation with $R^{1a}$-L, wherein L has the meanings given above and $R^{1a}$ is as defined above but different from hydrogen.

It is also possible to first cleave the protecting group in IV (step d), thereby obtaining the compound VI and then to introduce the radical $R^1$ and optionally $R^{1a}$ (step e). The introduction of the radical $R^1$ into compound VI can also be achieved, in the sense of a reductive amination, by reacting VI with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273. The introduction of the radical $R^1$ into compound VI can also be achieved by reacting VI with a suitable acyl halide to obtain a compound of the formula I wherein $R^1$ is $C_1$-$C_3$-alkylcarbonyl. The carbonyl group in these compounds can be reduced with diborane to obtain compounds of the general formula I, wherein R is $C_2$-$C_4$-alkyl. The carbonyl group can also be reacted with a fluorinating agent to obtain a compound I wherein $R^1$ is 1,1-difluoroalkyl. Acylation and reduction can be achieved by standard methods, which are discussed in J. March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

The starting materials of the formula II can be simply obtained from commercially available phenethylamines by selectively protecting the aliphatic amino group of these compounds according to standard methods (see e.g. P. Kocienski, Protecting Groups, loc. cit.).

A skilled person will also appreciate that the reactions of step b) and c) as well as steps b) and d) can be exchanged, e.g. by performing the reaction of step c) first and then the reaction of step b).

A skilled person will also appreciate that compounds of the formula I with E=N—$R^3$, wherein $R^3$ is different from hydrogen, can be obtained by selective alkylation of the sulfonamide group in the compounds of the formulae V, VI or I.

If $R^1$ or $R^{1a}$ in compound I is (are) allyl the allyl group(s) can be cleaved to obtain a compound I' or I'' wherein R is hydrogen. The cleavage of the allyl group is achieved, for example, by reacting I [$R^1$=allyl] with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis(triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I Organic, and Bio-Organic Chemistry 1999 (21) pp. 3089-3104 and Tetrahedron Asymmetry 1997, 8(20), pp. 3387-3391). If $R^1$ or $R^{1a}$ in compound I is (are) allyl the allyl group can be also converted into a n-propyl group by hydrogenation in the presence of Pd—C as a catalyst.

Compounds of the formula I, wherein $R^{1a}$ and $R^2$ or $R^{1a}$ and $R^{2a}$ together are $(CH_2)_n$ with n being 2, 3 or 4 can be prepared in a manner similar to the method outlined in scheme 1 starting from a compound of the formula VII, by the method outlined in scheme 2 (showing the sequence for $R^{1a}$ and $R^2$ together are $(CH_2)_n$).

Scheme 2:

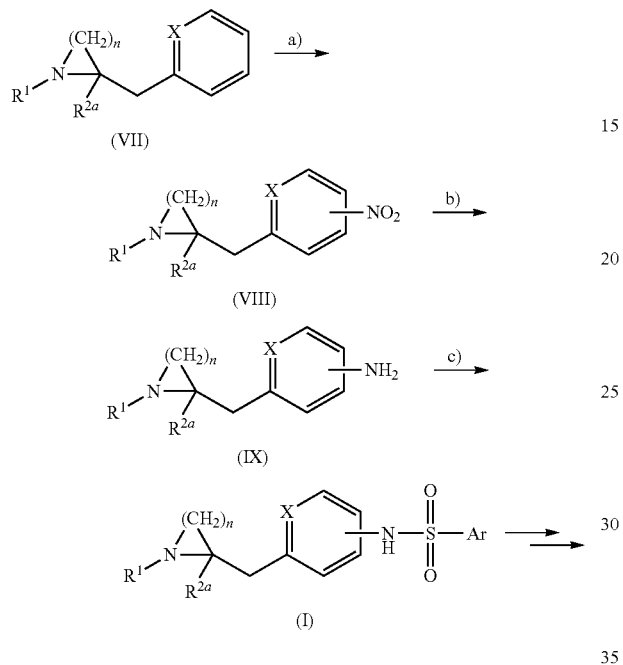

In scheme 2, $R^1$, $R^{2a}$, n and Ar have the meanings given above.

The reaction depicted in step a) in scheme 2 takes place under the reaction conditions which are customary for a nitration of an aromatic radical and which are described, for example, in J. March, Advanced Organic Chemistry, 3rd ed., John Wiley & Sons, New York 1985, pp 468-470 and the literature cited therein). In step b), the nitro group in VIII is reduced to the $NH_2$ group according to the method of step b) in scheme 1. Step c) in scheme 2 corresponds to step b) in scheme 1, which can be performed in analogous manner. Thereby a compound of the general formula VIII is obtained.

The radical R in the thus obtained compounds VIII can be transformed into other radicals by the methods outlined in connection with scheme 1.

Compounds of the formula VII are known in the art or can be prepared according to standard procedures.

Compounds of the formula I, where $R^{2a}$ is H, X is N and E is NH can be also obtained by the synthetic approach outlined in scheme 3. In scheme 3, $R^2$ and Ar have the meanings given above.

Scheme 3:

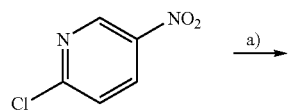

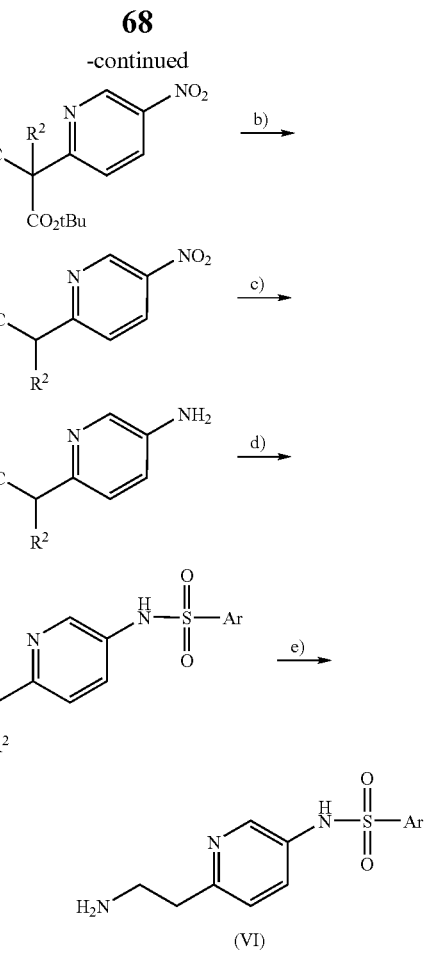

step a: $K_2CO_3$ in tetrahydrofuran step b: p-toluene sulfonic acid, toluene step c: reduction (see step a of scheme 1)

step d: reaction with $Ar—SO_2—Cl$ (see step b of scheme 1)

step e: reduction, e.g. by $H_2$/Raney nickel, $NH_3$

The obtained compound VI can be further reacted as outlined in scheme 1 to obtain compound I.

The compounds of the formula I where E is $CH_2$ as outlined in schemes 4a and 4b:

Scheme 4a:

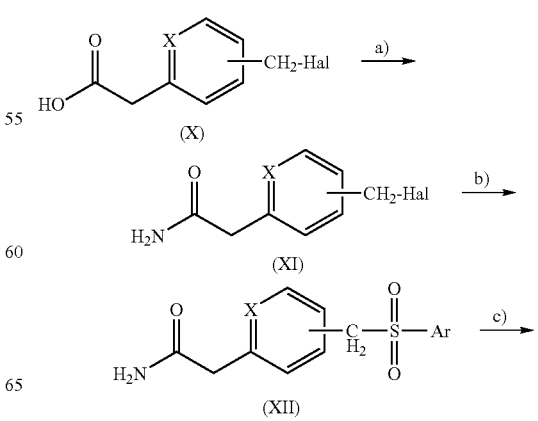

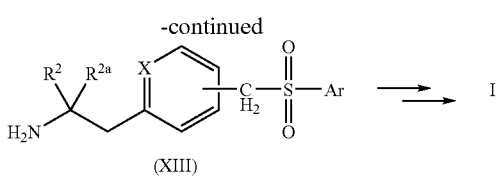

Scheme 4b:

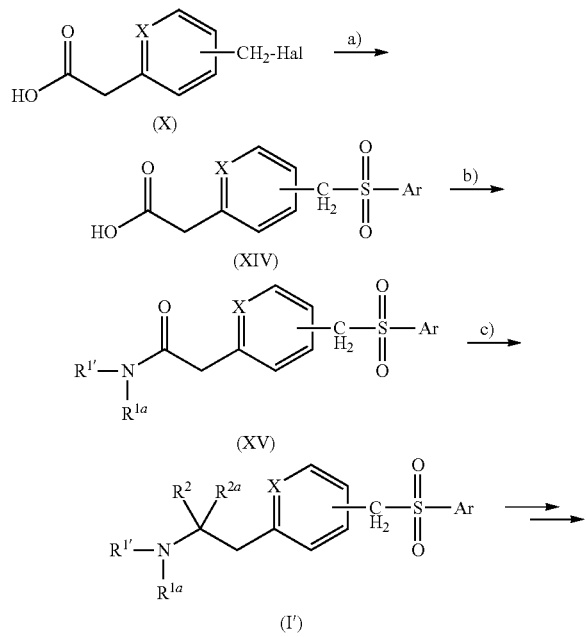

In schemes 4a and 4b, X, $R^{1a}$, $R^2$, $R^{2a}$, and Ar have the meanings given above. $R^{1'}$ is a radical $R^1$ that is different from hydrogen, formyl or alkylcarbonyl. Hal is halogen, in particular bromine.

According to scheme 4a, the carboxyl group in compound X is transformed into the carboxamide group by standard methods, e.g. by successively reacting compound X with thionyl chloride and then with aqueous ammonia. The amide XI is then reacted in step b) with a mercapto compound HS—Ar in the presence of a base, such as sodium hydride or sodium alkoxide or with an alkali metal salt of HS—Ar, thereby yielding thioether compound. The thioether moiety is oxidized to a sulfone moiety, e.g. by oxone to obtain compound XII. Compound XII can be either reduced, e.g. by $BH_3$-Dimethylsulfide, to obtain compound XIII with $R^2=R^{2a}=H$, or reacted with a suitable organometal compound or successively with a reducing agent and an organometal compound to obtain a compound XIII, where $R^2$ and/or $R^{2a}$ is (are) different from hydrogen. Compound XIII can be further converted into compound I as outlined for scheme 1.

According to scheme 4b, compound X is reacted in step a) with a mercapto compound HS—Ar in the presence of a base, such as sodium hydride or sodium alkoxide or with an alkali metal salt of HS—Ar, thereby yielding thioether compound. The thioether moiety is oxidized to a sulfone moiety, e.g. by oxone to obtain compound XIV. Compound XIV is reacted in step b) with an amine $R^{1'}R^{1a}NH$ in the presence of a dehydrating agent such as cyclohexylcarbodiimide (CDI). Compound XV can be either reduced, e.g. by $BH_3$-dimethylsulfide, to obtain compound I' with $R^2=R^{2a}=H$, or reacted with a suitable organometal compound or successively with a reducing agent and an organometal compound to obtain a compound I', where $R^2$ and/or $R^{2a}$ is (are) different from hydrogen. Compound I' can be further converted into other compounds I as outlined for scheme 1.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", Andre Loupy (Ed.), Wiley-VCH 2002.

The sulfonylchlorides $C_1$—$SO_2$—Ar are either commercially available or can be prepared according to standard synthetic methods. Sulfonylchlorides containing a fluorinated radical $R^a$ may be prepared by different synthetic routes, e.g. by reacting suitable hydroxy or oxo precursor (e.g. a compound $C_1$—$SO_2$—Ar, carrying a hydroxy or oxo substituted radical) with fluorinating reagents like DAST (diethylaminosulfurtrifluoride), morpholine-DAST, deoxofluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group is transformed into a leaving group which is then replaced by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorus pentachloride (Eur. J. Med. Chem., 2002, 36, 809-828) and the like, yields the desired sulfonylchloride (Tetrahedron Letters, 1991, 33, 50 7787-7788)) Sulfonylchlorides may also be prepared by diazotation of suitable amine precursor Ar—$NH_2$ with sodium nitrite under acidic conditions and reaction with sulfur dioxide in acetic acid (scheme (iii); J. Org. Chem., 1960, 25, 1824-26;); by oxidation of suitable heteroaryl-thiols HS—Ar or heteroaryl-benzyl-thioethers $C_6H_5$—$CH_2$—S—Ar with chlorine (Synthesis, 1998, 36-38; J. Am. Chem. Soc., 1950, 74, 4890-92;) directly to the corresponding sulfonyl chlorides. The further are known in the art or may be prepared by standard methods. E.g. mercapto-pyrimidines or pyrimidinyl-benzylthioether precursors can e.g. be prepared according to literature (Chemische Berichte, 1960, 1208-11; Chemische Berichte, 1960, 95, 230-235; Collection Czechoslow. Chem. Comm., 1959, 24, 1667-1671; Austr. J. Chem., 1966, 19, 2321-30; Chemiker-Zeitung, 101, 6, 1977, 305-7; Tetrahedron, 2002, 58, 887-890; Synthesis, 1983, 641-645.

The aminocompounds of the formulae III or IX may also be prepared from the corresponding halogen compound XVI or XVII according to the method as described in scheme 5:

SCHEME 5

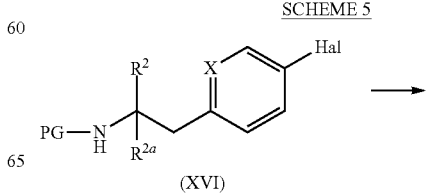

-continued

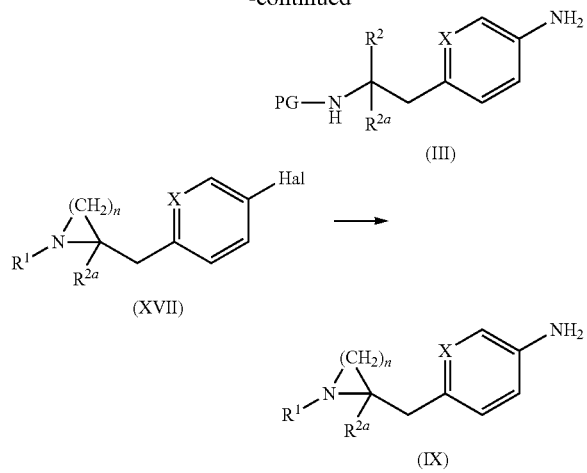

In scheme 5, $R^1$, $R^2$, $R^{2a}$, n and X are as defined above. Hal is halogen, in particular bromine, and PG is a protecting group. The reaction can be performed by reacting XVI or XVII, respectively, with an alkalimetal salt of a bis(trialkylsilyl)amine such as lithium bis(trimethylsilyl)amide in the presence of a palladium catalyst and subsequent hydrolysis. An example for a suitable palladium catalyst is tris(dibenzylideneacetone)dipalladium(0), optionally in the presence of a tri(substituted)phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexylphosphine), or $PdCl_2$(dppf). The reaction of VIIa with the alkalimetal-bis(trialkylsilyl)amide can be performed by analogy to a Buchwald-Hartig coupling the alkalimetal-bis(trialkylsilyl)amide can be generated in-situ from the corresponding amine by a strong base such an alkalimetal alkoxide, e.g. potassium tert.-butylate or an alkalimetal hydride such as lithium hydride, sodium hydride and the like. Hydrolysis is simply achieved by aqueous work-up.

Compounds of the formulae XVI or XVII may also serve as a starting material in the synthetic route depicted in scheme 6.

Scheme 6:

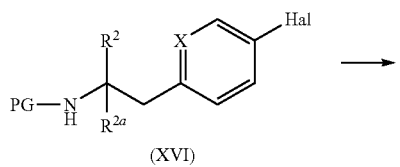

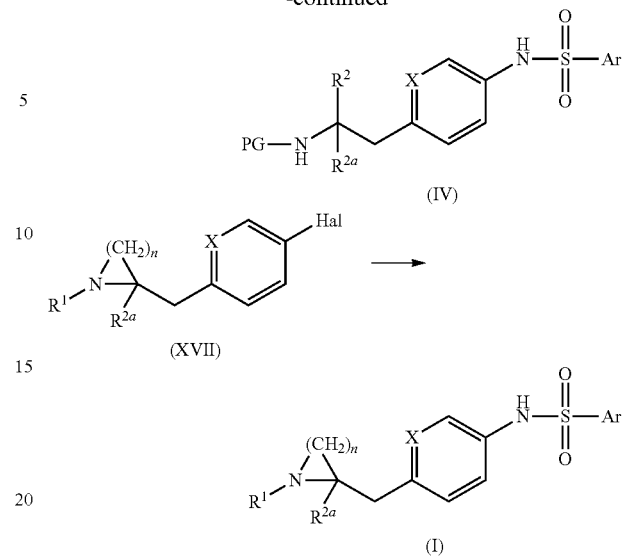

In scheme 6, $R^1$, $R^2$, $R^{2a}$, n, Ar and X are as defined above. Hal is halogen, in particular bromine, and PG is a protecting group. According to scheme 6, a compound of the formulae XVI or VXVII is reacted with an arylsulfonylamide $Ar—SO_2—NH_2$ or the lithium salt thereof in the presence of a palladium(0) compound such as tris(dibenzylideneacetone)-dipalladium(0) in the presence of a tri(substituted) phosphine, e.g. a triarylphosphine such as triphenylphosphine or tritolylphosphine, tri(cyclo)alkylphosphine such as tris-n-butylphosphine, tris(tert.-butyl)phosphine or tris(cyclohexylphosphine), preferably in the presence of a base such as sodium hydride according to the method described in J. Org. Chem., 68 (2993) pp 8274-8276, and outlined below.

A skilled person will readily appreciate that compounds of the formula I can also be obtained from structurally similar compounds by functional group interconversion. In particular N-bound radicals $R^a$ can be introduced into compounds of the formula I by reacting the corresponding halogen compound, i.e. a compound of the formula I, which instead of $R^a$ carries a halogen atom, in particular a bromine or iodine atom, with a primary or secondary amine in the presence of a base, preferably also in the presence of a palladium catalyst in terms of a Buchwald-Hartwig reaction.

In the following schemes 7 to 9 several routes are shown which are suitable to prepare benzenesulfonyl chlorides carrying a fluorinated propyl radical.

Scheme 7:

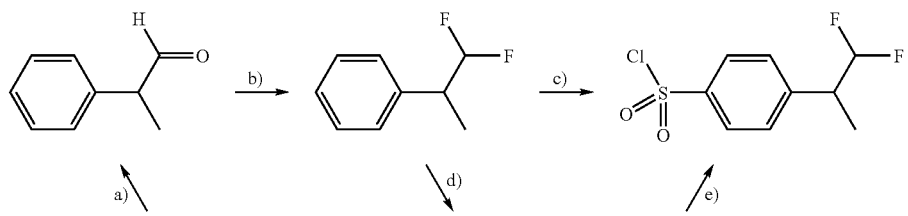

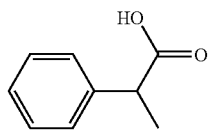
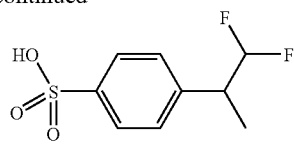

The 4-(1,1-difluoropropan-2-yl)benzene-1-sulfonyl chloride intermediate can be prepared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, $SO_2Cl_2$). The ester can be reduced to the corresponding 2-phenyl propanal by a reducing agent such as DIBAL (diisobutylaluminum hydride). The aldehyde is converted to the 1,1-difluoro-2-propyl derivative by reaction with a suitable fluorinating reagent like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 7 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 8:

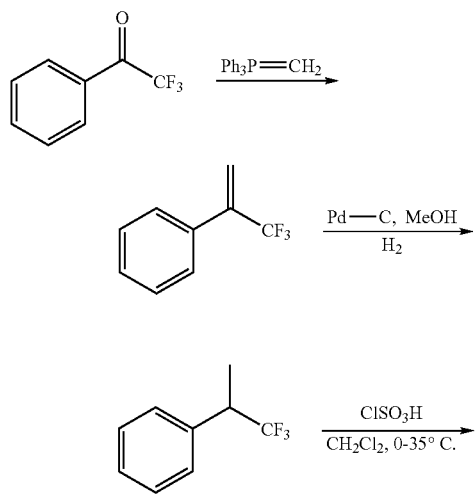

-continued

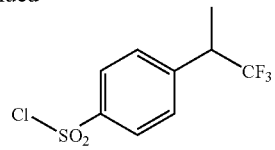

4-(1,1,1-Trifluoropropan-2-yl)benzene-1-sulfonyl chloride intermediate can be prepared from the commercially available 2,2,2-trifluoro-1-phenylethanone by a synthetic route shown in scheme 6. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 5.

The synthesis of scheme 8 can also be performed using a chiral catalyst for the alkene hydrogenation to allow the preparation of the corresponding chiral 4-(1,1,1-triifluoropropan-2-yl)benzene-1-sulfonyl chlorides.

Scheme 9:

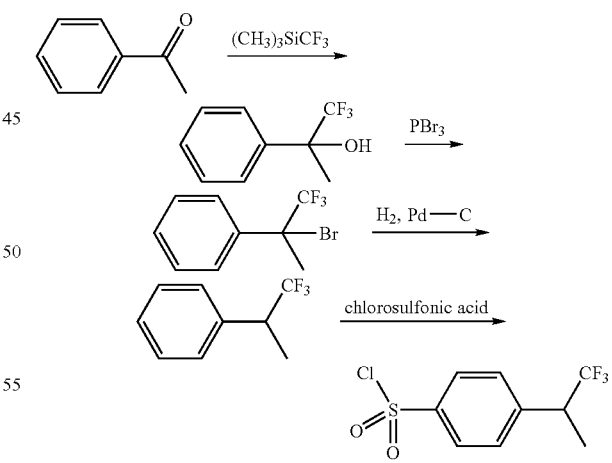

The 4-(1,1,1-trifluoropropan-2-yl)benzene-1-sulfonyl chloride can be also prepared from the commercially available 1-phenyl-ethanone by a four step procedure as shown in scheme 9. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are surprisingly highly selective dopamine $D_3$ receptor ligands which, because of their low affinity for other receptors such as $D_1$ receptors, $D_4$ receptors, $\alpha$1-adrenergic and/or $\alpha$2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists. A compound of the invention can be a dopamine $D_3$ receptor agonist, including partial agonistic activity, or a dopamine $D_3$ receptor antagonist, including partial antagonistic activity.

The high affinity of the compounds according to the invention for $D_3$ receptors is reflected in very low in-vitro receptor binding constants ($K_i(D_3)$ values) of as a rule less than 50 nM (nmol/l), preferably of less than 10 nM and, in particular of less than 5 nM. The displacement of $[^{125}I]$-iodosulpride can, for example, be used in receptor binding studies for determining binding affinities for $D_3$ receptors.

The selectivity of the compounds according to the invention, i.e. the ratio $K_i(D_2)/K_i(D_3)$ of the receptor binding constants, is as a rule at least 50, preferably at least 100, even better at least 150. The displacement of $[^3H]SCH23390$, $[^{125}I]$ iodosulpride or $[^{125}I]$ spiperone can be used, for example, for carrying out receptor binding studies on $D_1$, $D_2$ and $D_4$ receptors.

Because of their binding profile, the compounds can be used for treating diseases which respond to dopamine $D_3$ receptor ligands (or which are susceptible to treatment with a dopamine $D_3$ receptor ligand, respectively), i.e. they are effective for treating those medical disorders or diseases in which exerting an influence on (modulating) the dopamine $D_3$ receptors leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive-function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disorders which can be treated in accordance with the invention also include Parkinson's disease and epilepsy and, in particular, the affective disturbances connected thereto.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of dopamine $D_3$ receptors.

According to another aspect of the present invention, the treatment is directed, in particular, toward those disorders which can be influenced, within the sense of an expedient medicinal treatment, by the binding of preferably exogenously administered binding partners (ligands) to dopamine $D_3$ receptors.

The diseases which can be treated with the compounds according to the invention are frequently characterized by progressive development i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional liability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Therefore the compounds according to the invention are preferentially suitable for treating diseases of the central nervous system, in particular for treating affective disorders; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847 and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

The compounds were either characterized via proton-NMR in d$_6$-dimethylsulfoxide or d-chloroform, if not stated otherwise, on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

I. Preparation of Intermediates a. Preparation of 2-Aminopropylphenylamines a.1 4-((S)-2-Amino-propyl)-phenylamine×HCl

A mixture of 4-nitrophenylacetone (5 g, 27.91 mmol), (S)-(−)-α-phenylethylamine (3.4 g, 28.06 mmol), and platin (IV) oxide (100 mg) in methanol (MeOH) (50 ml) was hydrogenated at atmospheric pressure for a period of 8 h. After filtration and evaporation of the solvent under reduced pressure 4-[(S)-2-((S)-1-phenyl-ethylamino)-propyl]-phenylamine was obtained as a yellow oil 6.7 g, 94%). Without further purification a solution of this oil in methanol (100 ml) together with ammonium formate (16.4 g, 260.1 mmol), and 10% palladium on charcoal (200 mg) were heated to reflux for 30 h. The mixture was evaporated under reduced pressure and the residue was partitioned between ethyl acetate and water. The organic layer was dried over MgSO$_4$ and evaporated under reduced pressure. To a solution of the obtained residue in isopropanol HCl in isopropanol was added. The hydrochloride salt was collected and dried in a vacuum oven at 50° C. to give orange crystals (900 mg, 17%).

a.2 4-((R)-2-Amino-propyl)-phenylamine×HCl

Starting from 4-nitrophenylacetone (5 g, 27.91 mmol) and (R)-(−)-α-phenylethylamine (3.4 g, 28.06 mmol) following the same synthetic procedure as described for 4-((S)-2-amino-propyl)-phenylamine×HCl the product was obtained as a yellow powder (3 g, 57%).

b. Preparation of N-Substituted propionamides b.1 N-[1,1-Dimethyl-2-(4-nitro-phenyl)-ethyl]-propionamide b.1.1: N-(1,1-Dimethyl-2-phenyl-ethyl)-propionamide

To a solution of (2-methyl-propenyl)-benzene (2.6 g, 19.67 mmol) in propionitrile (20 g, 363 mmol) H$_2$SO$_4$ (39.33 mmol) was added at 10° C. The mixture was stirred at room temperature for 16 h. Then the mixture was poured into water and adjusted to an alkaline pH with NaOH. The aqueous layer was extracted three times with ethyl acetate, the organic layers combined, washed with water and brine, dried over MgSO$_4$, filtered, and the solvent evaporated under reduced pressure to give the product as a yellow oil (1.6 g, 40%).

b.1.2: N-[1,1-Dimethyl-2-(4-nitro-phenyl)-ethyl]-propionamide

To H$_2$SO$_4$(20 ml) at 0-10° C. N-(1,1-dimethyl-2-phenyl-ethyl)-propionamide was slowly added. The mixture was stirred until a clear solution was obtained. Then KNO$_3$ (750 mg, 7.42 mmol) was added in portions at 0-5° C. The mixture was stirred at room temperature for 16 h after which it was poured into ice water. The aqueous layer was extracted three times with ethyl acetate. The combined organic layers were washed with NaOH, water and brine, dried over MgSO$_4$, filtered, and the solvent evaporated under reduced pressure to give the product as a brown oil (1 g, 55%).

b.2 N-[1-(4-Nitro-benzyl)-cyclopropyl]-propionamide b.2.1: 1-Benzylcyclopropylamine

To a solution of phenylacetonitrile (3 g, 25.61 mmol) and tetraisopropylorthotitanate (8 ml, 27.15 mmol) in diethyl ether (Et$_2$O)/tetrahydrofuran (THF) (1/1, 100 ml) ethyl-magnesiumbromide (49.33 mmol) was added at room temperature. The exothermic mixture was stirred for 1 h at room temperature. Then BF$_3$×Et$_2$O (49.34 mmol) was added and the mixture was stirred for 1 h. The mixture was poured into a cold aqueous solution of NaOH (10%) and diluted with ethyl acetate. The mixture was filtered, and the organic layer was washed with water and brine, dried over MgSO$_4$, filtered, and the solvent evaporated under reduced pressure to give the product as a yellow oil (3.6 g, 96%).

MS (ESI) m/z: 148.15 [M+H]$^+$ b.2.2: N-(1-Benzyl-cyclopropyl)-propionamide

To a solution of 1-benzylcyclopropylamine (3.6 g, 24.45 mmol) and triethylamine (4.9 g, 48.85 mmol) in dichloromethane (100 ml) propionyl chloride (2 g, 27.02 mmol) was added at 10° C. The mixture was stirred at room temperature for 16 h. The mixture was partitioned between water and dichloromethane. The organic layer was washed with water, dried over MgSO$_4$ and the solvent evaporated under reduced pressure. The residue was triturated with diethylether, the precipitate filtered and dried in vacuo to give the product as a brown powder (2 g, 40%).

MS (ESI) m/z: 204.10 [M+H]$^+$ b.2.3: N-[1-(4-Nitro-benzyl)-cyclopropyl]-propionamide

To H$_2$SO$_4$(20 ml) at 0-10° C. N-(1-benzyl-cyclopropyl)-propionamide (2 g, 9.84 mmol) was slowly added. The mixture was stirred until a clear solution was obtained. Then KNO$_3$ (1 g, 9.89 mmol) was added in portions at 0-5° C. The mixture was stirred at room temperature for 16 h after which it was poured into ice water, and 50% NaOH was added. The aqueous layer was extracted three times with ethyl acetate. The combined organic layers were washed with water and brine, dried over MgSO$_4$, filtered, and the solvent evaporated under reduced pressure. The residue was triturated with isopropylether and the precipitate filtered and dried in vacuo to give the product as a brown powder (900 mg, 37%).

MS (ESI) m/z: 249.25 [M+H]$^+$ c. Preparation of [2-(aminophenyl)ethyl]-carbamicacid tert-butyl ester c. 1 [2-(4-Amino-phenyl)-ethyl]-carbamicacid tert-butyl ester c.1.1: [2-(4-Nitro-phenyl)-ethyl]-carbamicacid tert-butyl ester

To a solution of 2-(4-nitrophenyl)ethylamine (25.2 g, 124.31 mmol) in Tetrahydrofuran (THF) (100 ml) at 0° C. di-tert-butyl dicarbonate (38.5 g, 176.33 mmol) was added slowly. The mixture was stirred at room temperature for 16 h. After filtration the mixture was concentrated in vacuo and the residue partitioned between ethyl acetate and saturated aqueous NaHCO$_3$. The organic layer was washed with citric acid (5%), dried over MgSO$_4$, filtered and the solvent evaporated under reduced pressure to give the product as a yellow powder (18.8 g, 57%).

c.1.2: [2-(4-Amino-phenyl)-ethyl]-carbamicacid tert-butyl ester

To a solution of [2-(4-nitro-phenyl)-ethyl]-carbamicacid tert-butyl ester (18.7 g, 70.30 mmol) in ethanol (200 ml) a slurry of 10% palladium on charcoal (2 g) in water (10 ml) was added. At 80° C. ammonium formate (44.3 g, 703 mmol) in water (90 ml) was added slowly. After complete addition the mixture was stirred at 80° C. for 1 h. The mixture was allowed to come to room temperature, filtered and concentrated in vacuo. The residue was diluted with water and extracted twice with dichloromethane. The combined organic layers were washed with water, dried over MgSO$_4$, filtered and the solvent evaporated under reduced pressure to give the product as a yellow oil (13.5 g, 81%).

c.2 Allyl-[2-(4-amino-phenyl)-ethyl]-carbamic acid tert-butyl ester

To a solution of [2-(4-amino-phenyl)-ethyl]-carbamicacid tert-butyl ester (2.32 g, 9.82 mmol) in N,N-dimethylformamide (DMF) (50 ml) 18-crown-6 (50 mg) was added. At 0° C. potassium tert-butylate (1.10 g, 9.82 mmol) was added and the mixture stirred for 30 min. After the addition of allylbromide (1.19 g, 9.82 mmol) the mixture was stirred at room temperature for 16 h. After concentration in vacuo the residue was partitioned between ethyl acetate and saturated aqueous NaHCO$_3$. The organic layer was washed with water, dried over MgSO$_4$, filtered and the solvent evaporated under reduced pressure to give the product as a red oil (2.50 g, 92%).

c.3 [2-(3-Amino-phenyl)-ethyl]-carbamicacid tert-butyl ester c.3.1: 2-(3-Nitrophenyl)ethylamine

A solution of (3-nitro-phenyl)-acetonitrile (11.4 g, 70.4 mmol) in THF (100 ml) was heated to reflux and borane dimethylsulfide (2M in THF, 77.34 mmol) was added. The mixture was stirred for 2 h under reflux. After complete conversion the mixture was allowed to come to room temperature and a solution of HCl in ethanol (1M) was added. After stirring the mixture for 30 min it was concentrated under reduced pressure. The residue was triturated with diethylether, filtered, washed with diethylether and dried in vacuo to give the product as a yellow powder (13.1 g, 92%).

c.3.2: [2-(3-Amino-phenyl)-ethyl]-carbamicacid tert-butyl ester

The desired product was obtained as a brown oil following the synthetic procedure described for allyl-[2-(4-amino-phenyl)-ethyl]-carbamic acid tert-butyl ester starting from 2-(3-Nitrophenyl)ethylamine.

c.4 Allyl-[2-(3-amino-phenyl)-ethyl]-carbamic acid tert-butyl ester

The desired product was obtained as an orange oil following the synthetic procedure described for Allyl-[2-(4-amino-phenyl)-ethyl]-carbamic acid tert-butyl ester starting from [2-(3-Amino-phenyl)-ethyl]-carbamicacid tert-butyl ester and allylbromide.

d. Preparation of 2-(4-Aminobenzyl)-1-propylpyrrolidine d. 1.1: 2-(4-Nitrobenzyl)-1-propylpyrrolidine

2-Benzyl-1-propylpyrrolidine (0.90 g, 3.75 mmol) was dissolved in nitromethane (10 mL) and added to a mixture of concentrated H$_2$SO$_4$ (3.7 mL), concentrated nitric acid (0.3 mL) and water (0.6 mL) cooled to 5° C. After stirring for 2 h, the reaction solution was poured into water, extracted with ethyl acetate and the organic phase separated and dried over MgSO$_4$. The filtered solution was concentrated to give a brown oil (0.95 g, 100%).

MS (ESI) m/z: 249.3 [M+H]$^+$ d.1.2: 2-(4-Aminobenzyl)-1-propylpyrrolidine

The mixture of nitro compounds from d.1.1 (0.94 g, 3.79 mmol) was dissolved in methanol (60 mL) and tin chloride (4.30 g, 19.1 mmol) added. The solution was heated to reflux for 3 h, the solution was concentrated and the residue partitioned between ethyl acetate and NaOH (2M), and the organic phase separated and dried over MgSO$_4$. The filtered solution was concentrated and the residue separated by preparative HPLC (10-90% methanol) to give the 2 amino isomers. The p-amino product was obtained as a yellow oil (0.30 g, 37%). The m-amino product was obtained as a yellow oil (38 mg, 5%).

MS (ESI) m/z: 219.4 [M+H]$^+$ $^1$H-NMR (DMSO-d$_6$): δ [ppm] 6.85 (d, 2H), 6.43 (d, 1H), 3.08 (m, 1H), 2.75 (m, 1H), 2.45 (m, 1H), 2.18 (m, 3H), 1.62-1.35 (m, 6H), 0.82 (t, 3H).

$^{13}$C-NMR (DMSO-d$_6$): δ [ppm] 146.5 (s), 129.4 (d), 126.5 (s), 113.8 (d), 66.2 (d), 55.8 (t), 53.3 (t), 29.7 (t), 21.6 (t), 11.9 (q).

e. Preparation of sulfonyl chlorides e. 1 4-((S)-2-Fluoro-1-methyl-ethyl)-benzenesulfonyl chloride e.1.1 Toluene-4-sulfonic acid (S)-2-phenyl-propyl ester

To a solution of 20 g of (S)-(−)-2-phenyl-1-propanol in 240 ml of dichloromethane was added in portions 28 g of p-toluenesulfonyl chloride (146.8 mmol). After stirring for 18 h at room temperature, the organic phase was washed with 100 ml of water, dried over magnesium sulfate, filtered, and the solvent evaporated under reduced pressure to yield 43 g of the title compound.
$^1$H-NMR (CDCl$_3$, 400 MHz): δ [ppm] 7.65 (d, 2H), 7.15-7.3 (m, 5H), 7.1 (d, 2H), 4.0-4.1 (m, 2H), 3.1 (m, 1H), 2.4 (s, 3H), 1.3 (d, 3H).

e.1.2 ((S)-2-Fluoro-1-methyl-ethyl)-benzene 9.62 g of toluene-4-sulfonic acid (S)-2-phenyl-propyl ester (33.13 mmol) were dissolved in 80 ml of polyethylenglycol 400. 9.62 g of potassium fluoride (165.6 mmol) were added and the reaction mixture was stirred at 50° C. for 3 days and another 2 days at 55-70° C. The reaction was treated with 150 ml of saturated aqueous sodium chloride solution, extracted three times with diethyl ether, and the combined organic layers were dried over magnesium sulfate, filtered, and the solvent was evaporated under reduced pressure. The crude product was purified via silica gel chromatography using cyclohexyane/ethyl acetate 15% as eluent. 2.85 g of the desired product were isolated, containing ~25% of the elimination side product.
$^1$H-NMR (CDCl$_3$, 400 MHz): δ [ppm] 7.2-7.4 (m, 5H), 4.3-4.6 (several m, 2H), 3.15 (m, 1H) 1.3 (m, 3H).

e.1.3 4-((S)-2-Fluoro-1-methyl-ethyl)-benzenesulfonyl chloride 3.5 g of ((S)-2-fluoro-1-methyl-ethyl)-benzene (25.32 mmol) were dissolved in 80 ml of dichloromethane. At 0-5° C., 11.81 g of chlorosulfonic acid (101.31 mmol), dissolved in 20 ml of dichloromethane, were added dropwise. The reaction mixture was stirred for 30 min at room temperature and 2 h at 30° C. The solvent was evaporated. 150 ml of diethyl ether were added to the residue, washed once with 150 ml of water, and the organic layer was dried over magnesium sulfate, filtered, and the solvent evaporated under reduced pressure. The crude product was purified via silica gel chromatography with n-heptane-dichloromethane (6:4) as eluent to give 1.5 g of the title compound.
$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

e.2 4-((R)-2-Fluoro-1-methyl-ethyl)-benzenesulfonyl chloride e.2.1 Toluene-4-sulfonic acid (R)-2-phenyl-propyl ester

Following the procedure analogous to that used for the synthesis of toluene-4-sulfonic acid (S)-2-phenyl-propyl ester, but using (R)-2-phenyl-1-propanol, the title compound was prepared.

e.2.2 ((R)-2-Fluoro-1-methyl-ethyl)-benzene

The title compound was prepared as described above for the synthesis of ((S)-2-fluoro-1-methyl-ethyl)-benzene, but using toluene-4-sulfonic acid (R)-2-phenyl-propyl ester instead of toluene-4-sulfonic acid (S)-2-phenyl-propyl ester.
$^1$H-NMR (CDCl$_3$, 400 MHz): δ [ppm] 7.2-7.4 (m, 5H), 4.3-4.6 (several m, 2H), 3.15 (m, 1H). 1.3 (m, 3H).

e.2.3 4-((R)-2-Fluoro-1-methyl-ethyl)-benzenesulfonyl chloride 1.3 g of ((R)-2-fluoro-1-methyl-ethyl)-benzene (9.4 mmol) were dissolved in 50 ml of dichloromethane. At 0-5° C., 1.1 g of chlorosulfonic acid (9.4 mmol), dissolved in 10 ml of dichloromethane, were added dropwise. The reaction mixture was stirred for 20 min at 0-5° C. and then added to a solution of 2.15 g of phosphorous pentachloride dissolved in 40 ml of dichloromethane. The reaction mixture was stirred for 30 min at 0-5° C. and 1 h at room temperature. The solvent was evaporated, 100 ml of diethyl ether were added, the mixture was washed once with 150 ml of water, and the organic layer dried over magnesium sulfate, filtered, and the solvent evaporated under reduced pressure. The crude product was purified via silica gel chromatography with n-heptane-dichloromethane (1:1) as eluent to give 0.261 g of the title compound.
$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

e.3 4-(2-Fluoro-1-methyl-ethyl)-benzenesulfonyl chloride

Following the procedures analogous to that used for the preparation of 4-((S)-2-fluoro-1-methyl-ethyl)-benzenesulfonyl chloride, but starting with 2-phenyl-1-propanol in step a.3.1, the title compound was prepared.
$^1$H-NMR (CDCl$_3$, 400 MHz): δ [ppm] 8.0 (d, 2H), 7.5 (d, 2H), 4.5 (dd, 2H), 3.25 (m, 1H), 1.4 (d, 3H).

e.4 4-(2-Fluoro-1-fluoromethyl-ethyl)-benzenesulfonyl chloride e.4.1 (2-Fluoro-1-fluoromethyl-ethyl)-benzene 4 g of 3-phenylglutaric acid (19.21 mmol) were suspended in 350 ml of dichloromethane. At room temperature, 6.5 g of xenon difluoride (38.42 mmol) were added and the reaction mixture was stirred at room temperature for 18 h. The organic phase was washed once with 975 ml of 6% aqueous sodium hydrogencarbonate, dried over magnesium sulfate, filtered, and the solvent evaporated. The remaining residue was distilled at a bath temperature of 123° C. at 21 mm to yield 0.78 g of the title compound that contained ~50% of 4-(2-Fluoro-1-methyl-ethyl)-benzene.
$^1$H-NMR (CDCl$_3$, 400 MHz): δ [ppm] 7.2-7.4 (m, 5H), 4.6-4.8 (dd, 4H), 3.3 (m, 1H).

e.4.2 4-(2-Fluoro-1-fluoromethyl-ethyl)-benzenesulfonyl chloride

Following the procedures analogous to that used for the preparation of 4-((S)-2-fluoro-1-methyl-ethyl)-benzenesulfonyl chloride, but using 5 equivalents of chlorosulfonic acid, 0.12 g of the title compound were obtained.
$^1$H-NMR (CDCl$_3$, 400 MHz): δ [ppm] 8.05 (d, 2H), 7.55 (d, 2H), 4.75 (dd, 4H), 3.4 (m, 1H).

e.5 4-(3,3,3-Trifluoropropyl)-benzenesulfonyl chloride 2.9 g were obtained from commercially available (3,3,3-trifluoropropyl)-benzene following the procedure used for the synthesis of 4-((S)-2-fluoro-1-methyl-ethyl)-benzenesulfonyl chloride described above.
$^1$H-NMR (CDCl$_3$, 400 MHz): δ [ppm] 8.0 (d, 2H), 7.45 (d, 2H), 3.0 (t, 2H), 2.45 (m, 2H).

e.6 4-(2,2,2-Trifluoroethyl)-benzenesulfonyl chloride

The product was obtained from commercially available (2,2,2-trifluoroethyl)-benzene following the procedure as described in J. Org. Chem., 1960, 25, 1824-26.

$^1$H-NMR (CDCl$_3$, 400 MHz): δ [ppm] 8.05 (d, 2H), 7.55 (d, 2H), 3.5 (q, 2H).

e.7 4-(3-Fluoropropyl)-benzenesulfonyl chloride e.7.1 (3-Fluoropropyl)-benzene 15.6 g of diethylaminosulfurtrifluoride (DAST, 96.91 mmol) were dissolved in 18 ml of dichloromethane. At 0-5° C., 12 g of 3-phenyl-1-propanol (88.1 mmol) dissolved in 30 ml of dichloromethane, were added dropwise. The reaction mixture was stirred for 18 h, and, after addition of 30 ml of dichloromethane, poured onto 100 ml of ice water. The organic layer was separated, dried over magnesium sulfate, filtered, and the solvent evaporated. The crude product was purified by distillation at a bath temperature of 106° C. at 20 mm to yield 7.4 g of the title compound.

$^1$H-NMR (CDCl$_3$, 400 MHz): δ [ppm] 7.1-7.3 (m, 5H), 4.4 (dt, 2H), 2.7 (m, 2H). 2.0 (m, 2H).

e.7.2 4-(3-Fluoropropyl)-benzenesulfonyl chloride 4.1 g of (3-fluoro-propyl)-benzene (29.67 mmol) were dissolved in 40 ml of dichloromethane. At 0-5° C., 6.91 g of chlorosulfonic acid (59.34 mmol), dissolved in 10 ml of dichloromethane, were added dropwise. The reaction mixture was stirred for 45 min at 0-5° C. and then added to a solution of 6.8 g of phosphorous pentachloride (32.63 mmol) dissolved in 50 ml of dichloromethane. The reaction mixture was stirred for 1 h at 5-10° C. The solvent was evaporated, 150 ml of diethyl ether added, washed once with 150 ml of ice water, and the organic layer dried over magnesium sulfate, filtered, and the solvent evaporated under reduced pressure. The crude product was purified via silica gel chromatography with n-heptane-dichloromethane (11:9) as eluent to give 5.5 g of the title compound.

$^1$H-NMR (CDCl$_3$, 400 MHz): δ [ppm] 7.95 (d, 2H), 7.45 (d, 2H), 4.5 (dt, 2H), 2.9 (t, 2H), 2.05 (m, 2H).

e.8 4-(2,2-Difluoro-cyclopropyl)-benzenesulfonyl chloride 2.07 g of were obtained from commercially available (2,2-difluorocyclopropyl)-benzene following the procedure used for the synthesis of (3-fluoropropyl)-benzenesulfonyl chloride with the exception that only 1.1 equivalents of phosphorous pentachloride were used.

$^1$H-NMR (CDCl$_3$, 400 MHz): δ [ppm] 8.0 (d, 2H), 7.45 (d, 2H), 2.85 (m, 1H), 2.0 (m, 1H), 1.75 (m, 1H).

e.9 3-Bromo-4-trifluoromethoxy-benzenesulfonyl chloride 2.0 g of 1-bromo-2-(trifluoro-methoxy)benzene (8.3 mmol) were dissolved in 30 ml of dichloromethane. At 0-5° C., 1.06 g of chlorosulfonic acid (9.13 mmol), dissolved in 3 ml of dichloromethane, were added dropwise. The reaction mixture was stirred for 30 min at room temperature. Additional 5.5 equivalents of chlorosulfonic in dichloromethane were added to drive the reaction to completion. Standard work-up was followed and silica gel chromatography with n-heptane-dichloromethane (6:4) as eluent gave 2.19 g of the title compound.

$^1$H-NMR (CDCl$_3$, 400 MHz): δ [ppm] 8.3 (d, 1H), 8.05 (dd, 1H), 7.5 (dd, 1H).

e.10 4-(2-Fluoroethyl)-benzenesulfonyl chloride e.10.1 (2-Fluoroethyl)-benzene 6.8 g of the title compound were obtained from commercially available 2-phenyl-ethanol following the procedure used for the synthesis of (3-fluoropropyl)-benzene.

$^1$H-NMR (CDCl$_3$, 400 MHz): δ [ppm] 7.1-7.3 (m, 5H), 4.6 (m, 1H), 4.45 (m, 1H), 2.95 (m, 1H), 2.9 (m, 1H).

e. 10.2 4-(2-Fluoroethyl)-benzenesulfonyl chloride 3.55 g were obtained following the procedure used for the synthesis of 4-((R)-2-fluoro-1-methyl-ethyl)-benzenesulfonyl chloride.

$^1$H-NMR (CDCl$_3$, 400 MHz): δ [ppm] 8.0 (d, 2H), 7.5 (d, 2H), 4.7 (dt, 2H), 3.05-3.2 (dt, 2H).

e.11 5-Propylthiophene-2-sulfonyl chloride

Following the procedures analogous to that used for the preparation of (3-fluoro-propyl)-benzenesulfonyl chloride, but using only 1 equivalent of phosphorous pentachloride, the title compound was prepared.

$^1$H-NMR (CDCl$_3$, 400 MHz): δ [ppm] 7.7 (d, 1H), 6.85 (d, 1H), 2.9 (t, 2H), 1.75 (m, 2H), 1.0 (t, 3H).

e.12 4-(1-Methyl-1H-pyrazol-4-yl)-benzenesulfonyl chloride e.12.1 1-Methyl-4-phenyl-1H-pyrazole 1 g of 2-phenylmalonaldehyde (6.75 mmol) were dissolved in 25 ml of ethanol. 0.36 ml of N-methyl-hydrazine (6.75 mmol) were added, the reaction mixture was stirred under reflux for 4 h, the solvent evaporated under reduced pressure to yield 1.09 g of the product.

ESI-MS: 159.1 [M+H]+

$^1$H-NMR (CDCl$_3$, 400 MHz): δ [ppm] 7.75 (s, 1H), 7.6 (s, 1H), 7.45 (d, 2H), 7.35 (t, 2H), 7.2 (t, 1H), 3.9 (s, 3H)

e. 12.2 4-(1-Methyl-1H-pyrazol-4-yl)-benzenesulfonyl chloride 0.5 g of 1-methyl-4-phenyl-1H-pyrazole (3.16 mmol) were dissolved in 20 ml of dichloromethane. At 0° C., 0.232 ml of chlorosulfonic acid were added and the reaction mixture was stirred for 1 h under ice cooling. Additional 0.7 ml of chlorosulfonic acid were added, the mixture was stirred at 0° C. for 30 minutes and then 90 minutes at 50° C. The two phases were separated and the lower layer put on ice, extracted twice with diethyl ether, dried over magnesium sulfate, filtered, and the solvent evaporated under reduced pressure to yield 0.496 g of the product.

$^1$H-NMR (CDCl$_3$, 400 MHz): δ [ppm] 8.0 (d, 2H), 7.85 (s, 1H), 7.75 (s, 1H), 7.65 (d, 2H), 4.0 (s, 3H).

e.13 4-(1,1,1-Trifluoropropan-2-yl)benzenesulfonyl chloride and 2-(1,1,1-trifluoropropan-2-yl)benzenesulfonyl chloride Prepared on a 14 g scale following the procedure outlined in Scheme 7. 2-(1,1,1-Trifluoropropan-2-yl)benzenesulfonyl chloride is a by-product of the reaction.

4-(1,1,1-Trifluoropropan-2-yl)benzenesulfonyl chloride:
MS (ESI) m/z: 273.1 [M+H]$^+$
$^1$H-NMR (DMSO-d$_6$): δ [ppm] 7.62 (d, 2H), 7.33 (d, 2H), 3.81 (m, 1H), 1.42 (d, 3H).
2-(1,1,1-Trifluoropropan-2-yl)benzenesulfonyl chloride:
MS (ESI) m/z: 273.1 [M+H]$^+$ e. 14 4-(1,1-Difluoropropan-2-yl)benzenesulfonyl chloride and 2-(1,1-Difluoropropan-2-yl)benzene-1-sulfonyl chloride Prepared on an 11 g scale following the procedure outlined in Scheme 6. 2-(1,1-Difluoropropan-2-yl)benzene-1-sulfonyl chloride is a by-product of the reaction.

4-(1,1-Difluoropropan-2-yl)benzenesulfonyl chloride:
MS (ESI) m/z: 255.0 [M+H]$^+$
$^1$H-NMR (DMSO-d$_6$): δ [ppm] 8.03 (d, 2H), 7.55 (d, 2H), 5.88 (dt, 1H), 3.34 (m, 1H), 1.47 (d, 3H).
$^{13}$C-NMR (DMSO-d$_6$): δ [ppm] 146.43, 143.54, 129.77, 127.28, 117.06 (t), 43.76, 13.78.
2-(1,1-difluoropropan-2-yl)benzene-1-sulfonyl chloride:
Isolated by chromatography on 110 mg scale.
MS (ESI) m/z: 255.0 [M+H]$^+$
$^1$H-NMR (DMSO-d$_6$): δ [ppm] 8.15 (d, 1H), 7.77 (t, 1H), 7.70 (d, 1H), 7.54 (t, 1H), 5.99 (dt, 1H), 4.43 (m, 1H), 1.51 (d, 3H).
$^{13}$C-NMR (DMSO-d$_6$): δ [ppm] 143.45, 138.63, 135.53, 130.93, 129.04, 128.17, 116.61 (t), 38.38, 13.68.

II. Preparation of Compounds I

Example 1

N-[4-((S)-2-Propylamino-propyl)-phenyl]-4-trifluoromethoxy-benzenesulfonamide

1.1 N—[(S)-2-(4-Amino-phenyl)-1-methyl-ethyl]-propionamide

To a solution of 4-((S)-2-amino-propyl)-phenylamine×HCl (1.24 g, 6.66 mmol) and triethylamine (1.4 g, 13.83 mmol) in dichloromethane (20 ml) propionyl chloride (620 mg, 6.66 mmol) was added at −5-0° C. The mixture was stirred at room temperature for 4 h. The mixture was partitioned between water and dichloromethane and to the organic layer was added HCl (1M). At pH=8 the aqueous layer was extracted three times with ethyl acetate. The combined organic layers were washed with water, dried over MgSO$_4$ and the solvent evaporated under reduced pressure to give the product as an orange oil (300 mg, 22%).

1.2 N—{(S)-1-Methyl-2-[4-(4-trifluoromethoxy-benzenesulfonylamino)-phenyl]-ethyl}-propionamide To a solution of N—[(S)-2-(4-amino-phenyl)-1-methyl-ethyl]-propionamide (300 mg, 1.45 mmol) and triethylamine (300 mg, 2.96 mmol) in tetrahydrofuran (THF) (30 ml) 4-trifluoromethoxy-benzenesulfonyl chloride (380 mg, 1.45 mmol) was added at −5-0° C. The mixture was stirred at room temperature for 2 h. The mixture was partitioned between water and ethyl acetate. The organic layer was washed with 5% citric acid, saturated aqueous NaHCO$_3$, water, and brine, dried over MgSO$_4$ and the solvent evaporated under reduced pressure to give the product as a brown oil (500 mg, 80%).

1.3 N-[4-((S)-2-Propylamino-propyl)-phenyl]-4-trifluoromethoxy-benzenesulfonamide To a solution of N-{(S)-1-methyl-2-[4-(4-trifluoromethoxy-benzenesulfonylamino)-phenyl]-ethyl}-propionamide (500 mg, 1.16 mmol) in THF (20 ml) borane-dimethylsulfid complex (2M in THF, 2.63 mmol) was added at room temperature. The mixture was heated to reflux for 2 h. The mixture was allowed to come to room temperature and HCl (2M) was added. This mixture was stirred for 16 h at room temperature. After extracting the mixture three times with dichloromethane the combined organic layers were washed with saturated aqueous NaHCO$_3$, water, and brine, dried over MgSO$_4$ and the solvent evaporated under reduced pressure to give the product as a yellow oil. Column chromatography (CH$_2$Cl$_2$, 2%/methanol, 5%, 10%) gave the product as a yellow oil (300 mg, 62%).

MS (ESI) m/z: 417.15 [M+H]$^+$
$^1$H-NMR (CDCl$_3$): δ [ppm] 7.80 (d, 2H), 7.20 (d, 2H), 7.06 (d, 2H), 7.00 (d, 2H), 2.90-3.00 (m, 1H), 2.80-2.90 (m, 1H), 2.65-2.75 (m, 1H), 2.52-2.60 (m, 2H), 1.45-1.60 (m, 2H), 1.05-1.10 (m, 3H), 0.85 (t, 3H).

Example 2

N-[4-((R)-2-Propylamino-propyl)-phenyl]-4-trifluoromethoxy-benzenesulfonamide The desired product was obtained as a yellow powder following the same synthetic procedure as described for N-[4-((S)-2-propylamino-propyl)-phenyl]-4-trifluoromethoxy-benzenesulfonamide starting from 4-((R)-2-amino-propyl)-phenylamine×HCl.

MS (ESI) m/z: 417.15 [M+H]$^+$
$^1$H-NMR (CDCl$_3$): δ [ppm] 7.80 (d, 2H), 7.20 (d, 2H), 7.06 (d, 2H), 7.00 (d, 2H), 2.90-3.00 (m, 1H), 2.80-2.90 (m, 1H), 2.65-2.75 (m, 1H), 2.52-2.60 (m, 2H), 1.45-1.60 (m, 2H), 1.05-1.10 (m, 3H), 0.85 (t, 3H).

Example 3

4-Isopropyl-N-[4-(2-propylamino-propyl)-phenyl]-benzenesulfonamide×HCl

Starting from racemic 4-(2-amino-propyl)-phenylamine and propionyl chloride the desired product was obtained as a yellow powder following the synthetic protocol of example 1 using 4-Isopropyl-benzenesulfonyl chloride.

MS (ESI) m/z: 375.25 [M+H]$^+$
$^1$H-NMR (CDCl$_3$): δ [ppm] 7.69 (d, 2H), 7.25 (d, 2H), 7.06 (d, 2H), 7.00 (d, 2H), 2.88-2.98 (m, 1H), 2.78-2.87 (m, 1H), 2.42-2.70 (several m, 4H), 1.36-1.49 (m, 2H), 1.19-1.22 (m, 6H), 0.99-1.01 (m, 3H), 0.82 (t, 3H).

Example 4

N-[4-(2-Methyl-2-propylamino-propyl)-phenyl]-4-trifluoromethoxy-benzenesulfonamide

4.1 N-[2-(4-Amino-phenyl)-1,1-dimethyl-ethyl]-propionamide

A mixture of N-[1,1-dimethyl-2-(4-nitro-phenyl)-ethyl]-propionamide (1 g, 4 mmol) and 10% palladium on charcoal (100 mg) in methanol (50 ml) was hydrogenated at atmospheric pressure. After filtration the solvent was evaporated and the residue dissolved in ethyl acetate. The solution was dried over MgSO$_4$, filtered, and the solvent evaporated under reduced pressure to give the product as a yellow oil (800 mg, 91%).

4.2 N-{1,1-Dimethyl-2-[4-(4-trifluoromethoxy-benzenesulfonylamino)-phenyl]-ethyl}-propionamide To a solution of N-[2-(4-amino-phenyl)-1,1-dimethyl-ethyl]-propionamide (800 mg, 3.63 mmol) and triethylamine (800 mg, 7.91 mmol) in THF (30 ml) 4-Trifluoromethoxy-benzenesulfonyl chloride (950 mg, 3.63 mmol) was added at −5-0° C. The mixture was stirred at room temperature for 2 h. The mixture was partitioned between water and ethyl acetate. The organic layer was washed with 5% citric acid, saturated aqueous NaHCO$_3$, water, and brine, dried over MgSO$_4$ and the solvent evaporated under reduced pressure. The residue was triturated with diethylether and the precipitate filtered and dried in vacuo to give the product as a brown powder (700 mg, 43%).

MS (ESI) m/z: 445.35 [M+H]$^+$

4.3 N-[4-(2-Methyl-2-propylamino-propyl)-phenyl]-4-trifluoromethoxy-benzene-sulfonamide To a solution of N-{1,1-dimethyl-2-[4-(4-trifluoromethoxy-benzenesulfonylamino)-phenyl]-ethyl}-propionamide (700 mg, 1.57 mmol) in THF (20 ml) borane-dimethylsulfid complex (2M in THF, 6.32 mmol) was added at room temperature. The mixture was heated to reflux for 2 h. The mixture was allowed to come to room temperature and HCl (2M) was added. This mixture was stirred for 16 h at room temperature. After extracting the mixture three times with dichloromethane the combined organic layers were washed with saturated aqueous NaHCO$_3$, water, brine, dried over MgSO$_4$, filtered, and the solvent evaporated under reduced pressure to give the product as a yellow oil. Column chromatography (CH$_2$Cl$_2$, 2%/methanol, 5%, 10%) gave the product as a yellow foam (500 mg, 74%).

MS (ESI) m/z: 431.35 [M+H]$^+$ $^1$H-NMR (CDCl$_3$): δ [ppm] 7.82 (d, 2H), 7.21 (d, 2H), 7.03 (d, 2H), 6.99 (d, 2H), 2.78 (s, 2H), 2.64-2.70 (m, 2H), 1.55-1.65 (m, 2H), 1.08 (s, 6H), 0.91 (t, 3H).

Example 5

N-[4-((1-Propylamino-cyclopropyl)methyl)-phenyl]-4-trifluoromethoxy-benzenesulfonamide Starting from N-[1-(4-nitro-benzyl)-cyclopropyl]-propionamide the desired product was obtained as a yellow oil following the synthetic protocol of example 4.

MS (ESI) m/z: 429.15 [M+H]$^+$ $^1$H-NMR (CDCl$_3$): δ [ppm] 7.81 (d, 2H), 7.24 (d, 2H), 7.12 (d, 2H), 7.02 (d, 2H), 2.70 (s, 2H), 2.58-2.63 (m, 2H), 1.30-1.40 (m, 2H), 0.81 (t, 3H), 0.64 (m, 2H), 0.50 (m, 2H).

Example 6

4-Isopropyl-N-[4-(2-propylamino-ethyl)-phenyl]-benzenesulfonamide×HCl

Starting from commercially available 2-(4-aminophenyl) ethylamine and propionyl chloride the desired product was obtained as a colorless powder following the synthetic protocol of example 1 using 4-isopropyl-benzenesulfonyl chloride.

MS (ESI) m/z: 361.15 [M+H]$^+$ $^1$H-NMR (DMSO-d$_6$): δ [ppm] 10.25 (s, 1H); 8.93 (bs, 2H), 7.7 (d, 2H), 7.41 (d, 2H), 7.04-7.15 (m, 4H), 3.47-3.65 (m, 2H), 2.77-3.10 (m, 5H), 1.58-1.69 (m, 2H), 1.18 (d, 6H), 0.90 (t, 3H).

Example 7

N-{4-[2-(Cyclopropylmethyl-amino)-ethyl]-phenyl}-4-isopropyl-benzenesulfonamide×HCl Starting from commercially available 2-(4-aminophenyl) ethylamine and cyclopropanecarbonyl chloride the desired product was obtained as a colorless powder following the synthetic protocol of example 1 using 4-isopropyl-benzenesulfonyl chloride.

MS (ESI) m/z: 373.15 [M+H]$^+$ $^1$H-NMR (DMSO-d$_6$): δ [ppm] 10.28 (s, 1H); 9.02 (bs, 2H), 7.70 (d, 2H), 7.41 (d, 2H), 7.04-7.15 (m, 4H), 2.75-3.10 (several m, 7H), 1.15-1.22 (m, 2H), 1.01-1.12 (m, 1H), 0.52-0.61 (m, 2H), 0.30-0.41 (m, 2H).

Example 8

N-[4-(2-Dipropylamino-ethyl)-phenyl]-4-isopropyl-benzenesulfonamide×HCl

8.1 {2-[4-(4-Isopropyl-benzenesulfonylamino)-phenyl]-ethyl}-carbamic acid tert-butyl ester To a solution of [2-(4-amino-phenyl)-ethyl]-carbamic acid tert-butyl ester (10.75 g, 45.49 mmol) in pyridine (125 ml) at 0° C. 4-isopropyl-benzenesulfonyl chloride (10.45 g, 47.76 mmol) was added. The mixture was stirred at 0° C. for 1 h and 16 h at room temperature. After concentration in vacuo the residue was partitioned between dichloromethane and saturated aqueous NaHCO$_3$. The organic layer was washed with water, dried over MgSO$_4$, filtered and the solvent evaporated under reduced pressure to give the product as a brown oil (20.82 g, 50%).

8.2 N-[4-(2-Amino-ethyl)-phenyl]-4-isopropyl-benzenesulfonamide×HCl

To a solution of {2-[4-(4-isopropyl-benzenesulfonylamino)-phenyl]-ethyl}-carbamic acid tert-butyl ester (20.42 g, 48.79 mmol) in diethylether (200 ml) and THF (80 ml) at 0° C. HCl in diethylether (100 ml) was added slowly. The mixture was stirred at room temperature for 16 h. After concentration in vacuo the product was obtained as a yellow foam (17.3 g, 99.9%).

8.3 N-[4-(2-Dipropylamino-ethyl)-phenyl]-4-isopropyl-benzenesulfonamide×HCl

A solution of N-[4-(2-amino-ethyl)-phenyl]-4-isopropyl-benzenesulfonamide×HCl (740 mg, 2.09 mmol), 4 Å molecular sieves (750 mg) and cesium hydroxide (1.09 g, 6.27 mmol) in DMF was stirred at room temperature for 1 h before 1-bromo-propane (516 mg, 4.2 mmol) was added. The mixture was stirred at room temperature for 16 h. After concentrating the mixture in vacuo the residue was purified by column chromatography (toluene/THF/methanol, 4/1/1+2.5% triethylamine). The obtained yellow oil was dissolved in diethylether, and HCl in diethylether (1M) was added. The precipitate was collected and dried in vacuo to give the product as a colorless powder (210 mg, 23%).

MS (ESI) m/z: 403.25 [M+H]$^+$
$^1$H-NMR (DMSO-d$_6$): δ [ppm] 10.30 (s, 1H), 7.69 (d, 2H), 7.4 (d, 2H), 7.17 (d, 2H), 7.06 (d, 2H), 3.12-3.22 (m, 2H), 2.87-3.08 (m, 7H), 1.61-1.75 (m, 4H), 1.19 (d, 6H), 0.88 (t, 6H).

Example 9

N-[4-(2-Dipropylamino-ethyl)-phenyl]-4-isopropyl-N-methyl-benzenesulfonamide×HCl To a solution of N-[4-(2-dipropylamino-ethyl)-phenyl]-4-isopropyl-benzenesulfonamide×HCl (80 mg, 0.17 mmol) in N,N-dimethylformamide (DMF) (2.5 ml) 15-crown 5, and sodium hydride (10 mg, 0.36 mmol) were added, and the mixture was stirred at room temperature for 30 min. At 0° C. methyliodide (10 ml, 0.17 mmol) was added and the mixture was kept at 0° C. for 1 h. Then it was stirred for 16 h at room temperature. After concentration in vacuo the residue was partitioned between ethyl acetate and saturated aqueous NaHCO$_3$. The organic layer was washed with water, dried over MgSO$_4$, filtered and the solvent evaporated under reduced pressure. The residue was dissolved in THF/diethyl ether and HCl in diethyl ether (1M) was added. The precipitate was collected and dried in vacuo to give the product as a yellow powder (50 mg, 59%).

MS (ESI) m/z: 417.25 [M+H]$^+$
$^1$H-NMR (DMSO-d$_6$): δ [ppm] 9.76 (bs, 1H), 7.45 (s, 4H), 7.29 (d, 2H), 7.09 (d, 2H), 3.21-3.4 (m, 2H), 2.95-3.15 (m, 10H), 1.60-1.76 (m, 4H), 1.23 (d, 6H), 0.90 (t, 6H).

Example 10

4-Isopropyl-N-[6-(2-propylamino-ethyl)-pyridin-3-yl]-benzenesulfonamide×2HCl

10.1 (5-Nitro-pyridin-2-yl)-acetonitrile

To a solution of 5-nitro-2-chloropyridine (18 g, 113.5 mmol) in THF (100 ml) at room temperature K$_2$CO$_3$ (39.2 g, 283.8 mmol), cyanoacetic acid tert-butyl ester (24 g, 170.30 mmol) and 4 Å molecular sieves were added. The mixture was heated to reflux and stirred for 20 h. After concentrating the mixture under reduced pressure the residue was partitioned between ethyl acetate and saturated aqueous NaHCO$_3$. The organic layer was washed with brine, dried over MgSO$_4$, filtered and the solvent evaporated under reduced pressure. The obtained oil was dissolved in toluene (300 ml), toluene-4-sulfonic acid (2 g, 11.6 mmol) was added, and the mixture was heated to reflux for 2 h. The mixture then was stirred at room temperature for 16 h. After which the mixture was concentrated under reduced pressure. The residue was partitioned between ethyl acetate and water. The aqueous layer was extracted with ethyl acetate and the combined organic layers were washed with brine, dried over MgSO$_4$, filtered, and the solvent evaporated under reduced pressure. Column chromatography (cyclohexane/dichloromethane, 4/1) gave the product as a colorless oil (10.3 g, 66%).

10.2 (5-Amino-pyridin-2-yl)-acetonitrile

To a mixture of (5-nitro-pyridin-2-yl)-acetonitrile (500 mg, 3.06 mmol) in concentrated aqueous HCl (3.1 ml) and ethanol (3.1 ml) at 0° C. SnCl$_2$ (2.3 g, 10.11 mmol) was added. The mixture was allowed to come to room temperature and was stirred for 2 h. The mixture was partitioned between ethyl acetate and saturated aqueous NaHCO$_3$. The aqueous layer was extracted three times with ethyl acetate and the combined organic layers were washed with brine, dried over MgSO$_4$, filtered, and the solvent evaporated under reduced pressure to give the product as a brown oil (300 mg, 74%).

MS (ESI) m/z: 134.05 [M+H]$^+$

10.3 N-(6-Cyanomethyl-pyridin-3-yl)-4-isopropyl-benzenesulfonamide

To a solution of (5-amino-pyridin-2-yl)-acetonitrile (1 g, 7.5 mmol) in pyridine (10 ml) 4-Isopropyl-benzenesulfonyl chloride (1.64 g, 7.5 mmol) was added at −5-0° C. The mixture was stirred at 0° C. for 2 h and at room temperature for 16 h. The mixture was concentrated under reduced pressure, and the residue partitioned between ethyl acetate and saturated aqueous NaHCO$_3$. The aqueous layer was extracted three times with ethyl acetate and the combined organic layers were washed with water, and brine, dried over MgSO$_4$, filtered, and the solvent evaporated under reduced pressure to give the product as a brown oil which was purified by column chromatography using methyl-tert-butylether as an eluent to give a colorless oil (1.7 g, 72%).

MS (ESI) m/z: 316.10 [M+H]$^+$

10.4 N-[6-(2-Amino-ethyl)-pyridin-3-yl]-4-isopropyl-benzenesulfonamide

A mixture of N-(6-cyanomethyl-pyridin-3-yl)-4-isopropyl-benzenesulfonamide (1.7 g, 5.4 mmol) aqueous ammonia (45 ml) and raney-nickel (2.7 mmol) in ethanol (50 ml) was hydrogenated at atmospheric pressure. After filtration the mixture was concentrated under reduced pressure. The residue was partitioned between ethyl acetate and saturated aqueous NaHCO$_3$ and the aqueous layer extracted five times with ethyl acetate. The combined organic layers were dried over MgSO$_4$, filtered, and the solvent evaporated under reduced pressure to give the product as a yellow powder after recrystallisation from methanol/ethyl acetate (1.3 g, 73%).

MS (ESI) m/z: 320.00 [M+H]$^+$

10.5 N-{2-[5-(4-Isopropyl-benzenesulfonylamino)-pyridin-2-yl]-ethyl}-propionamide To a solution of N-[6-(2-Amino-ethyl)-pyridin-3-yl]-4-isopropyl-benzenesulfonamide (50 mg, 0.16 mmol) in pyridine (3 ml) propionyl chloride (10 mg, 0.16 mmol) was added at −5-0° C. The mixture was stirred at 0° C. for 2 h and 3 h at room temperature. The mixture was partitioned between water and ethyl acetate and HCl (1M) was added. At pH=8 the aqueous layer was extracted three times with ethyl acetate. The combined organic layers were washed with water, dried over MgSO₄, filtered, and the solvent evaporated under reduced pressure to give the product as a yellow oil (40 mg, 68%).

MS (ESI) m/z: 376.15 [M+H]⁺

10.6 4-Isopropyl-N-[6-(2-propylamino-ethyl)-pyridin-3-yl]-benzenesulfonamide×2HCl To a solution of N-{2-[5-(4-Isopropyl-benzenesulfonylamino)-pyridin-2-yl]-ethyl}-propionamide (40 mg, 0.11 mmol) in THF (3 ml) borane-dimethylsulfid complex (2M in THF, 1.49 mmol) was added at room temperature. The mixture was heated to reflux for 2 h. The mixture was allowed to come to room temperature and HCl (2M) was added. This mixture was stirred for 16 h at room temperature. After extracting the mixture three times with dichloromethane the combined organic layers were washed with saturated aqueous NaHCO₃, water, and brine, dried over MgSO₄ and the solvent evaporated under reduced pressure to give the product as a yellow oil which was dissolved in diethylether, and HCl in diethylether (1M) was added. The precipitate was collected and dried in vacuo to give the product as a colorless powder (6 mg, 15%).

MS (ESI) m/z: 362.15 [M+H]⁺
¹H-NMR (MeOD): δ [ppm] 8.39 (s, 1H), 7.98 (bs, 1H), 7.62-7.80 (m, 3H), 7.35 (d, 2H), 3.18-3.40 (m, 4H), 2.82-3.00 (m, 3H), 1.58-1.75 (m, 2H), 1.28 (d, 6H), 0.95 (t, 3H).

Example 11

4-Isopropyl-N-[4-(1-propyl-pyrrolidin-2-ylmethyl)-phenyl]-benzenesulfonamide 2-(4-Aminobenzyl)-1-propylpyrrolidine (300 mg, 1.37 mmol) was dissolved in pyridine-dichloromethane (1:2, 9 mL) and cooled to 5° C. 4-Isopropylbenzenesulfonyl chloride (300 mg, 0.24 mmol) was added and the solution stirred at 5° C. for 18 h. The solution was evaporated, partitioned between ethyl acetate and water, and the organic phase separated and dried over MgSO₄. The filtered solution was concentrated and separated by column chromatography (dichloromethane-2% methanol) to give an oil. The oil was dissolved in ethyl acetate and HCl (4M, dioxane) was added to give the product as a white solid (180 mg, 30%).

MS (ESI) m/z: 401.5 [M+H]⁺
¹H-NMR (DMSO-d₆): δ [ppm] 10.52 (s, 1H), 7.67 (d, 2H), 7.38 (d, 2H), 7.18 (d, 2H), 7.04 (d, 1H), 3.52 (m, 1H), 3.43 (m, 1H), 3.24 (m, 1H), 3.10-2.75 (m, 5H), 1.82 (m, 3H), 1.62 (m, 3H), 1.15 (d, 6H), 0.82 (t, 3H).
¹³C-NMR (DMSO-d₆): δ [ppm] 153.5 (s), 137.2 (s), 136.5 (s), 132.6 (s), 129.7 (d), 127.1 (d), 126.7 (d) 119.9(d), 68.1 (d), 54.5 (t), 52.8 (t), 35.2 (t), 33.2 (d), 29.1 (t), 26.8 (t), 23.3 (q), 21.1 (t), 18.2 (t), 11.0 (q).

Example 12

Reference

4-Isopropyl-N-[3-(1-propyl-pyrrolidin-2-ylmethyl)-phenyl]-benzenesulfonamide 2-(3-Aminobenzyl)-1-propylpyrrolidine (30 mg, 0.14 mmol) was converted to the target sulfonamide by a procedure identical to that described in example 11. The product was obtained as a white solid (18 mg, 26%).

MS (ESI) m/z: 401.5 [M+H]⁺
¹H-NMR (DMSO-d₆): δ [ppm] 10.81 (s, 1H), 10.32 (s, 1H), 7.70 (d, 2H), 7.47 (d, 2H), 7.18 (m, 1H), 6.97 (m, 2H), 3.42 (m, 2H), 3.30 (m, 1H), 3.13 (m, 1H), 3.02 (m, 1H), 2.85 (m, 2H), 1.88 (m, 2H), 1.62 (m, 4H), 1.15 (d, 6H), 0.82 (t, 3H).
¹³C-NMR (DMSO-d₆): δ [ppm] 153.6 (s), 138.1 (s), 136.9 (s), 129.4 (d), 127.1 (d), 126.9 (d), 124.5 (d) 120.2 (d), 118.4 (d), 67.8 (d), 54.2 (t), 52.6 (t), 35.7 (t), 33.2 (d), 28.9 (t), 26.8 (d), 23.3 (q), 20.9 (t), 18.2 (t), 11.0 (q).

Example 13

N-[4-(2-Allylamino-ethyl)-phenyl]-4-isopropyl-benzenesulfonamide×HCl

13.1 Allyl-{2-[4-(4-isopropyl-benzenesulfonylamino)-phenyl]-ethyl}-carbamic acid tert-butyl ester To a solution of allyl-[2-(4-amino-phenyl)ethyl]-carbamic acid tert-butyl ester (1.86 g, 6.74 mmol) in pyridine (25 ml) at 0° C. was added 4-isopropyl-benzenesulfonyl chloride (1.47 g, 6.74 mmol) and the mixture was stirred at 0° C. for 1 h. After concentration in vacuo the residue was partitioned between ethyl acetate and saturated aqueous NaHCO₃. The organic layer was washed with water, dried over MgSO₄, filtered and the solvent evaporated under reduced pressure. The residue was purified by column chromatography (n-heptane/ethyl acetate, 2/1) to give the product as a yellow resin (1.35 g, 43.6 mmol).

MS (ESI) m/z: 459.2 [M+H]⁺

13.2 N-[4-(2-Allylamino-ethyl)-phenyl]-4-isopropyl-benzenesulfonamide×HCl

To a solution of allyl-{2-[4-(4-isopropyl-benzenesulfonylamino)-phenyl]-ethyl}-carbamic acid tert-butyl ester (1.35 g, 2.94 mmol) in diethylether (25 ml) was added HCl in diethylether (1M, 10 ml), and the mixture was stirred for 2 h at room temperature. After concentration in vacuo the obtained residue was triturated with diethylether, filtered, washed with diethylether, and dried in vacuo to give the product as a yellow powder (1.16 g, 99.8%).

MS (ESI) m/z: 359.15 [M+H]⁺
¹H-NMR (DMSO-d₆): δ [ppm] 10.29 (s, 1H), 9.15 (bs, 2H), 7.69 (d, 2H), 7.42 (d, 2H), 7.05-7.12 (m, 4H), 5.85-5.96 (m, 1H), 5.35-5.48 (m, 2H), 3.50-3.59 (m, 2H), 2.8-3.09 (m, 5H), 1.19 (d, 6H).

Example 14

N-[4-(2-Allylamino-ethyl)-phenyl]-4-isopropyl-N-methyl-benzenesulfonamide×HCl

14.1 Allyl-(2-{4-[(4-isopropyl-benzenesulfonyl)-methyl-amino]-phenyl}-ethyl)-carbamic acid tert-butyl ester To a solution of allyl-{2-[4-(4-isopropyl-benzenesulfonylamino)-phenyl]-ethyl}-carbamic acid tert-butyl ester (200 mg, 0.44 mmol) in DMF (5 ml), 15-crown-5, and sodium hydride (20 mg, 0.48 mmol) were added, and the mixture was stirred at room temperature for 30 min. Methyliodide (60 mg, 0.44 mmol) was added and the mixture was stirred for 3 h at room temperature. After concentration in vacuo the residue was partitioned between dichloromethane and saturated aqueous NaHCO₃. The organic layer was washed with water, dried over MgSO₄, filtered and the solvent evaporated under reduced pressure to give the product as a yellow oil (200 mg, 97%).

MS (ESI) m/z: 417.1 [M+H]⁺

14.2 N-[4-(2-Allylamino-ethyl)-phenyl]-4-isopropyl-N-methyl-benzenesulfonamide×HCl To a solution of allyl-(2-{4-[(4-isopropyl-benzenesulfonyl)-methyl-amino]-phenyl}-ethyl)-carbamic acid tert-butyl ester (180 mg, 0.39 mmol) in diethylether (10 ml) was added HCl in diethylether (1M, 10 ml), and the mixture was stirred for 3 h at room temperature. After concentration in vacuo the obtained residue was dissolved in THF and with addition of n-pentane a precipitate was formed which was collected, washed with n-pentane and dried in vacuo to give the product as a yellow powder (110 mg, 68%).

MS (ESI) m/z: 373.15 [M+H]⁺
¹H-NMR (CDCl₃): δ [ppm] 9.93 (bs, 1H), 7.49 (d, 2H), 7.30 (d, 2H), 7.19 (m, 2H), 7.05 (d, 2H), 6.02-6.18 (m, 1H), 5.45-5.54 (m, 2H), 3.58-3.69 (m, 2H), 3.05-3.30 (m, 7H), 2.90-3.03 (m, 1H), 1.28 (d, 6H).

Example 15

N-[4-(2-Allylamino-ethyl)-phenyl]-4-isopropyl-N-propyl-benzenesulfonamide×HCl The desired product was obtained as a colorless powder following the synthetic procedure described for N-[4-(2-allylamino-ethyl)-phenyl]-4-isopropyl-N-methyl-benzenesulfonamide×HCl starting from Allyl-{2-[4-(4-isopropyl-benzenesulfonylamino)-phenyl]-ethyl}-carbamic acid tert-butyl ester and 1-bromo-propane.

MS (ESI) m/z: 401.25 [M+H]⁺
¹H-NMR (DMSO-d₆): δ [ppm] 9.19 (bs, 2H), 7.50 (d, 2H), 7.45 (d, 2H), 7.25 (d, 2H), 7.02 (d, 2H), 5.88-6.00 (m, 1H), 5.38-5.51 (m, 2H), 3.55-3.65 (m, 2H), 3.42-3.51 (m, 2H), 3.07-3.17 (m, 2H), 2.90-3.05 (m, 3H), 1.18-1.45 (m, 8H), 0.81 (t, 3H).

Example 16

N-[4-(2-Allylamino-ethyl)-phenyl]-4-trifluoromethoxy-benzenesulfonamide×HCl

The desired product was obtained as a yellow powder following the synthetic procedure described for N-[4-(2-allylamino-ethyl)-phenyl]-4-isopropyl benzenesulfonamide× HCl starting from allyl-[2-(4-amino-phenyl)-ethyl]-carbamic acid tert-butyl ester and 4-trifluoromethoxy-benzenesulfonyl chloride.

MS (ESI) m/z: 401.05 [M+H]⁺
¹H-NMR (DMSO-d₆): δ [ppm] 10.45 (bs, 1H), 9.01 (bs, 2H), 7.89 (d, 2H), 7.56 (d, 2H), 7.15 (d, 2H), 7.06 (d, 2H), 5.81-5.98 (m, 1H), 5.35-5.49 (m, 2H), 3.52-3.60 (m, 2H), 3.0-3.08 (m, 2H), 2.8-2.9 (m, 2H).

Example 17

N-[4-(2-Allylamino-ethyl)-phenyl]-N-methyl-4-trifluoromethoxy-benzenesulfonamide×HCl The desired product was obtained as a yellow powder following the synthetic procedure described for N-[4-(2-allylamino-ethyl)-phenyl]-4-isopropyl-N-methyl-benzenesulfonamide×HCl starting from Allyl-{2-[4-(4-trifluoromethoxy-benzenesulfonylamino)-phenyl]-ethyl}-carbamic acid tert-butyl ester and methyliodide.

MS (ESI) m/z: 415.15 [M+H]⁺
¹H-NMR (DMSO-d₆): δ [ppm] 9.12 (bs, 2H), 7.68 (d, 2H), 7.49 (d, 2H), 7.25 (d, 2H), 7.09 (d, 2H), 5.86-5.98 (m, 1H), 5.38-5.52 (m, 2H), 3.55-3.65 (m, 2H), 3.05-3.19 (m, 5H), 2.90-3.00 (m, 2H).

Example 18

N-[4-(2-Allylamino-ethyl)-phenyl]-N-propyl-4-trifluoromethoxy-benzenesulfonamide×HCl The desired product was obtained as a colorless powder following the synthetic procedure described for N-[4-(2-Allylamino-ethyl)-phenyl]-4-isopropyl-N-methyl-benzenesulfonamide×HCl starting from Allyl-{2-[4-(4-trifluoromethoxy-benzenesulfonylamino)-phenyl]-ethyl}-carbamic acid tert-butyl ester and 1-bromo-propane.

MS (ESI) m/z: 443.15 [M+H]⁺
¹H-NMR (DMSO-d₆): δ [ppm] 9.18 (bs, 2H), 7.70 (d, 2H), 7.59 (d, 2H), 7.26 (d, 2H), 7.05 (d, 2H), 5.87-6.00 (m, 1H), 5.38-5.50 (m, 2H), 3.48-3.65 (m, 4H), 3.08-3.18 (m, 2H), 2.92-3.01 (m, 2H), 1.26-1.35 (m, 2H), 0.82 (t, 3H).

Example 19

N-[4-(2-Diallylamino-ethyl)-phenyl]-4-isopropyl-benzenesulfonamide×HCl

19.1 {2-[4-(4-Isopropyl-benzenesulfonylamino)-phenyl]-ethyl}-carbamic acid tert-butyl ester To a solution of [2-(4-amino-phenyl)-ethyl]-carbamicacid tert-butyl ester (10.75 g, 45.49 mmol) in pyridine (125 ml) at 0° C. 4-Isopropyl-benzenesulfonyl chloride (10.45 g, 47.76 mmol) was added. The mixture was stirred at 0° C. for 1 h and 16 h at room temperature. After concentration in vacuo the residue was partitioned between dichloromethane and saturated aqueous NaHCO₃. The organic layer was washed with water, dried over MgSO₄, filtered and the solvent evaporated under reduced pressure to give the product as a brown oil (20.82 g, 50%).

19.2 N-[4-(2-Amino-ethyl)-phenyl]-4-isopropyl-benzenesulfonamide×HCl

To a solution of {2-[4-(4-isopropyl-benzenesulfonylamino)-phenyl]-ethyl}-carbamic acid tert-butyl ester (20.42 g, 48.79 mmol) in diethylether (200 ml) and THF (80 ml) at 0° C. HCl in diethylether (100 ml) was added slowly. The mixture was stirred at room temperature for 16 h. After concentration in vacuo the product was obtained as a yellow foam (17.3 g, 99.9%)

19.3 N-[4-(2-Diallylamino-ethyl)-phenyl]-4-isopropyl-benzenesulfonamide×HCl

A solution of N-[4-(2-Amino-ethyl)-phenyl]-4-isopropyl-benzenesulfonamide×HCl (740 mg, 2.09 mmol), 4 Å molecular sieves (750 mg) and cesium hydroxide (1.09 g, 6.27 mmol) in DMF was stirred at room temperature for 1 h before allylbromide (508 mg, 4.2 mmol) was added. The mixture was stirred at room temperature for 16 h. After concentrating the mixture in vacuo the residue was purified by column chromatography (toluene/THF/methanol, 4/1/1+ 2.5% triethylamine). The obtained yellow oil was dissolved in diethylether, and HCl in diethylether (1M) was added. The precipitate was collected and dried in vacuo to give the product as a colorless powder (210 mg, 23%).

MS (ESI) m/z: 399.15 [M+H]$^+$ $^1$H-NMR (DMSO-d$_6$): δ [ppm] 10.39 (s, 1H), 7.69 (d, 2H), 7.41 (d, 2H), 7.04-7.13 (m, 4H), 5.96-6.08 (m, 2H), 5.47-5.59 (m, 4H), 3.71-3.80 (m, 4H), 3.04-3.15 (m, 2H), 2.89-2.99 (m, 3H), 1.19 (d, 6H).

Example 20

N-[4-(2-Diallylamino-ethyl)-phenyl]-4-trifluoromethoxy-benzenesulfonamide×HCl

The desired product was obtained as a yellow foam following the synthetic procedure described for N-[4-(2-diallylamino-ethyl)-phenyl]-4-isopropyl-benzenesulfonamide× HCl starting from [2-(4-amino-phenyl)-ethyl]-carbamicacid tert-butyl ester and 4-trifluoromethoxy-benzenesulfonyl chloride.

MS (ESI) m/z: 441.15 [M+H]$^+$ $^1$H-NMR (DMSO-d$_6$): δ [ppm] 10.93 (bs, 1H), 10.45 (s, 1H), 7.89 (d, 2H), 7.55 (d, 2H), 7.14 (d, 2H), 7.06 (d, 2H), 5.93-6.09 (m, 2H), 5.46-5.59 (m, 4H), 3.68-3.84 (m, 4H), 3.04-3.17 (m, 2H), 2.90-3.01 (m, 2H).

Example 21

Reference

N-[3-(2-Allylamino-ethyl)-phenyl]-4-isopropyl-benzenesulfonamide

The desired product was obtained as a pink powder following the synthetic procedure described for N-[4-(2-Allylamino-ethyl)-phenyl]-4-isopropyl-benzenesulfonamide× HCl starting from allyl-[2-(3-amino-phenyl)-ethyl]-carbamic acid tert-butyl ester and 4-Isopropyl-benzenesulfonyl chloride.

MS (ESI) m/z: 359.15 [M+H]$^+$ $^1$H-NMR (DMSO-d$_6$): δ [ppm] 10.30 (s, 1H), 9.09 (bs, 2H), 7.69 (d, 2H), 7.42 (d, 2H), 7.19 (t, 1H), 6.95-7.03 (m, 2H), 6.90 (d, 1H), 5.85-5.98 (m, 1H), 5.38-5.50 (m, 2H), 2.80-3.05 (several m, 5H), 1.19 (d, 6H).

Example 22

N-[3-(2-Allylamino-ethyl)-phenyl]-4-trifluoromethoxy-benzenesulfonamide

The desired product was obtained as a pink powder following the synthetic procedure described for N-[4-(2-allylamino-ethyl)-phenyl]-4-isopropyl-benzenesulfonamide×HCl starting from allyl-[2-(3-amino-phenyl)-ethyl]-carbamic acid tert-butyl ester and 4-trifluoromethoxy-benzenesulfonyl chloride.

MS (ESI) m/z: 401.05 [M+H]$^+$ $^1$H-NMR (DMSO-d$_6$): δ [ppm]10.48 (s, 1H), 9.05 (bs, 2H), 7.89 (d, 2H), q 7.55 (d, 2H) 7.20 (t, 1H), 6.91-7.03 (m, 3H), 5.85-5.98 (m, 1H), 5.38-5.50 (m, 2H), 3.52-3.62 (m, 2H), 2.95-3.05 (m, 2H), 2.82-2.90 (m, 2H).

Example 23

Diallyl-{2-[4-(4-isopropyl-benzenesulfonylmethyl)-phenyl]-ethyl}-amine×HCl 23.1 2-(4-Bromomethyl-phenyl)-acetamide To a solution of (4-bromomethyl-phenyl)-acetic acid (9.23 g, 40.30 mmol) and N,N-dimethylformamide (0.5 ml, 6.47 mmol) in toluene (100 ml) thionyl chloride (3.1 ml, 42.31 mmol) was added. The mixture was heated at 80° C. for 1 h. At 0° C., this mixture was added to a solution of ammonia in water (25%, 200 ml). After stirring for 30 min the precipitate was collected, washed with water and pentane, and dried in a vacuum oven at 50° C. to give the product as white crystals (5.8 g, 63%).

23.2 2-[4-(4-Isopropyl-benzenesulfonylmethyl)-phenyl]-acetamide

To a solution of 4-(isopropyl)thiophenol (1.91 g, 12.54 mmol) in N,N-dimethylformamide (50 ml) sodium hydride (530 mg, 13.17 mmol) was added. The exothermic reaction was allowed to cool down to room temperature. At 15° C., a solution of 2-(4-bromomethyl-phenyl)-acetamide (2.86 g, 12.54 mmol) in N,N-dimethylformamide (25 ml) was added. After stirring the reaction mixture at room temperature for 16 h, the mixture was poured into ice-water. The precipitate was collected, washed with water and pentane, and dried in a vacuum oven at 50° C. to give the title compound as a white powder (3.46 g, 92%). This powder was used without further purification in the next step.

The powder obtained above was dissolved in methanol (100 ml). At 0-5° C. a solution of oxone (20.6 g, 33.5 mmol) in water (75 ml) was added. The mixture was stirred at 0° C. for 1 h and at room temperature for 16 h. On diluting the mixture with water a white solid was formed, which was collected, washed with water and pentane, and dried in a vacuum oven at 50° C. to give 2-[4-(4-isopropyl-benzenesulfonylmethyl)-phenyl]-acetamide as a white powder (3.39 g, 92%).

23.3 2-[4-(4-Isopropyl-benzenesulfonylmethyl)-phenyl]-ethylamine×HCl

A solution of 2-[4-(4-isopropyl-benzenesulfonylmethyl)-phenyl]-acetamide (1.37 g, 4.13 mmol) in tetrahydrofuran (30 ml) was refluxed and then a solution of borane-dimethylsulfid complex (2M in tetrahydrofuran, 10.33 mmol) was added. The mixture was refluxed for 2 h. The mixture was allowed to cool down to room temperature and adjusted to pH=1 with a solution of HCl in ethanol (2M). After stirring the mixture for 15 min the solvents were evaporated under reduce pressure. Diethyl ether was added to residue. A slurry of the resulting white powder in diethyl ether was stirred for 15 min. The remaining solid was collected, washed with diethyl ether, and dried in a vacuum oven to give white crystals of 2-[4-(4-isopropyl-benzenesulfonylmethyl)-phenyl]-ethylamine×HCl (1.36 g, 92.6%).

MS (ESI) m/z: 318.15 [M+H]$^+$ 23.4 Diallyl-{2-[4-(4-isopropyl-benzenesulfonylmethyl)-phenyl]-ethyl}-amine×HCl To a solution of 2-[4-(4-isopropyl-benzenesulfonylmethyl)-phenyl]-ethylamine×HCl (0.81 g, 2.27 mmol) in N,N-dimethylformamide (30 ml) cesium hydroxide (1.2 g, 6.9 mmol) was added. After the mixture was stirred for 1 h, allylbromide (0.83 g, 6.8 mmol) was added. The mixture was stirred for 16 h. The solvents were evaporated under reduced pressure and the residue was purified by column chromatography (toluene:tetrahydrofuran:methanol, 4:1:1, +2.5% triethylamine). A solution of HCl in isopropanol (1M) was added to the resulting oil. The precipitate was collected, washed with pentane, and dried in vacuo to give a white powder (0.5 g, 50%).

MS (ESI) m/z: 398.20 [M+H]$^+$ $^1$H-NMR (DMSO-d$_6$): δ [ppm] 11.10 (bs, 1H), 7.68 (d, 2H), 7.49 (d, 2H), 7.29 (d, 2H), 7.15 (d, 2H), 5.95-6.12 (m, 2H), 5.47-5.65 (m, 4H), 4.61 (m, 2H), 3.68-3.88 (m, 4H), 2.92-3.25 (m, 3H), 1.22 (d, 6H).

Example 24

Diallyl-{2-[4-(4-trifluoromethoxy-benzenesulfonyl-methyl)-phenyl]-ethyl}-amine×HCl 24.1 2-[4-(4-Trifluoromethoxy-benzenesulfonylmethyl)-phenyl]-acetamide To a solution of 4-(trifluoromethoxy)thiophenol (2.86 g, 12.54 mmol) in N,N-dimethylformamide (50 ml) sodium hydride (530 mg, 13.17 mmol) was added. The exothermic reaction was allowed to cool down to room temperature. At 15° C. a solution of 2-(4-bromomethyl-phenyl)-acetamide (2.86 g, 12.54 mmol) in N,N-dimethylformamide (25 ml) was added. After stirring the reaction mixture at room temperature for 16 h the mixture was added to ice-water. The precipitate was collected, washed with water and pentane, and dried in a vacuum oven at 50° C. to give the product as a yellow powder (3.56 g, 83%).

The thus obtained powder, which was used without further purification, was dissolved in methanol (200 ml). At room temperature a solution of oxone (18.4 g, 29.9 mmol) in water (75 ml) was added. The mixture was stirred at room temperature for 16 h and additional 3 h at 50° C. Upon diluting the mixture with water a white solid was formed, which was collected, washed with water and pentane, and dried in a vacuum oven at 50° C. to give 2-[4-(4-trifluoromethoxy-benzenesulfonylmethyl)-phenyl]-acetamide as a white powder (2.66 g, 71%).

24.2 2-[4-(4-Trifluoromethoxy-benzenesulfonylmethyl)-phenyl]-ethylamine×HCl

A solution of 2-[4-(4-trifluoromethoxy-benzenesulfonylmethyl)-phenyl]-acetamide (1.36 g, 3.64 mmol) in tetrahydrofuran (30 ml) was refluxed and a solution of borane-dimethylsulfid complex (2M in tetrahydrofuran, 9.11 mmol) was added. The mixture was refluxed for 2 h. The mixture was allowed to come to room temperature and was adjusted to pH=1 using a solution of HCl in ethanol (2M). After stirring the mixture for 15 min the solvents were evaporated under reduced pressure. A slurry of the resulting white powder in diethyl ether was stirred for 15 min. The remaining solid was collected, washed with diethyl ether, and dried in a vacuum oven to give white crystals of 2-[4-(4-trifluoromethoxy-benzenesulfonylmethyl)-phenyl]-ethylamine×HCl (1.22 g, 84.7%).

MS (ESI) m/z: 360.05 [M+H]$^+$ 24.3 Diallyl-{2-[4-(4-trifluoromethoxy-benzenesulfonylmethyl)-phenyl]-ethyl}-amine×HCl To a solution of 2-[4-(4-trifluoromethoxy-benzenesulfonylmethyl)-phenyl]-ethylamine×HCl (1.14 g, 2.89 mmol) in N,N-dimethylformamide (30 ml) cesium hydroxide (1.5 g, 8.7 mmol) was added. After the mixture was stirred for 1 h, allylbromide (1.05 g, 8.7 mmol) was added. The mixture was stirred for 16 h. The solvents were evaporated in vacuo and the residue was purified by column chromatography (toluene:tetrahydrofuran:methanol, 4:1:1, +2.5% triethylamine). To the resulting oil a solution of HCl in isopropanol (1M) was added. The precipitate was collected, washed with pentane and dried in vacuo to give a white powder (0.78 g, 56%)

MS (ESI) m/z: 440.15 [M+H]$^+$ $^1$H-NMR (DMSO-d$_6$): δ [ppm] 11.40 (bs, 1H), 7.88 (d, 2H), 7.60 (d, 2H), 7.20 (d, 2H), 7.15 (d, 2H), 5.98-6.11 (m, 2H), 5.49-5.65 (m, 4H), 4.71 (m, 2H), 3.70-3.85 (m, 4H), 3.30-3.40 (m, 2H), 3.00-3.22 (m, 4H).

Example 25

Dipropyl-{2-[4-(4-isopropyl-benzenesulfonylmethyl)-phenyl]-ethyl}-amine×HCl

To a solution of diallyl-{2-[4-(4-isopropyl-benzenesulfonylmethyl)-phenyl]-ethyl}-amine×HCl (90 mg, 0.21 mmol) in ethanol (25 ml) a suspension of palladium on charcoal (10%, 100 mg) in ethanol was added. The mixture was hydrogenated at atmospheric pressure. After filtration and removal of the solvents in vacuo the resulting oil was triturated with diethyl ether. The precipitate was collected, washed with diethyl ether and dried in vacuo to give the product as a yellow foam (30 mg, 36.2%).

MS (ESI) m/z: 402.25 [M+H]$^+$ $^1$H-NMR (DMSO-d$_6$): δ [ppm] 10.30 (bs, 1H), 7.67 (d, 2H), 7.49 (d, 2H), 7.25 (d, 2H), 7.15 (d, 2H), 4.61 (m, 2H), 3.15-3.29 (m, 2H), 2.92-3.15 (m, 7H), 1.6-1.8 (m, 4H), 1.23 (d, 6H), 0.92 (t, 6H).

Example 26

Dipropyl-{2-[4-(4-trifluoromethoxy-benzenesulfonylmethyl)-phenyl]-ethyl}-dipropyl-amine×HCl To a solution of diallyl-{2-[4-(4-trifluoromethoxy-benzenesulfonylmethyl)-phenyl]-ethyl}-amine×HCl (160 mg, 0.34 mmol) in ethanol (25 ml) a suspension of palladium on charcoal (10%, 150 mg) in ethanol was added. The mixture was hydrogenated at atmospheric pressure. After filtration and removal of the solvents in vacuo the resulting oil was triturated with diethyl ether. The precipitate was collected, washed with diethyl ether and dried in vacuo to give the product as a colourless powder (120 mg, 70%).

MS (ESI) m/z: 444.15 [M+H]$^+$ $^1$H-NMR (DMSO-d$_6$): δ [ppm] 10.30 (bs, 1H), 7.89 (d, 2H), 7.59 (d, 2H), 7.25 (d, 2H), 7.13 (d, 2H), 4.71 (m, 2H), 3.15-3.29 (m, 2H), 2.98-3.15 (m, 6H), 1.61-1.78 (m, 4H), 0.92 (t, 6H).

Example 27

Allyl-{2-[4-(4-isopropyl-benzenesulfonylmethyl)-phenyl]-ethyl}-amine×HCl

2-[4-(4-Isopropyl-benzenesulfonylmethyl)-phenyl]-ethylamine×HCl (0.81 g, 2.27 mmol) was dissolved in a solution of sodium hydroxide in methanol (1M, 2.27 mmol), the methanol was removed and N,N-dimethylformamide (20 ml) was added. To a solution of the resulting 2-[4-(4-isopropyl-benzenesulfonylmethyl)-phenyl]-ethylamine in N,N-dimethylformamide activated 4 Å molecular sieves (700 mg) and cesium hydroxide (40 mg, 0.228 mmol) were added. The mixture was stirred at room temperature for 1 h. After addition of allybromide (0.82 g, 6.81 mmol) the mixture was stirred at room temperature for 16 h. The solvents were evaporated in vacuo and the residue was purified by column chromatography (toluene:tetrahydrofuran:methanol, 4:1:1, +2.5% triethylamine). To the resulting oil a solution of HCl in isopropanol (1M) was added. The precipitate was collected, washed with pentane, and dried in vacuo to give a white powder (0.14 g, 15%).

MS (ESI) m/z: 358.15 [M+H]$^+$ $^1$H-NMR (DMSO-d$_6$): δ [ppm] 9.01-9.20 (m, 1H), 7.68 (d, 2H), 7.49 (d, 2H), 7.19 (d, 2H), 7.12 (d, 2H), 5.85-5.99 (m, 1H), 5.39-5.52 (m, 2H), 4.60 (s, 2H), 3.55-3.65 (m, 2H), 2.90-3.15 (m, 5H), 1.22 (d, 6H).

Example 28

{2-[4-(4-Isopropyl-benzenesulfonylmethyl)-phenyl]-ethyl}-propyl-amine×HCl 28.1 [4-(4-Isopropyl-phenylsulfanylmethyl)-phenyl]-acetic acid To a solution of 4-(isopropyl)thiophenol (10 g, 65.68 mmol) in N,N-dimethylformamide (200 ml) sodium hydride (3.15 g, 131.35 mmol) was added. The exothermic reaction was allowed to cool down to room temperature. At 15° C. a solution of (4-bromomethyl-phenyl)-acetic acid (15.04 g, 65.68 mmol) in N,N-dimethylformamide (100 ml) was added. After stirring the reaction mixture at room temperature for 16 h the mixture was concentrated, diluted with water, and adjusted to pH=2 by adding HCl (2N). The aqueous phase was extracted three times with ethyl acetate. The combined organic layers were dried over MgSO$_4$, filtered, and the solvent evaporated under reduced pressure to give the product as a yellow oil (19.5 g, 99%).

MS (ESI) m/z: 301.15 [M+H]$^+$ 28.2 [4-(4-Isopropyl-benzenesulfonylmethyl)-phenyl]-acetic acid A solution of [4-(4-isopropyl-phenylsulfanylmethyl)-phenyl]-acetic acid (20.3 g, 67.57 mmol) in acetic acid (100 ml) was heated to 70° C. and hydrogen peroxide (24.5 g, 216.23 mmol) was added over a period of 10 min. The mixture was stirred at 70° C. for 2 h. The mixture was poured into ice-water and the precipitate was filtered, washed with diisopropyl ether and dried in vacuo to give the product as a colorless powder (19.9 g, 89%).

28.3 2-[4-(4-Isopropyl-benzenesulfonylmethyl)-phenyl]-N-propyl-acetamide

To a solution of [4-(4-isopropyl-benzenesulfonylmethyl)-phenyl]-acetic acid (1 g, 3.00 mmol) in pyridine (15 ml)/N,N-dimethylformamide (15 ml) N,N'-carbonyldiimidazole (0.54 g, 3.31 mmol) was added and the mixture heated to 50° C. for 1 h. At 0° C. propylamine was added. The mixture was stirred at room temperature for 16 h. Then, the mixture was poured into water. The precipitate was collected and dried in a vacuum oven at 70° C. to give the product as a yellow powder (0.89 g, 2.39 mmol).

MS (ESI) m/z: 374.15 [M+H]$^+$ 28.4 {2-[4-(4-Isopropyl-benzenesulfonylmethyl)-phenyl]-ethyl}-propyl-amine To a solution of 2-[4-(4-isopropyl-benzenesulfonylmethyl)-phenyl]-N-propylacetamide (500 mg, 1.34 mmol) in tetrahydrofuran (30 ml) borane-tetrahydrofuran complex (2M in tetrahydrofuran, 6.70 mmol) was added at 0° C. The mixture was stirred at room temperature for 16 h after which a solution of HCl in ethanol (1M) was added and the mixture was stirred for 2 h. The mixture was concentrated in vacuo, diluted with water, and adjusted to pH=10 by adding aqueous NaOH. The aqueous phase was extracted three times with ethyl acetate. The combined organic layers were dried over MgSO$_4$, filtered, and the solvent was evaporated under reduced pressure. The residue was purified by preparative HPLC (water/methanol/0.1% acetic acid) to give the product as a colorless powder (130 mg, 27%).

MS (ESI) m/z: 360.25 [M+H]$^+$ $^1$H-NMR (DMSO-d$_6$): δ [ppm] 7.68 (d, 2H), 7.49 (d, 2H), 7.19 (d, 2H), 7.12 (d, 2H), 4.59 (m, 2H), 2.83-3.10 (m, 5H), 2.68-2.82 (m, 2H), 1.52-1.68 (m, 2H), 1.22 (d, 6H), 0.90 (t, 6H).

III. Examples of Galenic Administration Forms

A) Tablets

Tablets of the following composition are pressed on a tablet press in the customary manner:
  40 mg of substance from Example 8
  120 mg of corn starch
  13.5 mg of gelatin
  45 mg of lactose
  2.25 mg of Aerosil® (chemically pure silicic acid in sub-microscopically fine dispersion)
  6.75 mg of potato starch (as a 6% paste)

B) Sugar-coated tablets
  20 mg of substance from Example 8
  60 mg of core composition
  70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

IV. Biological Investigations

Receptor Binding Studies:
  The substance to be tested was either dissolved in methanol/Chremophor® (BASF-AG) or in dimethyl sulfoxide and then diluted with water to the desired concentration.
Dopamine D$_3$ Receptor:
  The assay mixture (0.250 ml) was composed of membranes derived from ~10$^6$ HEK-293 cells possessing stably expressed human dopamine D$_3$ receptors, 0.1 nM [$^{125}$I]-iodosulpride and incubation buffer (total binding) or, in addition, test substance (inhibition curve) or 1 µM spiperone (nonspecific binding). Each assay mixture was run in triplicate.
  The incubation buffer contained 50 mM tris, 120 mM NaCl, 5 mM KCl, 2 mM CaCl$_2$, 2 mM MgCl$_2$ and 0.1% bovine serum albumin, 10 µM quinolone and 0.1% ascorbic acid (prepared fresh daily). The buffer was adjusted to pH 7.4 with HCl.
Dopamine D$_{2L}$ Receptor:
  The assay mixture (1 ml) was composed of membranes from ~10$^6$ HEK-293 cells possessing stably expressed human dopamine D$_{2L}$ receptors (long isoform) and 0.01 nM [$^{125}$I] iodospiperone and incubation buffer (total binding) or, in addition, test substance (inhibition curve)

or 1 μM haloperidol (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptro binding studies are expressed as receptor binding constants $K_i(D_2)$ and $K_i(D_3)$, respectively, as herein before described, and given in table 3.

In these tests, the compounds according to the invention exhibit very good affinities for the $D_3$ receptor (<10 nM, frequently <5 nM) and bind selectively to the $D_3$ receptor.

The results of the binding tests are given in table 3.

TABLE 3

| Example | $K_i(D3)$* [nM] | $K_i(D2)$*/$K_i(D3)$* |
|---|---|---|
| 1 | 43 | 41 |
| 2 | 21 | 57 |
| 3 | 2.8 | 33 |
| 6 | 2.2 | 22 |
| 7 | 18 | 23 |
| 8 | 0.2 | 54 |
| 9 | 2 | 40 |
| 10 | 42 | 53 |
| 11 | 0.58 | 16 |
| 13 | 1.7 | 74 |
| 14 | 27 | 40 |
| 15 | 22 | 22 |
| 16 | 31 | 79 |
| 17 | 34 | 75 |
| 18 | 37 | 24 |
| 19 | 2.7 | 42 |
| 20 | 64 | 65 |
| 21 ref. | 22 | 62 |
| 23 | 8.4 | 59 |
| 25 | 0.5 | 175 |
| 26 | 3.9 | 170 |
| 28 | 4.8 | 130 |

*Receptor binding constants obtained according to the assays described herein before

We claim:
1. An aminoethylaromatic compound of the formula I

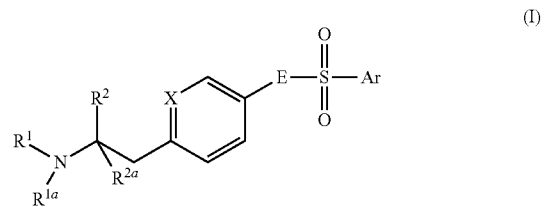

wherein

Ar is phenyl wherein Ar optionally carries 1 radical $R^a$ wherein if Ar carries $R^a$, Ar optionally carries 1 or 2 radicals $R^b$;

$R^a$ being selected from the group consisting of $C_1$-$C_6$-alkyl, $C_2$-$C_6$-alkenyl, fluorinated $C_2$-$C_6$-alkenyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_6$-alkoxy-$C_1$-$C_4$-alkyl, $C_1$-$C_6$-hydroxyalkoxy, $C_1$-$C_6$-alkoxy-$C_1$-$C_4$-alkoxy, COOH, $NR^4R^5$, $CH_2NR^4R^5$, $ONR^4R^5$, $NHC(O)NR^{41}e$, $C(O)NR^4R^5$, $SO_2NR^4R^5$, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl, fluorinated $C_1$-$C_6$-alkylsulfonyl, phenylsulfonyl, phenyl, phenoxy, benzyloxy and a 3- to 7-membered heterocyclic radical, wherein the five last mentioned radicals may carry 1, 2, 3 or 4 radicals selected from halogen, cyano, OH, oxo, CN, and the radicals $R^a$;

$R^b$ being, independently from each other, selected from halogen, cyano, nitro, OH, methyl, methoxy, fluoromethyl, difluoromethyl, trifluoromethyl, fluormethoxy, difluoromethoxy and trifluoromethoxy;

X is CH;

E is $CR^6R^7$;

$R^1$ is $C_1$-$C_4$-alkyl, $C_3$-$C_4$-cycloalkyl, $C_3$-$C_4$-cycloalkylmethyl, $C_3$-$C_4$-alkenyl, fluorinated $C_1$-$C_4$-alkyl, fluorinated $C_3$-$C_4$-cycloalkyl, fluorinated $C_3$-$C_4$-cycloalkylmethyl, fluorinated $C_3$-$C_4$-alkenyl, formyl or $C_1$-$C_3$-alkylcarbonyl;

$R^{1a}$ is H, $C_1$-$C_4$-alkyl, $C_3$-$C_4$-cycloalkyl, $C_3$-$C_4$-cycloalkylmethyl, $C_3$-$C_4$-alkenyl, fluorinated $C_3$-$C_4$-alkyl, fluorinated $C_3$-$C_4$-cycloalkyl, fluorinated $C_3$-$C_4$-cycloalkylmethyl, fluorinated $C_1$-$C_4$-alkenyl, or $R^{1a}$ and $R^2$ together are $(CH_2)_n$ with n being 2, 3 or 4, or $R^{1a}$ and $R^2$ together are $(CH_2)_n$ with n being 2, 3 or 4;

$R^2$, $R^{2a}$ are independently of each other H, $C_1$-$C_4$-alkyl or fluorinated $C_1$-$C_4$-alkyl;

$R^4$, $R^5$ independently of each other are selected from H, $C_1$-$C_3$-alkyl, $C_1$-$C_3$-alkoxy and fluorinated $C_1$-$C_3$-alkyl;

$R^6$, $R^7$ independently of each other are selected from H, fluorine, $C_1$-$C_4$-alkyl and fluorinated $C_1$-$C_4$-alkyl or together form a moiety $(CH_2)_p$ with p being 2, 3, 4 or 5;

and the physiologically tolerated acid addition salts of these compounds.

2. The compounds as claimed in claim 1, wherein Ar is phenyl wherein Ar carries one radical $R^a$ which is selected from the group consisting of $C_2$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^4R^5$, 1-aziridinyl, azetidin-1-yl, pyrrolidin-1-yl or piperidin-1-yl, wherein the last four mentioned radicals may be fluorinated, a phenyl group and an aromatic 5- or 6-membered C-bound heteroaromatic radical, comprising 1 nitrogen atom as ring member and 0, 1, 2 or 3 further heteroatoms, independently of each other, selected from 0, S and N, wherein the last two mentioned radicals may carry 1, 2, 3 or 4 radicals selected from halogen and the radicals $R^a$; and wherein Ar may carry 1 or 2 further radicals $R^b$, which are independently from each other selected from halogen, cyano, methyl, fluoromethyl, difluoromethyl, trifluoromethyl, difluoromethoxy and trifluoromethoxy; and wherein $R^4$, $R^5$, independently of each other are selected from H, $C_1$-$C_3$-alkyl and fluorinated $C_1$-$C_3$-alkyl.

3. The compounds as claimed in claim 1, wherein Ar carries one radical $R^a$ of the formula $R^{a'}$

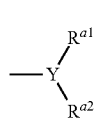

wherein
Y is N, CH or CF,
$R^{a1}$ and $R^{a2}$ are independently of each other selected from $C_1$-$C_2$-alkyl, $C_1$-$C_2$-alkoxy, fluorinated $C_1$-$C_2$-alkyl, provided for Y being CH or CF one of the radicals $R^{a1}$ or $R^{a2}$ may also be hydrogen or fluorine, or.

4. The compounds as claimed in claim 3, wherein the radical $R^{a'}$ is selected from isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyhethyl, 1-(difluoromethyl)-2,2-difluoroethyl, cyclopropyl, cyclobutyl, 1-fluorocyclopropyl, and 2-fluorocyclopropyl.

5. The compounds as claimed in claim 3, wherein the radical $R^{a'}$ is selected from 4-morpholinyl, 4-thiomorpholinyl, 4-(1,1-dioxo)thiomorpholinyl, piperazin-1-yl, 4-methylpiperazin-1-yl, azetidin-1-yl, 2-methylazetidin-1-yl, (S)-2-methylazetidin-1-yl, (R)-2-methylazetidin-1-yl, 3-fluoroazetidin-1-yl, 3-methoxyazetidin-1-yl, 3-hydroxyazetidin-1-yl, pyrrolidin-1-yl, pyrrolidin-2-yl, (S)-pyrrolidin-2-yl, (R)-pyrrolidin-2-yl, pyrrolidin-3-yl, (S)-pyrrolidin-3-yl, (R)-pyrrolidin-3-yl, 2-fluoropyrrolidin-1-yl, (S)-2-fluoropyrrolidin-1-yl, (R)-2-fluoropyrrolidin-1-yl, 3-fluoropyrrolidin-1-yl, (S)-3-fluoropyrrolidin-1-yl, (R)-3-fluoropyrrolidin-1-yl, 2,2-difluoropyrrolidin-1-yl, 3,3-difluoropyrrolidin-1-yl, 2-methylpyrrolidin-1-yl, (S)-2-methylpyrrolidin-1-yl, (R)-2-methylpyrrolidin-1-yl, 3-methylpyrrolidin-1-yl, (S)-3-methylpyrrolidin-1-yl, (R)-3-methylpyrrolidin-1-yl, 1-methylpyrrolidin-2-yl, (S)-1-methylpyrrolidin-2-yl, (R)-1-methylpyrrolidin-2-yl, 1-methylpyrrolidin-3-yl, (S)-1-methylpyrrolidin-3-yl, (R)-1-methylpyrrolidin-3-yl, 2,2-dimethylpyrrolidin-1-yl, 3,3-dimethylpyrrolidin-1-yl, 2-trifluoromethylpyrrolidin-1-yl, (S)-2-trifluoromethylpyrrolidin-1-yl, (R)-2-trifluoromethylpyrrolidin-1-yl, 3-trifluoromethylpyrrolidin-1-yl, (S)-3-trifluoromethylpyrrolidin-1-yl, (R)-3-trifluoromethylpyrrolidin-1-yl, 2-oxopyrrolidin-1-yl, 2-oxo-oxazolidin-3-yl, piperidin-1-yl, 2-methylpiperidin-1-yl, (S)-2-methylpiperidin-1-yl and (R)-2-methylpiperidin-1-yl.

6. The compounds as claimed in claim 3, wherein the radical $R^{a'}$ carries 1, 2, 3 or 4 fluorine atoms.

7. The compounds as claimed in claim 1, wherein Ar carries one radical $R^a$, which is selected from $CHF_2CH_2F$, $OCHF_2$ and $OCH_2F$.

8. The compounds as claimed in claim 1, wherein Ar carries one radical $R^a$, which is selected from 5- or 6-membered heteroaromatic radicals having as ring members 1 heteroatom selected from O, S and N and which may further have 1, 2 or 3 nitrogen atoms as ring members, and wherein the 5- or 6-membered heteroaromatic radical may carry 1, 2 or 3 substituents selected from halogen, $NO_2$, $NH_2$, OH, CN, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $C_1$-$C_6$-hydroxyalkyl, $C_1$-$C_4$-alkoxy-$C_1$-$C_4$-alkyl, $C_1$-$C_6$-hydroxyalkoxy, $C_1$-$C_4$-alkoxy-$C_2$-$C_4$-alkoxy, $C_1$-$C_6$-alkylcarbonyl, $C_1$-$C_6$-alkylamino, di-$C_1$-$C_6$-alkylamino, $C_1$-$C_6$-alkylaminocarbonyl, di-$C_1$-$C_6$-alkylaminocarbonyl, fluorinated $C_1$-$C_6$-alkylcarbonyl, $C_1$-$C_6$-alkylcarbonylamino, fluorinated $C_1$-$C_6$-alkylcarbonylamino, $C_1$-$C_6$-alkylcarbonyloxy, fluorinated $C_1$-$C_6$-alkylcarbonyloxy, $C_1$-$C_6$-alkoxycarbonyl, $C_1$-$C_6$-alkylthio, fluorinated $C_1$-$C_6$-alkylthio, $C_1$-$C_6$-alkylsulfinyl, $C_1$-$C_6$-alkylsulfonyl, fluorinated $C_1$-$C_6$-alkylsulfinyl and fluorinated $C_1$-$C_6$-alkylsulfonyl.

9. The compounds as claimed in claim 8, wherein Ar carries one heteroaromatic radical $R^a$, which is selected from furanyl, thienyl, pyrrolyl, pyrazolyl, imidazolyl, oxazolyl, isoxazolyl, 1,3,4-thiadiazolyl, 1,2,4-triazolyl, 1,2,3-triazolyl and tetrazolyl, where the heteroaromatic radical may be unsubstituted or may carry 1 to 3 substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

10. The compounds as claimed in claim 1, wherein Ar is phenyl.

11. The compounds as claimed in claim 1, wherein Ar is phenyl that carries a radical $R^a$ in the 4-position of the phenyl ring.

12. The compound as claimed in claim 1, wherein X is CH.

13. The compound as claimed in claim 1, wherein $R^1$ is n-propyl, fluorinated $C_2$-$C_3$-alkyl or 1-propen-3-yl.

14. The compound as claimed in claim 1, wherein $R^{1a}$ is hydrogen.

15. The compound as claimed in claim 1, wherein $R^{2a}$ is hydrogen.

16. The compound as claimed in claim 15, wherein both $R^{2a}$ and $R^2$ are hydrogen.

17. The compound as claimed in claim 1, wherein one of the radicals $R^{2a}$ and $R^2$ is hydrogen while the other is methyl.

18. The compound as claimed in claim 1, wherein $R^{1a}$ is n-propyl or 1-propen-3-yl.

19. A pharmaceutical composition comprising at least one compound of the formula I or a pharmaceutically acceptable salt thereof as claimed in claim 1, optionally together with at least one physiologically acceptable carrier or auxiliary substance.

* * * * *